United States Patent [19]
Reitz et al.

[11] Patent Number: 5,393,790
[45] Date of Patent: Feb. 28, 1995

[54] SUBSTITUTED SPIRO COMPOUNDS FOR THE TREATMENT OF INFLAMMATION

[75] Inventors: David B. Reitz, Chesterfield; Robert E. Manning, St. Louis; Horng-Chi Huang; Jinglin Li, both of Chesterfield, all of Mo.

[73] Assignee: G.D. Searle & Co., Chicago, Ill.

[21] Appl. No.: 194,762

[22] Filed: Feb. 10, 1994

[51] Int. Cl.$^6$ .................. C07C 309/32; C07C 317/14; C07D 211/54; A61K 31/18

[52] U.S. Cl. ..................... 514/709; 514/278; 514/520; 514/524; 514/602; 514/603; 514/604; 514/883; 514/886; 546/15; 558/412; 558/413; 564/84; 564/85; 564/86; 564/89; 564/90; 568/29; 568/33; 568/34

[58] Field of Search ............... 514/278, 520, 524, 602, 514/603, 604, 709, 883, 886; 546/15; 558/412, 413; 564/84, 85, 86, 89, 90; 568/29, 33, 34

[56] References Cited

U.S. PATENT DOCUMENTS

3,214,470 10/1965 Grogan .
3,728,404 4/1973 Kubicek .

FOREIGN PATENT DOCUMENTS

4212628 10/1993 Germany .

OTHER PUBLICATIONS

T. Hla and K. Nielson, *Proc. Natl. Acad. Sci.*, USA, 89, 7384 (1992).
J. Masferrer, et al, *Proc. Natl. Acad. Sci.*, USA, 89, 3917 (1992).
E. Meade et al, *Biol. Chem.*, 268, 6610 (1993).
Futaki et al, *Gen. Pharmac.*, 24, 105 (1993).
H. Ohashi et al, *Phytochemistry*, 31, 1371 (1992).
D. Y. Curtin et al, *J. Org. Chem*, 36, 565 (1971).
O. P. Malik et al, *Ind. J. Chem.*, 14B, 975 (1976).
J. B. M. Somers et al, *J. Photochem. Photobiol.*, 48A, 353 (1989).
W. H. Laarhoven, *Pure & Appl. Chem.*, 56, 1225–40 (1984).
E. J. Corey et al., *J. Amer. Chem. Soc.*, 85, 1788 (1963).

*Primary Examiner*—Peter O'Sullivan
*Attorney, Agent, or Firm*—Joseph W. Bulock; J. Timothy Keane

[57] ABSTRACT

A class of substituted spiro compounds is described for use in treating inflammation and inflammation-related disorders. Compounds of particular interest are defined by Formula III:

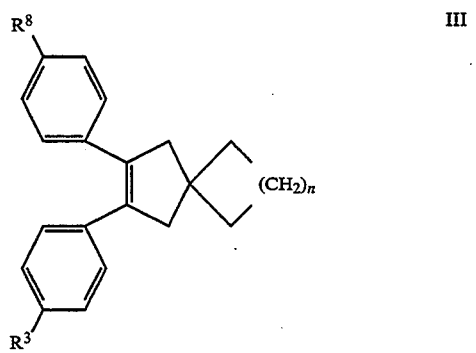

wherein n is a number selected from 0, 1 and 2; wherein $R^3$ is methylsulfonyl or sulfamyl; and wherein $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; or a pharmaceutically-acceptable salt thereof.

41 Claims, No Drawings

SUBSTITUTED SPIRO COMPOUNDS FOR THE TREATMENT OF INFLAMMATION

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci. USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc, Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Gen. Pharmac.*, 24, 105 (1993)) has reported that N-(2-cyclohexyloxy-4-nitrophenyl)methanesulfonamide is antiinflammatory and lacks gastric side effects.

The substituted spiro compounds disclosed herein selectively inhibit cyclooxygenase II over cyclooxygenase I and relieve the effects of inflammation. These compounds, in addition, do not display substantial inhibition of cyclooxygenase I and produce a reduced amount of side effects.

Diarylcycloalkenes have been made and used for a variety of utilities. For example, Offenlegungsschrift 4,212,628, published Oct. 21, 1993, describes 1,2-bis(4-alkylphenyl)cyclohex-1-ene compounds as having antitumor activity. 2,3-Bis-(4-hydroxyphenyl)-2-cyclopenten-1-one has been identified from the knot resin powder of Arqaucaria angustifolia [H. Ohash, et al., *Phytochemistry*, 31, 1371–73 (1992)].

Substituted 1,2-diphenylcyclopentenes have been synthesized for use in studies of their rotational behavior, and specifically, 1-(2,4-dimethylphenyl)-2-phenylcyclopentene [D. Y. Curtin, et al., *J. Org. Chem.*, 36, 565–72 (1971)]. 1,2-Di-(2'-methoxyphenyl)-$\Delta^1$-cyclopentene has been identified as an impurity in the synthesis of cannabinoids [O. P. Malik, et al., *Ind. J. Chem.*, 14B, 975–78 (1976)].

1-(Substitutedphenyl)-2-phenylcyclopentenes have been synthesized to study their photochemical reactions into phenanthrene derivatives. Compounds with meta substituents, such as 1-(3-chlorophenyl)-2-phenylcyclopentene, are described in Somers, et al., *J. Photochem. Photobiol.*, 48A, 353–74 (1989). Para substituents, including specifically 1-(4-fluorophenyl)-2-phenylcyclopentene, are described in Laarhoven, *Pure & Appl. Chem.*, 56, 1225–40 (1984).

U.S. Pat. No. 3,214,470 to Grogan describes aminospiroalkanes as having anesthetic properties.

The synthesis of 7,8-diphenyl-1,4-dioxaspiro[4.4]non-7-ene is described as an intermediate for forming 1,5-diphenylbicyclo[3.1.0]hexan-3-ol [E. J. Corey, et al., *J. Amer. Chem. Soc.*, 85, 1788–1792 (1963)]. U.S. Pat. No. 3,728,404 to Kubicek describes a method to make spiro compounds, and specifically 1,1-dichloro-2,2,5-triphenylspiro[2.4]hept-5-ene.

DESCRIPTION OF THE INVENTION

A class of substituted spiro compounds useful in treating inflammation-related disorders is defined by Formula I:

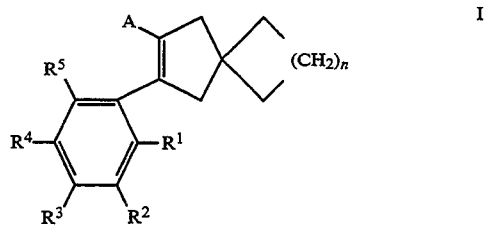

wherein A is selected from

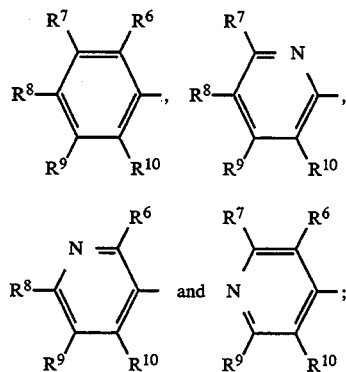

wherein each of $R^1$ through $R^{10}$ is independently selected from hydrido, halo, alkyl, haloalkoxy, alkoxy, alkylthio, cyano, haloalkyl, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erythematosus, osteoarthritis and juvenile arthritis. Such compounds of Formula I would be useful in the treatment of asthma, bronchitis, menstrual cramps, tendinitis, bursiris, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative coliris. Compounds of Formula I would be useful in treating inflammation in such diseases as vascular diseases, migraine headaches, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as antiinflammatory agents, such as for the treatment of arthritis, with the additional benefit of having significantly less harmful side effects.

The present invention also includes compounds which selectively inhibit cyclooxygenase II over cyclooxygenase I and do not significantly inhibit one or more other arachidonic pathway steps, such as thromboxane $B_2$ ($TXB_2$) production. Importantly, thromboxanes cause blood platelet aggregation and have vasoconstriction properties. Thus a lack of effect in the regulation of non-inflammation related thromboxane production is further evidence of the beneficial selectivity of the present compounds.

Preferably, the compounds of the present invention have a thromboxane $B_2$ inhibition $IC_{50}$ of greater than about 1.5 $\mu$M, as determined by a whole cell assay and preferably over 10 $\mu$M. The inhibition of the production of $TXB_2$ by a whole cell assay is a better indicator of potential in vivo behavior as the assay also incorporates such factors as cell transport.

More preferably, the compounds also have a selectivity ratio of cyclooxygenase II inhibition over cyclooxygenase I inhibition of at least 50, and preferably of at least 100. Even more preferably, the compounds have a cyclooxygenase I $IC_{50}$ of greater than about 0.5 $\mu$M, and more preferably of greater than 5 $\mu$M. Such preferred selectivity may indicate an ability to reduce the incidence of common NSAID-induced side effects, such as ulcers.

A preferred class of compounds consists of those compounds of Formula I wherein each of $R^1$, $R^2$, $R^4$ through $R^7$, $R^9$ and $R^{10}$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto; and wherein $R^3$ is selected from lower alkylsulfonyl, lower haloalkylsulfonyl and sulfamyl, and $R^8$, if present, is selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto; or wherein further, $R^3$ is selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto, and $R^8$ is selected from lower alkylsulfonyl, lower haloalkylsulfonyl and sulfamyl; or a pharmaceutically-acceptable salt thereof.

A class of compounds of particular interest consists of those compounds of Formula I wherein each of $R^1$, $R^2$, $R^4$ through $R^7$, $R^9$ and $R^{10}$ is independently selected from hydrido, fluoro, chloro, bromo, iodo, methyl, ethyl, n-propyl, isopropyl, butyl, tert-butyl, isobutyl, methoxy, trifluoromethoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is selected from fluoromethylsulfonyl, difluoromethylsulfonyl, trifluoromethylsulfonyl, methylsulfonyl and sulfamyl, and $R^8$, if present, is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; or wherein further $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl, and $R^8$ is selected from fluoromethylsulfonyl, difluoromethylsulfonyl, trifluoromethylsulfonyl, methylsulfonyl and sulfamyl; or a pharmaceutically-acceptable salt thereof.

Within Formula I there is a subclass of compounds of high interest represented by Formula II:

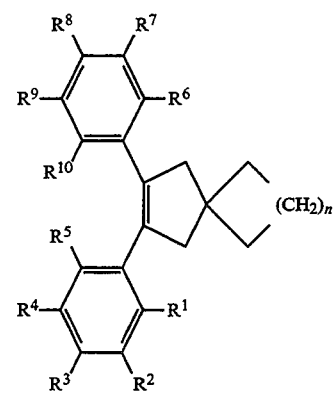

wherein each of $R^1$ through $R^{10}$ is independently selected from hydrido, halo, alkyl, haloalkoxy, alkoxy, alkylthio, cyano, haloalkyl, hydroxyalkyl, alkoxyalkyl, hydroxyl, mercapto, haloalkylsulfonyl, alkylsulfonyl and sulfamyl; and wherein n is a number selected from 0, 1, 2 and 3; or a pharmaceutically-acceptable salt thereof.

A preferred class of compounds consists of those compounds of Formula II wherein n is a number selected from 0, 1 and 2; wherein each of $R^1$, $R^2$ and $R^4$ through $R^{10}$ is independently selected from hydrido, halo, lower alkyl, lower alkylthio, cyano, lower haloalkyl, lower haloalkoxy, lower alkoxy, hydroxyl, mercapto, lower hydroxyalkyl and lower alkoxyalkyl; and wherein $R^3$ is selected from lower alkylsulfonyl, lower haloalkylsulfonyl and sulfamyl; or a pharmaceutically-acceptable salt thereof.

A class of compounds of particular interest consists of those compounds of Formula II wherein each of $R^1$, $R^2$ and $R^4$ through $R^{10}$ is independently selected from hydrido, fluoro, chloro, bromo, iodo, methyl, ethyl, n-propyl, isopropyl, butyl, tert-butyl, isobutyl, trifluoromethoxy, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is selected from fluoromethylsulfonyl, difluoromethylsulfonyl, trifluoromethylsulfonyl, methylsulfonyl and sulfamyl; or a pharmaceutically-acceptable salt thereof.

A family of specific compounds of particular interest within Formula II consists of compounds and pharmaceutically-acceptable salts thereof as follows:

5-phenyl-6-[4-(methylsulfonyl)phenyl]spiro[2.4]hept-5-ene;
5-(4-fluorophenyl)-6-[4-(methylsulfonyl)phenyl]spiro[2.4]hept-5-ene;
5-(4-chlorophenyl)-6-[4-(methylsulfonyl)phenyl]spiro[2.4]hept-5-ene;
5-(4-bromophenyl)-6-[4-(methylsulfonyl)phenyl]spiro[2.4]hept-5-ene;
5-(4-iodophenyl)-6-[4-(methylsulfonyl)phenyl]spiro[2.4]hept-5-ene;
5-(4-methylphenyl)-6-[4-(methylsulfonyl)phenyl]spiro[2.4]hept-5-ene;
5-(4-ethylphenyl)-6-[4-(methylsulfonyl)phenyl]spiro[2.4]hept-5-ene;
5-(4-methoxyphenyl)-6-[4-(methylsulfonyl)phenyl]spiro[2.4]hept-5-ene;
5-(4-methylthiophenyl)-6-[4-(methylsulfonyl)phenyl]spiro[2.4]hept-5-ene;
5-(4-cyanophenyl)-6-[4-(methylsulfonyl)phenyl]spiro[2.4]hept-5-ene;
5-(4-trifluoromethylphenyl)-6-[4-(methylsulfonyl)phenyl]spiro[2.4]hept-5-ene;
5-(4-hydroxymethylphenyl)-6-[4-(methylsulfonyl)phenyl]spiro[2.4]hept-5-ene;
5-(4-methoxymethylphenyl)-6-[4-(methylsulfonyl)phenyl]spiro[2.4]hept-5-ene;
5-(4-hydroxyphenyl)-6-[4-(methylsulfonyl)phenyl]spiro[2.4]hept-5-ene;
5-(4-mercaptophenyl)-6-[4-(methylsulfonyl)phenyl]spiro[2.4]hept-5-ene;
4-(6-phenylspiro[2.4]hept-5-en-5-yl)benzenesulfonamide;
4-[6-(4-fluorophenyl)spiro[2.4]hept-5-en-5-yl]benzenesulfonamide;
4-[6-(4-chlorophenyl)spiro[2.4]hept-5-en-5-yl]benzenesulfonamide;
4-[6-(4-bromophenyl)spiro[2.4]hept-5-en-5-yl]benzenesulfonamide;
4-[6-(4-iodophenyl)spiro[2.4]hept-5-en-5-yl]benzenesulfonamide;
4-[6-(4-methylphenyl)spiro[2.4]hept-5-en-5-yl]benzenesulfonamide;
4-[6-(4-ethylphenyl)spiro[2.4]hept-5-en-5-yl]benzenesulfonamide;
4-[6-(4-methoxyphenyl)spiro[2.4]hept-5-en-5-yl]benzenesulfonamide;
4-[6-(4-methylthiophenyl)spiro[2.4]hept-5-en-5-yl]benzenesulfonamide;
4-[6-(4-cyanophenyl)spiro[2.4]hept-5-en-5-yl]benzenesulfonamide;
4-[6-(4-trifluoromethylphenyl)spiro[2.4]hept-5-en-5-yl]benzenesulfonamide;
4-[6-(4-hydroxymethylphenyl)spiro[2.4]hept-5-en-5-yl]benzenesulfonamide;
4-[6-(4-methoxymethylphenyl)spiro[2.4]hept-5-en-5-yl]benzenesulfonamide;
4-[6-(4-hydroxyphenyl)spiro[2.4]hept-5-en-5-yl]benzenesulfonamide;
4-[6-(4-mercaptophenyl)spiro[2.4]hept-5-en-5-yl]benzenesulfonamide;
6-phenyl-7-[4-(methylsulfonyl)phenyl]spiro[3.4]oct-6-ene;
6-(4-fluorophenyl)-7-[4-(methylsulfonyl)phenyl]spiro[3.4]oct-6-ene;
6-(4-chlorophenyl)-7-[4-(methylsulfonyl)phenyl]spiro[3.4]oct-6-ene;
6-(4-bromophenyl)-7-[4-(methylsulfonyl)phenyl]spiro[3.4]oct-6-ene;
6-(4-iodophenyl)-7-[4-(methylsulfonyl)phenyl]spiro[3.4]oct-6-ene;
6-(4-methylphenyl)-7-[4-(methylsulfonyl)phenyl]spiro[3.4]oct-6-ene;
6-(4-ethylphenyl)-7-[4-(methylsulfonyl)phenyl]spiro[3.4]oct-6-ene;
6-(4-methoxyphenyl)-7-[4-(methylsulfonyl)phenyl]spiro[3.4]oct-6-ene;
6-(4-methylthiophenyl)-7-[4-(methylsulfonyl)phenyl]spiro[3.4]oct-6-ene;
6-(4-cyanophenyl)-7-[4-(methylsulfonyl)phenyl]spiro[3.4]oct-6-ene;
6-(4-trifluoromethylphenyl)-7-[4-(methylsulfonyl)phenyl]spiro[3.4]oct-6-ene;
6-(4-hydroxymethylphenyl)-7-[4-(methylsulfonyl)phenyl]spiro[3.4]oct-6-ene;
6-(4-methoxymethylphenyl)-7-[4-(methylsulfonyl)phenyl]spiro[3.4]oct-6-ene;
6-(4-hydroxyphenyl)-7-[4-(methylsulfonyl)phenyl]spiro[3.4]oct-6-ene;
6-(4-mercaptophenyl)-7-[4-(methylsulfonyl)phenyl]spiro[3.4]oct-6-ene;
4-(7-phenylspiro[3.4]oct-6-en-6-yl)benzenesulfonamide;
4-[7-(4-fluorophenyl)spiro[3.4]oct-6-en-6-yl]benzenesulfonamide;
4-[7-(4-chlorophenyl)spiro[3.4]oct-6-en-6-yl]benzenesulfonamide;
4-[7-(4-bromophenyl)spiro[3.4]oct-6-en-6-yl]benzenesulfonamide;
4-[7-(4-iodophenyl)spiro[3.4]oct-6-en-6-yl]benzenesulfonamide;
4-[7-(4-methylphenyl)spiro[3.4]oct-6-en-6-yl]benzenesulfonamide;
4-[7-(4-ethylphenyl)spiro[3.4]oct-6-en-6-yl]benzenesulfonamide;
4-[7-(4-methoxyphenyl)spiro[3.4]oct-6-en-6-yl]benzenesulfonamide;
4-[7(4-methylthiophenyl)spiro[3.4]oct-6-en-6-yl]benzenesulfonamide;
4-[7-(4-cyanophenyl)spiro[3.4]oct-6-en-6-yl]benzenesulfonamide;

4-[7-(4-trifluoromethylphenyl)spiro[3.4]oct-6-en-6yl]-benzenesulfonamide;
4-[7-(4-hydroxymethylphenyl)spiro[3.4]oct-6-en-6-yl]benzenesulfonamide;
4-[7-(4-methoxymethylphenyl)spiro[3.4]oct-6-en-6-yl]benzenesulfonamide;
4-[7(4-hydroxyphenyl)spiro[3.4]oct -6-en-6-yl]benzenesulfonamide;
4-[7(4-mercaptophenyl)spiro[3.4]oct -6-en-6-yl]benzenesulfonamide;
2-phenyl-3-[4-(methylsulfonyl)phenyl]spiro[4.4]non-2-ene;
2-(4-fluorophenyl)-3-[4-(methylsulfonyl)phenyl]-spiro[4.4]non-2-ene;
2-(4-chlorophenyl)-3-[4-(methylsulfonyl)phenyl]-spiro[4.4]non-2-ene;
2-(4-bromophenyl)-3-[4-(methylsulfonyl)phenyl]-spiro[4.4]non-2-ene;
2-(4-iodophenyl)-3-[4-(methylsulfonyl)phenyl]-spiro[4.4]non-2-ene;
2-(4-methylphenyl)-3-[4-(methylsulfonyl)phenyl]-spiro[4.4]non-2-ene;
2-(4-ethylphenyl)-3-[4-(methylsulfonyl)phenyl]-spiro[4.4]non-2-ene;
2-(4-methoxyphenyl)-3-[4-(methylsulfonyl)phenyl]-spiro[4.4]non-2-ene;
2-(4-methylthiophenyl)-3-[4-(methylsulfonyl)phenyl]-spiro[4.4]non-2-ene;
2-(4-cyanophenyl)-3-[4-(methylsulfonyl)phenyl]-spiro[4.4]non-2-ene;
2-(4-trifluoromethylphenyl)-3-[4-(methylsulfonyl)phenyl]spiro[4.4]non-2-ene;
2-(4-hydroxymethylphenyl)-3-[4-(methylsulfonyl)phenyl]spiro[4.4]non-2-ene;
2-(4-methoxymethylphenyl)-3-[4-(methylsulfonyl)phenyl]spiro[4.4]non-2-ene;
2-(4-hydroxyphenyl)-3-[4-(methylsulfonyl)phenyl]-spiro[4.4]non-2-ene;
2-(4-mercaptophenyl)-3-[4-(methylsulfonyl)phenyl]-spiro[4.4]non-2-ene;
4-(3-phenylspiro[4.4]non-2-en-2-yl)benzenesulfonamide;
4-[3-(4-fluorophenyl)spiro[4.4]non-2-en-2-yl]benzenesulfonamide;
4-[3-(4-chlorophenyl)spiro[4.4]non-2-en-2-yl]benzenesulfonamide;
4-[3-(4-bromophenyl)spiro[4.4]non-2-en-2-yl]benzenesulfonamide;
4-[3(4-iodophenyl)spiro[4.4]non-2-en-2-yl]benzenesulfonamide;
4-[3-(4-methylphenyl)spiro[4.4]non-2-en-2-yl]benzenesulfonamide;
4-[3-(4-ethylphenyl)spiro[4.4]non-2-en-2-yl]benzenesulfonamide;
4-[3-(4-methoxyphenyl)spiro[4.4]non-2-en-2-yl]benzenesulfonamide;
4-[3-(4-methylthiophenyl)spiro[4.4]non-2-en-2-yl]benzenesulfonamide;
4-[3(4-cyanophenyl)spiro[4.4]non-2-en-2-yl]benzenesulfonamide;
4-[3-(4-trifluoromethylphenyl)spiro[4.4]non-2-en-2yl]benzenesulfonamide;
4-[3(4-hydroxymethylphenyl)spiro[4.4]non-2-en-2-yl]benzenesulfonamide;
4-[3(4-methoxymethylphenyl)spiro[4.4]non-2-en-2-yl]benzenesulfonamide;
4-[3-(4-hydroxyphenyl)spiro[4.4]non-2-en-2-yl]benzenesulfonamide;
4-[3(4-mercaptophenyl)spiro[4.4]non-2-en-2-yl]benzenesulfonamide;
5-(3-trifluoromethyl-4-methylphenyl)-6-[4-(methylsulfonyl)phenyl]spiro[2.4]hept-5-ene;
5-(3-trifluoromethyl-4-fluorophenyl)-6-[4-(methylsulfonyl)phenyl]spiro[2.4]hept-5-ene;
5-(3-trifluoromethyl-4-chlorophenyl)-6-[4-(methylsulfonyl)phenyl]spiro[2.4]hept-5-ene;
5-(3-trifluoromethyl-4-bromophenyl)-6-[4-(methylsulfonyl)phenyl]spiro[2.4]hept-5-ene;
5-(3-methyl-4-fluorophenyl)-6-[4-(methylsulfonyl)phenyl]spiro[2.4]hept-5-ene;
5-(3-methyl-4-chlorophenyl)-6-[4-(methylsulfonyl)phenyl]spiro[2.4]hept-5-ene;
5-(3-methyl-4-bromophenyl)-6-[4-(methylsulfonyl)phenyl]spiro[2.4]hept-5-ene;
5-(3-methyl-4-trifluorophenyl)-6-[4-(methylsulfonyl)phenyl]spiro[2.4]hept-5-ene;
5-(3-trifluoromethyl-4-methoxyphenyl)-6-[4-(methylsulfonyl)phenyl]spiro[2.4]hept-5-ene;
5-(3-methyl-4-methoxyphenyl)-6-[4-(methylsulfonyl)phenyl]spiro[2.4]hept-5-ene;
5-(3-fluoro-4-methoxyphenyl)-6-[4-(methylsulfonyl)phenyl]spiro[2.4]hept-5-ene;
5-(3-chloro -4-methoxyphenyl)-6-[4-(methylsulfonyl)phenyl]spiro[2.4]hept-5-ene;
5-(3-bromo -4-methoxyphenyl)-6-[4-(methylsulfonyl)phenyl]spiro[2.4]hept-5-ene;
5-(2,3,4,5,6-pentafluorophenyl)-6-[4-(methylsulfonyl)phenyl]spiro[2.4]hept-5-ene;
5-(4-methoxy-2,3,5,6-tetrafluorophenyl)-6-[4-(methylsulfonyl)phenyl]spiro[2.4]hept-5-ene;
5-(2,3,5,6-tetrafluoro-4-trifluoromethylphenyl)-6-[4-(methylsulfonyl)phenyl]spiro[2.4]hept -5-ene;
5-(3,5-difluoro -4-methoxyphenyl)-6-[4-(methylsulfonyl)phenyl]spiro[2.4]hept-5-ene;
5-(3,5-dichloro-4-methyoxyphenyl)-6-[4-(methylsulfonyl)phenyl]spiro[2.4 ]hept-5-ene;
5-(3,5-dibromo-4-methoxyphenyl)-6-[4-(methylsulfonyl)phenyl]spiro[2.4]hept-5-ene;
5-(2,3,4-trifluoro-4-methoxyphenyl)-6-[4-(methylsulfonyl)phenyl]spiro[2.4]hept-5-ene;
5-(2,3,4-trichloro-4-methoxyphenyl)-6-[4-(methylsulfonyl)phenyl]spiro[2.4]hept-5-ene;
5-(2,3,4-tribromo -4-methoxyphenyl)-6-[4-(methylsulfonyl)phenyl]spiro[2.4]hept-5-ene;
5-(2,4,5-trifluoro-4-methoxyphenyl)-6-[4-(methylsulfonyl)phenyl]spiro[2.4]hept-5-ene;
5-(2,4,5-trichloro-4-methoxyphenyl)-6-[4-(methylsulfonyl)phenyl]spiro[2.4]hept-5-ene;
5-(2,4,5-tribromo-4-methoxyphenyl)-6-[4-(methylsulfonyl)phenyl]spiro[2.4]hept-5-ene;
5-(3,4-dimethoxypheny 1)-6-[4-(methylsulfonyl)phenyl]spiro[2.4]hept-5-ene;
5-(3,4,5-trimethoxyphenyl)-6-[4-(methylsulfonyl)phenyl]spiro[2.4]hept-5-ene;
5-[3,4-bis(trifluoromethyl)phenyl]-6-[4-(methylsulfonyl)phenyl]spiro[2.4]hept-5-ene;
5-(3,4-dimethylphenyl)-6-[4-(methylsulfonyl)phenyl]-spiro[2.4]hept-5-ene;
5-(3,4-difluorophenyl)-6-[4-(methylsulfonyl)phenyl]-spiro[2.4]hept-5-ene;
5-(3,4-dichlorophenyl)-6-[4-(methylsulfonyl)phenyl]-spiro[2.4]hept-5-ene;
5-(3,4-dibromophenyl)-6-[4-(methylsulfonyl)phenyl]-spiro[2.4]hept-5-ene;
5-(3-chloro-4-fluorophenyl)-6-[4-(methylsulfonyl)phenyl]spiro[2.4]hept-5-ene;

5-(3-chloro-4-bromophenyl)-6-[4-(methylsulfonyl)-phenyl]spiro[2.4]hept-5-ene;
5-(4-chloro-3-fluorophenyl)-6-[4-(methylsulfonyl)-phenyl]spiro[2.4]hept-5-ene;
5-(4-chloro-3-bromophenyl)-6-[4-(methylsulfonyl)-phenyl]spiro[2.4]hept-5-ene;
5-(3-trifluoromethyl-4-methylphenyl)-6-[4-(fluoromethylsulfonyl)phenyl]spiro[2.4]hept-5-ene;
5-(3-trifluoromethyl-4-fluorophenyl)-6-[4-(fluoromethylsulfonyl)phenyl]spiro[2.4]hept-5-ene;
5-(3-trifluoromethyl-4-chlorophenyl)-6-[4-(fluoromethylsulfonyl)phenyl]spiro[2.4]hept-5-ene;
5(3-trifluoromethyl-4-bromophenyl)-6-[4-(fluoromethylsulfonyl)phenyl]spiro[2.4]hept -5-ene;
5-(3-methyl-4-fluorophenyl)-6-[4-(fluoromethylsulfonyl)phenyl]spiro[2.4]hept-5-ene;
5-(3-methyl-4-chlorophenyl)-6-[4-(fluoromethylsulfonyl)phenyl]spiro[2.4]hept-5-ene;
5-(3-methyl-4-bromophenyl)-6-[4 -(fluoromethylsulfonyl)phenyl]spiro[2.4]hept-5-ene;
5-(3-methyl-4-trifluorophenyl)-6-[4-(fluoromethylsulfonyl)phenyl]spiro[2.4]hept-5-ene;
5-(3-trifluoromethyl-4-methoxyphenyl)-6-[4-(fluoromethylsulfonyl)phenyl]spiro[2.4]hept-5-ene;
5-(3-methyl-4-methoxyphenyl)-6-[4-(fluoromethylsulfonyl)phenyl]spiro[2.4]hept-5-ene;
5-(3-fluoro-4-methoxyphenyl)-6-[4-(fluoromethylsulfonyl)phenyl]spiro[2.4]hept-5-ene;
5-(3-chloro-4-methoxyphenyl)-6-[4-(fluoromethylsulfonyl)phenyl]spiro[2.4]hept-5-ene;
5-(3-bromo-4-methoxyphenyl)-6-[4-(fluoromethylsulfonyl)phenyl]spiro[2.4]hept-5-ene;
5-(2,3,4,5,6-pentafluorophenyl)-6-[4-(fluoromethylsulfonyl)phenyl]spiro[2.4]hept-5-ene;
5-(4-methoxy-2,3,5,6-tetrafluorophenyl)-6-[4-(fluoromethylsulfonyl)phenyl]spiro[2.4]hept -5-ene;
5-(2,3,5,6-tetrafluoro-4-trifluoromethylphenyl)-6-[4-(fluoromethylsulfonyl)phenyl]spiro[2.4]hept-5-ene;
5-(3,5-difluoro-4-methoxyphenyl)-6-[4-(fluoromethylsulfonyl)phenyl]spiro[2.4]hept-5-ene;
5-(3,5-dichloro-4-methyoxyphenyl)-6-[4-(fluoromethylsulfonyl)phenyl]spiro[2.4]hept-5-ene;
5-(3,5-dibromo-4-methoxyphenyl)-6-[4-(fluoromethylsulfonyl)phenyl]spiro[2.4]hept-5-ene;
5-(2,3,4-trifluoro-4-methoxyphenyl)-6-[4-(fluoromethylsulfonyl)phenyl]spiro[2.4]hept-5-ene;
5-(2,3,4-trichloro-4-methyoxyphenyl)-6-[4-(fluoromethylsulfonyl)phenyl]spiro[2.4]hept-5-ene;
5-(2,3,4-tribromo-4-methyoxyphenyl)-6-[4-(fluoromethylsulfonyl)phenyl]spiro[2.4]hept-5-ene;
-(2,4,5-trifluoro-4-methoxyphenyl)-6-[4-(fluoromethylsulfonyl)phenyl]spiro[2.4]hept-5-ene;
5-(2,4,5-trichloro-4-methyoxyphenyl)-6-[4-(fluoromethylsulfonyl)phenyl]spiro[2.4]hept-5-ene;
5-(2,4,5-tribromo-4-methyoxyphenyl)-6-[4-(fluoromethylsulfonyl)phenyl]spiro[2.4]hept-5-ene;
5-(3,4-dimethoxyphenyl)-6-[4-(fluoromethylsulfonyl)phenyl]spiro[2.4]hept-5-ene;
5-(3,4,5-trimethoxyphenyl)-6-[4-(fluoromethylsulfonyl)phenyl]spiro[2.4]hept-5-ene;
5-[3,4-bis(trifluoromethyl)phenyl]-6-[4-(fluoromethylsulfonyl)phenyl]spiro[2.4]hept-5-ene;
5-(3,4-dimethylphenyl)-6-[4-(fluoromethylsulfonyl)phenyl]spiro[2.4]hept-5-ene;
5-(3,4-difluorophenyl)-6-[4-(fluoromethylsulfonyl)phenyl]spiro[2.4]hept-5-ene;
5-(3,4-dichlorophenyl)-6-[4-(fluoromethylsulfonyl)phenyl]spiro[2.4]hept-5-ene;
5-(3,4-dibromophenyl)-6-[4-(fluoromethylsulfonyl)phenyl]spiro[2.4]hept-5-ene;
5-(3-chloro-4-fluorophenyl)-6-[4-(fluoromethylsulfonyl)phenyl]spiro[2.4]hept-5-ene;
5-(3-chloro-4-bromophenyl)-6-[4-(fluoromethylsulfonyl)phenyl]spiro[2.4]hept-5-ene;
5-(4-chloro-3-fluorophenyl)-6-[4-(fluoromethylsulfonyl)phenyl]spiro[2.4]hept-5-ene;
5-(4-chloro-3-bromophenyl)-6-[4-(fluoromethylsulfonyl)phenyl]spiro[2.4]hept-5-ene;
5-(3-trifluoromethyl-4-methylphenyl)-6-[4-(difluoromethylsulfonyl)phenyl]spiro[2.4]hept-5-ene;
5-(3-trifluoromethyl-4-fluorophenyl)-6-[4-(difluoromethylsulfonyl)phenyl]spiro[2.4]hept-5-ene;
5-(3-trifluoromethyl-4-chlorophenyl)-6-[4-(difluoromethylsulfonyl)phenyl]spiro[2.4]hept-5-ene;
5-(3-trifluoromethyl-4-bromophenyl)-6-[4-(difluoromethylsulfonyl)phenyl]spiro[2.4]hept-5-ene;
5-(3-methyl -4-fluorophenyl)-6-[4-(difluoromethylsulfonyl)phenyl]spiro[2.4]hept-5-ene;
5-(3-methyl-4-chlorophenyl)-6-[4-(difluoromethylsulfonyl)phenyl]spiro[2.4]hept-5-ene;
5-(3-methyl-4-bromophenyl)-6-[4-(difluoromethylsulfonyl)phenyl]spiro[2.4]hept-5-ene;
5-(3-methyl-4-trifluorophenyl)-6-[4-(difluoromethylsulfonyl)phenyl]spiro[2.4]hept-5-ene;
5-(3-trifluoromethyl -4-methoxyphenyl)-6-[4-(difluoromethylsulfonyl)phenyl]spiro[2.4]hept -5-ene;
5-(3-methyl-4-methoxyphenyl)-6-[4-(difluoromethylsulfonyl)phenyl]spiro[2.4]hept-5-ene;
5-(3-fluoro-4-methoxyphenyl)-6-[4-(difluoromethylsulfonyl)phenyl]spiro[2.4]hept-5-ene;
5-(3-chloro-4-methoxyphenyl)-6-[4-(difluoromethylsulfonyl)phenyl]spiro[2.4]hept-5-ene;
5-(3-bromo-4-methoxyphenyl)-6-[4-(difluoromethylsulfonyl)phenyl]spiro[2.4]hept-5-ene;
5-(2,3,4,5,6-pentafluorophenyl)-6-[4-(difluoromethylsulfonyl)phenyl]spiro[2.4]hept-5-ene;
5-(4-methoxy-2,3,5,6-tetrafluorophenyl)-6-[4-(difluoromethylsulfonyl)phenyl]spiro[2.4]hept -5-ene;
5-(2,3,5,6-tetrafluoro-4-trifluoromethylphenyl)-6-[4-(difluoromethylsulfonyl)phenyl]spiro[2.4]hept-5-ene;
5-(3,5-difluoro-4-methoxyphenyl)-6-[4-(difluoromethylsulfonyl)phenyl]spiro[2.4]hept-5-ene;
5-(3,5-dichloro-4-methyoxyphenyl)-6-[4-(difluoromethylsulfonyl)phenyl]spiro[2.4]hept-5-ene;
5-(3,5-dibromo-4-methoxyphenyl)-6-[4-(difluoromethylsulfonyl)phenyl]spiro[2.4]hept-5-ene;
5-(2,3,4-trifluoro-4-methoxyphenyl)-6-[4-(difluoromethylsulfonyl)phenyl]spiro[2.4]hept-5-ene;
5-(2,3,4-trichloro-4-methyoxyphenyl)-6-[4-(difluoromethylsulfonyl)phenyl]spiro[2.4]hept-5-ene;
5-(2,3,4-tribromo-4-methyoxyphenyl)-6-[4-(difluoromethylsulfonyl)phenyl]spiro[2.4]hept-5-ene;
5-(2,4,5-trifluoro-4-methoxyphenyl)-6-[4-(difluoromethylsulonyl)phenyl]spiro[2.4]hept-5-ene;
5-(2,4,5-trichloro-4-methyoxyphenyl)-6-[4-(difluoromethylsulfonyl)phenyl]spiro[2.4]hept -5-ene;
5-(2,4,5-tribromo-4-methyoxyphenyl)-6-[4-(difluoromethylsulfonyl)phenyl]spiro[2.4]hept-5-ene;
5-(3,4-dimethoxyphenyl)-6-[4-(difluoromethylsulfonyl)phenyl]spiro[2.4]hept-5-ene;
5-(3,4,5-trimethoxyphenyl)-6-[4-(difluoromethylsulfonyl)phenyl]spiro[2.4]hept-5-ene;
5-[3,4-bis(trifluoromethyl)phenyl]-6-[4-(difluoromethylsulfonyl)phenyl]spiro[2.4]hept-5-ene;
5-(3,4-dimethylphenyl)-6-[4-(difluoromethylsulfonyl)phenyl]spiro[2.4]hept-5-ene;

5-(3,4-difluorophenyl)-6-[4-(difluoromethylsulfonyl)-phenyl]spiro[2.4]hept-5-ene;
5-(3,4-dichlorophenyl)-6-[4-(difluoromethylsulfonyl)-phenyl]spiro[2.4]hept-5-ene;
5-(3,4-dibromophenyl)-6-[4-(difluoromethylsulfonyl)-phenyl]spiro[2.4]hept-5-ene;
5-(3-chloro-4-fluorophenyl)-6-[4-(difluoromethylsulfonyl)phenyl]spiro[2.4]hept-5-ene;
5-(3-chloro-4-bromophenyl)-6-[4-(difluoromethylsulfonyl)phenyl]spiro[2.4]hept-5-ene;
5-(4-chloro-3-fluorophenyl)-6-[4-(difluoromethylsulfonyl)phenyl]spiro[2.4]hept-5-ene;
5-(4-chloro-3-bromophenyl)-6-[4-(difluoromethylsulfonyl)phenyl]spiro[2.4]hept-5-ene;
5-(3-trifluoromethyl-4-methylphenyl)-6-[4-(trifluoromethylsulfonyl)phenyl]spiro[2.4]hept-5-ene;
5-(3-trifluoromethyl-4-fluorophenyl)-6-[4-(trifluoromethylsulfonyl)phenyl]spiro[2.4]hept-5-ene;
5-(3-trifluoromethyl-4-chlorophenyl)-6-[4-(trifluoromethylsulfonyl)phenyl]spiro[2.4]hept-5-ene;
5-(3-trifluoromethyl-4-bromophenyl)-6-[4-(trifluoromethylsulfonyl)phenyl]spiro[2.4]hept-5-ene;
5-(3-methyl-4-fluorophenyl)-6-[4-(trifluoromethylsulfonyl)phenyl]spiro[2.4]hept-5-ene;
5-(3-methyl-4-chlorophenyl)-6-[4-(trifluoromethylsulfonyl)phenyl]spiro[2.4]hept-5-ene;
5-(3-methyl-4-bromophenyl)-6-[4-(trifluoromethylsulfonyl)phenyl]spiro[2.4]hept-5-ene;
5-(3-methyl-4-trifluorophenyl)-6-[4-(trifluoromethylsulfonyl)phenyl]spiro[2.4]hept-5-ene;
5-(3-trifluoromethyl-4-methoxyphenyl)-6-[4-(trifluoromethylsulfonyl)phenyl]spiro[2.4]hept-5-ene;
5-(3-methyl-4-methoxyphenyl)-6-[4-(trifluoromethylsulfonyl)phenyl]spiro[2.4]hept-5-ene;
5-(3-fluoro-4-methoxyphenyl)-6-[4-(trifluoromethylsulfonyl)phenyl]spiro[2.4]hept-5-ene;
5-(3-chloro-4-methoxyphenyl)-6-[4-(trifluoromethylsulfonyl)phenyl]spiro[2.4]hept-5-ene;
5-(3-bromo-4-methoxyphenyl)-6-[4-(trifluoromethylsulfonyl)phenyl]spiro[2.4]hept-5-ene;
5-(2,3,4,5,6-pentafluorophenyl)-6-[4-(trifluoromethylsulfonyl)phenyl]spiro[2.4]hept-5-ene;
5-(4-methoxy-2,3,5,6-tetrafluorophenyl)-6-[4-(trifluoromethylsulfonyl)phenyl]spiro[2.4]hept-5-ene;
5-(2,3,5,6-tetrafluoro-4-trifluoromethylphenyl)-6-[4-(trifluoromethylsulfonyl)phenyl]spiro[2.4]hept-5-ene;
5-(3,5-difluoro-4-methoxyphenyl)-6-[4-(trifluoromethylsulfonyl)phenyl]spiro[2.4]hept-5-ene;
5-(3,5-dichloro-4-methyoxyphenyl)-6-[4-(trifluoromethylsulfonyl)phenyl]spiro[2.4]hept-5-ene;
5-(3,5-dibromo-4-methoxyphenyl)-6-[4-(trifluoromethylsulfonyl)phenyl]spiro[2.4]hept-5-ene;
5-(2,3,4-trifluoro-4-methoxyphenyl)-6-[4-(trifluoromethylsulfonyl)phenyl]spiro[2.4]hept-5ene;
5-(2,3,4-trichloro-4-methyoxyphenyl)-6-[4-(trifluoromethylsulfonyl)phenyl]spiro[2.4]hept-5-ene;
5-(2,3,4-tribromo-4-methyoxyphenyl)-6-[4-(trifluoromethylsulfonyl)phenyl]spiro[2.4]hept-5-ene;
5-(2,4,5-trifluoro-4-methoxyphenyl)-6-[4-(trifluoromethylsulfonyl)phenyl]spiro[2.4]hept-5-ene;
5-(2,4,5-trichloro-4-methyoxyphenyl)-6-[4-(trifluoromethylsulfonyl)phenyl]spiro[2.4]hept-5ene;
5-(2,4,5-tribromo-4-methyoxyphenyl)-6-[4-(trifluoromethylsulfonyl)phenyl]spiro[2.4]hept-5-ene;
5-(3,4-dimethoxyphenyl)-6-[4-(trifluoromethylsulfonyl)phenyl]spiro[2.4]hept-5-ene;
5-(3,4,5-trimethoxyphenyl)-6-[4-(trifluoromethylsulfonyl)phenyl]spiro[2.4]hept-5-ene;
5-[3,4-bis(trifluoromethyl)phenyl]-6-[4-(trifluoromethylsulfonyl)phenyl]spiro[2.4]hept-5-ene;
5-(3,4-dimethylphenyl)-6-[4-(trifluoromethylsulfonyl)phenyl]spiro[2.4]hept-5-ene;
5-(3,4-difluorophenyl)-6-[4-(trifluoromethylsulfonyl)phenyl]spiro[2.4]hept-5-ene;
5-(3,4-dichlorophenyl)-6-[4-(trifluoromethylsulfonyl)phenyl]spiro[2.4]hept-5-ene;
5-(3,4-dibromophenyl)-6-[4-(trifluoromethylsulfonyl)phenyl]spiro[2.4]hept-5-ene;
5-(3-chloro-4-fluorophenyl)-6-[4-(trifluoromethylsulfonyl)phenyl]spiro[2.4]hept-5-ene;
5-(3-chloro-4-bromophenyl)-6-[4-(trifluoromethylsulfonyl)phenyl]spiro[2.4]hept-5-ene;
5-(4-chloro-3-fluorophenyl)-6-[4-(trifluoromethylsulfonyl)phenyl]spiro[2.4]hept-5-ene;
5-(4-chloro-3-bromophenyl)-6-[4-(trifluoromethylsulfonyl)phenyl]spiro[2.4]hept-5-ene;
4-[6-(3-methyl-4-fluorophenyl)spiro[2.4]hept-5-en-5-yl]benzenesulfonamide;
4-[6-(3-methyl-4-chlorophenyl)spiro[2.4]hept-5-en-5-yl]benzenesulfonamide;
4-[6-(3-methyl-4-bromophenyl)spiro[2.4]hept-5-en-5-yl]benzenesulfonamide;
4-[6-(3-methyl-4-trifluoromethylphenyl)spiro[2.4]hept-5-en-5-yl]benzenesulfonamide;
4-[6-(3-methyl-4-methoxyphenyl)spiro[2.4]hept-5-en-5-yl]benzenesulfonamide;
4-[6-(3-trifluoromethyl-4-fluorophenyl)spiro[2.4]hept-5-en-5-yl]benzenesulfonamide;
4-[6-(3-trifluoromethyl-4-chlorophenyl)spiro[2.4]hept-5-en-5-yl]benzenesulfonamide;
4-[6-(3-trifluoromethyl-4-bromophenyl)spiro[2.4]hept-5-en-5-yl]benzenesulfonamide;
4-[6-(3-trifluoromethyl-4-methylphenyl)spiro[2.4]hept-5-en-5-yl]benzenesulfonamide;
4-[6-(3-trifluoromethyl-4-methoxyphenyl)spiro[2.4]hept-5-en-5-yl]benzenesulfonamide;
4-[6-(3-fluoro-4-methoxyphenyl)spiro[2.4]hept-5-en-5-yl]benzenesulfonamide;
4-[6-(3-chloro-4-methoxyphenyl)spiro[2.4]hept-5-en-5-yl]benzenesulfonamide;
4-[6-(3-bromo-4-methoxyphenyl)spiro[2.4]hept-5-en-5-yl]benzenesulfonamide;
4-[6-(2,3,4,5,6-pentafluorophenyl)spiro[2.4]hept-5-en-5-yl]benzenesulfonamide;
4-[6-(4-methoxy-2,3,5,6-tetrafluorophenyl)spiro[2.4]hept-5-en-5-yl]benzenesulfonamide;
4-[6-(2,3,5,6-tetrafluoro-4trifluoromethylphenyl)-spiro[2.4]hept-5-en-5yl]benzenesulfonamide;
4-[6-(3,5-difluoro-4-methoxyphenyl)spiro[2.4]hept-5-en-5-yl]benzenesulfonamide;
4-[6-(3,5-dichloro-4-methoxyphenyl)spiro[2.4]hept-5-en-5-yl]benzenesulfonamide;
4-[6-(3,5-dibromo-4-methoxyphenyl)spiro[2.4]hept-5-en-5-yl]benzenesulfonamide;
4-[6-(2,3,4-trifluoro-4-methoxyphenyl)spiro[2.4]hept-5-en-5-yl]benzenesulfonamide;
4-[6-(2,3,4-trichloro-4-methoxyphenyl)spiro[2.4]hept-5-en-5-yl]benzenesulfonamide;
4-[6-(2,3,4-tribromo-4-methoxyphenyl)spiro[2.4]hept-5-en-5-yl]benzenesulfonamide;
4-[6-(2,4,5-trifluoro-4-methoxyphenyl)spiro[2.4]hept-5-en-5-yl]benzenesulfonamide;
4-[6-(2,4,5-trichloro-4-methoxyphenyl)spiro[2.4]hept-5-en-5-yl]benzenesulfonamide;
4-[6-(2,4,5-tribromo-4-methoxyphenyl)spiro[2.4]hept-5-en-5-yl]benzenesulfonamide;

4-[6-(3,4-dimethoxyphenyl)spiro[2.4]hept-5-en-5-yl]benzenesulfonamide;
4-[6-(3,4,5-trimethoxyphenyl)spiro[2.4]hept-5-en-5-yl]benzenesulfonamide;
4-[6-[3,4-bis(trifluoromethyl)phenyl]spiro[2.4]hept-5-en-5-yl]benzenesulfonamide;
4-[6-(3,4-dimethylphenyl)spiro[2.4]hept-5-en-5-yl]benzenesulfonamide;
4-[6-(3,4-difluorophenyl)spiro[2.4]hept-5-en-5-yl]benzenesulfonamide;
4-[6-(3,4-dichlorophenyl)spiro[2.4]hept-5-en-5-yl]benzenesulfonamide;
4-[6-(3,4-dibromophenyl)spiro[2.4]hept-5-en-5-yl]benzenesulfonamide;
4-[6-(3-chloro-4-fluorophenyl)spiro[2.4]hept-5-en-5l-yl]benzenesulfonamide;
4-[6-(3-chloro-4-bromophenyl)spiro[2.4]hept-5-en-5-yl]benzenesulfonamide;
4-[6-(4-chloro-3-fluorophenyl)spiro[2.4]hept-5-en-5-yl]benzenesulfonamide;
4-[6-(4-chloro-3-bromophenyl)spiro[2.4]hept-5-en-5-yl]benzenesulfonamide;
4-[6-(3-methyl-4-fluorophenyl)spiro[2.4]hept-5-en-5-yl]benzenesulfonamide;
4-[6-(3-methyl-4-chlorophenyl)spiro[2.4]hept-5-en-5-yl]benzenesulfonamide;
4-[6-(3-methyl-4-bromophenyl)spiro[2.4]hept-5-en-5-yl]benzenesulfonamide;
4-[6-(3-methyl-4-trifluoromethylphenyl)spiro[2.4]hept-5-en-5-yl]benzenesulfonamide;
4-[6-(3-methyl-4-methoxyphenyl)spiro[2.4]hept-5-en-5-yl]benzenesulfonamide;
4-[6-(3-trifluoromethyl-4-fluorophenyl)spiro[2.4]hept-5-en-5-yl]benzenesulfonamide;
4-[6-(3-trifluoromethyl-4-chlorophenyl)spiro[2.4]hept-5-en-5-yl]benzenesulfonamide;
4-[6-(3-trifluoromethyl-4-bromophenyl)spiro[2.4]hept-5-en-5-yl]benzenesulfonamide;
4-[6-(3-trifluoromethyl-4-methylphenyl)spiro[2.4]hept-5-en-5-yl]benzenesulfonamide;
4-[6-(3-trifluoromethyl-4-methoxyphenyl)spiro[2.4]hept-5-en-5-yl]benzenesulfonamide;
4-[6-(3-fluoro-4-methoxyphenyl)spiro[2.4]hept-5-en-5-yl]benzenesulfonamide;
4-[6-(3-chloro-4-methoxyphenyl)spiro[2.4]hept-5-en-5-yl]benzenesulfonamide;
4-[6-(3-bromo-4-methoxyphenyl)spiro[2.4]hept-5-en-5-yl]benzenesulfonamide;
4-[6-(2,3,4,5,6-pentafluorophenyl)spiro[2.4]hept-5-en-5-yl]benzenesulfonamide;
4-[6-(4-methoxy-2,3,5,6-tetrafluorophenyl)spiro[2.4]hept-5-en-5-yl]benzenesulfonamide;
4-[6-(2,3,5,6-tetrafluoro-4trifluoromethylphenyl)spiro[2.4]hept-5-en-5-yl]benzenesulfonamide;
4-[6-(3,5-difluoro-4-methoxyphenyl)spiro[2.4]hept-5-en-5-yl]benzenesulfonamide;
4-[6-(3,5-dichloro-4-methoxyphenyl)spiro[2.4]hept-5-en-5-yl]benzenesulfonamide;
4-[6-(3,5-dibromo-4-methoxyphenyl)spiro[2.4]hept-5-en-5-yl]benzenesulfonamide;
4-[6-(2,3,4-trifluoro-4-methoxyphenyl)spiro[2.4]hept-5-en-5-yl]benzenesulfonamide;
4-[6-(2,3,4-trichloro-4-methoxyphenyl)spiro[2.4]hept-5-en-5-yl]benzenesulfonamide;
4-[6-(2,3,4-tribromo-4-methoxyphenyl)spiro[2.4]hept-5-en-5-yl]benzenesulfonamide;
4-[6-(2,4,5-trifluoro-4-methoxyphenyl)spiro[2.4]hept-5-en-5-yl]benzenesulfonamide;
4-[6-(2,4,5-trichloro-4-methoxyphenyl)spiro[2.4]hept-5-en-5-yl]benzenesulfonamide;
4-[6-(2,4,5-tribromo-4-methoxyphenyl)spiro[2.4]hept-5-en-5-yl]benzenesulfonamide;
4-[6-(3,4-dimethoxyphenyl)spiro[2.4]hept-5-en-5-yl]benzenesulfonamide;
4-[6-(3,4,5-trimethoxyphenyl)spiro[2.4]hept-5-en-5-yl]benzenesulfonamide;
4-[6-[3,4-bis(trifluoromethyl)phenyl]spiro[2.4]hept-5-en-5-yl]benzenesulfonamide;
4-[6-(3,4-dimethylphenyl)spiro[2.4]hept-5-en-5-yl]benzenesulfonamide;
4-[6-(3,4-difluorophenyl)spiro[2.4]hept-5-en-5-yl]benzenesulfonamide;
4-[6-(3,4-dichlorophenyl)spiro[2.4]hept-5-en-5-yl]benzenesulfonamide;
4-[6-(3,4-dibromophenyl)spiro[2.4]hept-5-en-5-yl]benzenesulfonamide;
4-[6-(3-chloro-4-fluorophenyl)spiro[2.4]hept-5-en-5-yl]benzenesulfonamide;
4-[6-(3-chloro-4-bromophenyl)spiro[2.4]hept-5-en-5-yl]benzenesulfonamide;
4-[6-(4-chloro-3-fluorophenyl)spiro[2.4]hept-5-en-5-yl]benzenesulfonamide; and
4-[6-(4-chloro-3-bromophenyl)spiro[2.4]hept-5-en-5-yl]benzenesulfonamide.

Within Formula I there is a second subclass of compounds of high interest represented by Formula III:

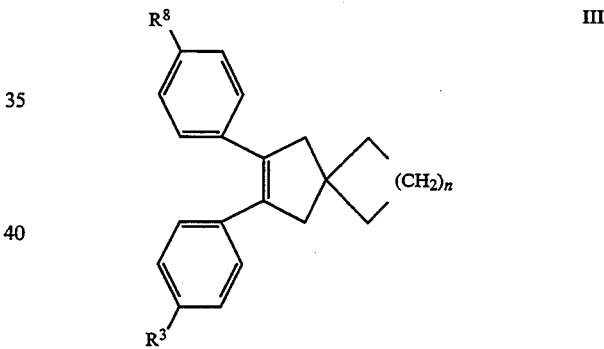

wherein n is a number selected from 0, 1 and 2;
wherein $R^3$ is selected from lower alkylsulfonyl and sulfamyl; and
wherein $R^8$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto; or a pharmaceutically-acceptable salt thereof.

A class of compounds of particular interest consists of those compounds of Formula III wherein $R^3$ is methylsulfonyl or sulfamyl; and wherein $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; or a pharmaceutically-acceptable salt thereof.

A family of specific compounds of particular interest within Formula III consists of compounds and pharmaceutically-acceptable salts thereof as follows:

5-(4-fluorophenyl)-6-[4-(methylsulfonyl)phenyl]-spiro[2.4]hept-5-ene;
4-[6-(4-fluorophenyl)spiro[2.4]hept-5-en-5-yl]benzenesulfonamide;
6-(4-fluorophenyl)-7-[4-(methylsulfonyl)phenyl]-spiro[3.4]oct-5-ene;
4-[7-(4-fluorophenyl)spiro[3.4]oct-6-en-6-yl]benzenesulfonamide; and
2-(4-fluorophenyl)-3-[4-(methylsulfonyl)phenyl]-spiro[4.4]non-5-ene.

Within Formula I there is a third subclass of compounds of high interest represented by Formula IV:

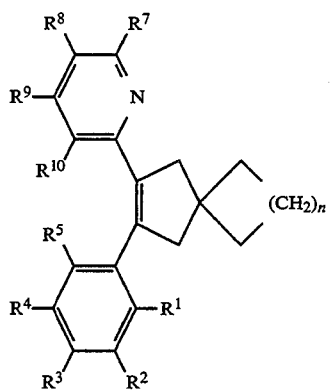

wherein n is a number selected from 0, 1, 2 and 3; and wherein each of $R^1$ through $R^5$ and $R^7$ through $R^{10}$ is independently selected from hydrido, halo, alkyl, alkoxy, alkylthio, cyano, haloalkyl, hydroxyalkyl, alkoxyalkyl, hydroxyl, mercapto, alkylsulfonyl and sulfamyl; or a pharmaceutically-acceptable salt thereof.

A preferred class of compounds consists of those compounds of Formula IV wherein n is a number selected from 0, 1 and 2; wherein each of $R^1$, $R^2$, $R^4$, $R^5$, $R^7$, $R^9$ and $R^{10}$ is independently selected from hydrido, halo, lower alkyl, lower alkoxy, lower alkylthio, cyano, lower haloalkyl, lower hydroxyalkyl, lower alkoxyalkyl, hydroxyl and mercapto; and wherein $R^3$ is selected from lower alkylsulfonyl and sulfamyl and $R^8$ is selected from hydrido, halo, lower alkyl, lower alkoxy, lower alkylthio, cyano and lower haloalkyl; or wherein further, $R^3$ is selected from hydrido, halo, lower alkyl, lower alkoxy, lower alkylthio, cyano and lower haloalkyl and $R^8$ is selected from lower alkylsulfonyl and sulfamyl; or a pharmaceutically-acceptable salt thereof.

A class of compounds of particular interest consists of those compounds of Formula IV wherein each of $R^1$, $R^2$, $R^4$, $R^5$, $R^7$, $R^9$ and $R^{10}$ is hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl, and $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; or wherein further, $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl, and $R^8$ is methylsulfonyl or sulfamyl; or a pharmaceutically-acceptable salt thereof.

A family of specific compounds of particular interest within Formula IV consists of compounds and pharmaceutically-acceptable salts thereof as follows:

2-[6-[4-(methylsulfonyl)phenyl]spiro[2.4]hept-5-en-5-yl]pyridine;
5-fluoro-2-[6-[4-(methylsulfonyl)phenyl]spiro[2.4]hept-5-en-5-yl]pyridine;
5-chloro-2-[6-[4-(methylsulfonyl)phenyl]spiro[2.4]hept-5-en-5-yl]pyridine;
5-methyl-2-[6-[4-(methylsulfonyl)phenyl]spiro[2.4]hept-5-en-5-yl]pyridine;
5-methoxy-2-[6-[4-(methylsulfonyl)phenyl]spiro[2.4]hept-5-en-5-yl]pyridine;
5-methylthio-2-[6-[4-(methylsulfonyl)phenyl]spiro[2.4]hept-5-en-5-yl]pyridine;
5-cyano-2-[6-[4-(methylsulfonyl)phenyl]spiro[2.4]hept-5-en-5-yl]pyridine;
5-trifluoromethyl-2-[6-[4-(methylsulfonyl)phenyl]spiro[2.4]hept-5-en-5-yl]pyridine;
4-[6-(pyridin-2-yl)spiro[2.4]hept-5-en-5-yl]benzenesulfonamide;
4-[6-(5-fluoropyridin-2-yl)spiro[2.4]hept-5-en-5-yl]benzenesulfonamide;
4-[6-(5-chloropyridin-2-yl)spiro[2.4]hept-5-en-5-yl]benzenesulfonamide;
4-[6-(5-methylpyridin-2-yl)spiro[2.4]hept-5-en-5-yl]benzenesulfonamide;
4-[6-(5-methoxypyridin-2-yl)spiro[2.4]hept-5-en-5yl]benzenesulfonamide;
4-[6-(5-methylthiopyridin-2-yl)spiro[2.4]hept-5-en-5-yl]benzenesulfonamide;
4-[6-(5-cyanopyridin-2-yl)spiro[2.4]hept-5-en-5-yl]benzenesulfonamide;
4-[6-(5-trifluoromethylpyridin-2-yl)spiro[2.4]hept-5-en-5-yl]benzenesulfonamide;
2-[7-[4-(methylsulfonyl)phenyl]spiro[3.4]oct-6-en-6-yl]pyridine;
5-fluoro-2-[7-[4-(methylsulfonyl)phenyl]spiro[3.4]oct-6-en-6-yl]pyridine;
5-chloro-2-[7-[4-(methylsulfonyl)phenyl]spiro[3.4]oct-6-en-6-yl]pyridine;
5-methyl-2-[7-[4-(methylsulfonyl)phenyl]spiro[3.4]oct-6-en-6-yl]pyridine;
5-methoxy-2-[7-[4-(methylsulfonyl)phenyl]spiro[3.4]oct -6-en-6-yl]pyridine;
5-methylthio-2-[7-[4-(methylsulfonyl)phenyl]spiro[3.-4]oct-6-en-6-yl]pyridine;
5-cyano-2-[7-[4-(methylsulfonyl)phenyl]spiro[3.4]oct-6-en-6-yl]pyridine;
5-trifluoromethyl-2-[7-[4-(methylsulfonyl)phenyl]-spiro[3.4]oct -6-en-6-yl]pyridine;
4-[7-(pyridin-2-yl)spiro[3.4]oct-6-en-6-yl]benzenesulfonamide;

4-[7-(5-fluoropyridin-2-yl)spiro[3.4]oct-6-en-6-yl]benzenesulfonamide;

4-[7-(5-chloropyridin-2-yl)spiro[3.4]oct-6-en-6-yl]benzenesulfonamide;

4-[7-(5-methylpyridin-2-yl)spiro[3.4]oct-6-en-6-yl]benzenesulfonamide;

4-[7-(5-methoxypyridin-2-yl)spiro[3.4]oct-6-en-6-yl]benzenesulfonamide;

4-[7-(5-methylthiopyridin-2-yl)spiro[3.4]oct-6-en-6yl]benzenesulfonamide;

4-[7-(5-cyanopyridin-2-yl)spiro[3.4]oct-6-en-6-yl]benzenesulfonamide;

4-[7-(5-trifluoromethylpyridin-2-yl)spiro[3.4]oct-6-en-6-yl]benzenesulfonamide;

2-[3-[4-(methylsulfonyl)phenyl]spiro[4.4]non-2-en-2yl]pyridine;

5-fluoro-2-[3-[4-(methylsulfonyl)phenyl]spiro[4.4]non-2-en-2-yl]pyridine;

5-chloro-2-[3-[4-(methylsulfonyl)phenyl]spiro[4.4]non-2-en-2-yl]pyridine;

5-methyl-2-[3-[4-(methylsulfonyl)phenyl]spiro[4.4]non-2-en-2-yl]pyridine;

5-methoxy -2-[3-[4-(methylsulfonyl)phenyl]spiro[4.4]non -2-en-2-yl]pyridine;

5-methylthio-2-[3-[4-(methylsulfonyl)phenyl]spiro[4.4]-non-2-en-2-yl]pyridine; 5-cyano-2-[3-[4-(methylsulfonyl)phenyl]spiro[4.4]non-2-en-2-yl]pyridine;

5-trifluoromethyl-2-[3-[4-(methylsulfonyl)phenyl]-spiro[4.4]non-2-en-2-yl]pyridine;

4-[3-(pyridin-2-yl)spiro[4.4]non-2-en-2-yl]benzenesulfonamide;

4-[3-(5-fluoropyridin-2-yl)spiro[4.4]non-2-en-2-yl]benzenesulfonamide;

4-[3-(5-chloropyridin-2-yl)spiro[4.4]non-2-en-2-yl]benzenesulfonamide;

4-[3-(5-methylpyridin-2-yl)spiro[4.4]non-2-en-2-yl]benzenesulfonamide;

4-[3-(5-methoxypyridin-2-yl)spiro[4.4]non-2-en-2-yl]benzenesulfonamide;

4-[3-(5-methylthiopyridin-2-yl)spiro[4.4]non-2-en-2yl]benzenesulfonamide;

4-[3-(5-cyanopyridin-2-yl)spiro[4.4]non-2-en-2-yl]benzenesulfonamide;

4-[3-(5-trifluoromethylpyridin-2-yl)spiro[4.4]non-2-en-2-yl]benzenesulfonamide; -

2(6-phenylspiro[2.4]hept-5-en-5-yl)-5-(methylsulfonyl)-pyridine;

2-[6-(4-fluorophenyl)spiro[2.4]hept-5-en-5-yl]-5-(methylsulfonyl)pyridine;

2-[6-(4-chlorophenyl)spiro[2.4]hept-5-en-5-yl]-5-(methylsulfonyl)pyridine;

2-[6-(4-methylphenyl)spiro[2.4]hept-5-en-5-yl]-5-(methylsulfonyl)pyridine;

2-[6-(4-methoxyphenyl)spiro[2.4]hept-5-en-5-yl]-5-(methylsulfonyl)pyridine;

2-[6-(4-methylthiophenyl)spiro[2.4]hept-5-en-5-yl]-5-(methylsulfonyl)pyridine;

2-[6-(4-cyanophenyl)spiro[2.4]hept-5-en-5-yl]-5-(methylsulfonyl)pyridine;

2-[6-(4-trifluoromethylphenyl)spiro[2.4]hept-5-en-5yl]-5-(methylsulfonyl)pyridine;

2-(6-phenylspiro[2.4]hept-5-en-5-yl]-5-pyridinesulfonamide;

2-[6-(4-fluorophenyl)spiro[2.4]hept-5-en-5-yl]-5pyridinesulfonamide;

2-[6-(4-chlorophenyl)spiro[2.4]hept-5-en-5-yl]-5pyridinesulfonamide;

2-[6-(4-methylphenyl)spiro[2.4]hept-5-en-5-yl]-5pyridinesulfonamide;

2-[6-(4-methoxyphenyl)spiro[2.4]hept-5-en-5-yl]-5pyridinesulfonamide;

2-[6-(4-methylthiophenyl)spiro[2.4]hept-5-en-5-yl]-5-pyridinesulfonamide;

2-[6-(4-cyanophenyl)spiro[2.4]hept-5-en-5-yl]-5pyridinesulfonamide;

2-[6-(4-trifluoromethylphenyl)spiro[2.4]hept-5-en-5yl]-5-pyridinesulfonamide;

2-(7-phenylspiro[3.4]oct-6-en-6-yl)-5-(methylsulfonyl)-pyridine;

2-[7-(4-fluorophenyl)spiro[3.4]oct-6-en-6-yl]-5-(methylsulfonyl)pyridine;

2-[7-(4-chlorophenyl)spiro[3.4]oct-6-en-6-yl]-5-(methylsulfonyl)pyridine;

2-[7-(4-methylphenyl)spiro[3.4]oct-6-en-6-yl]-5-(methylsulfonyl)pyridine;

2-[7-(4-methoxyphenyl)spiro[3.4]oct-6-en-6-yl]-5-(methylsulfonyl)pyridine;

2-[7-(4-methylthiophenyl)spiro[3.4]oct -6-en-6-yl]-5-(methylsulfonyl)pyridine;

2-[7-(4-cyanophenyl)spiro[3.4]oct-6-en-6-yl]-5-(methylsulfonyl)pyridine;

2-[7-(4-trifluoromethylphenyl)spiro[3.4]oct-6-en-6-yl]-5-(methylsulfonyl)pyridine;

2-(7-phenylspiro[3.4]oct-6-en-6-yl)-5pyridinesulfonamide;

2-[7-(4-fluorophenyl)spiro[3.4]oct-6-en-6-yl]-5pyridinesulfonamide;

2-[7-(4-chlorophenyl)spiro[3.4]oct-6-en-6-yl]-5pyridinesulfonamide;

2-[7-(4-methylphenyl)spiro[3.4]oct-6-en-6-yl]-5pyridinesulfonamide;

2-[7-(4-methoxyphenyl)spiro[3.4]oct-6-en-6-yl]-5pyridinesulfonamide;

2-[7-(4-methylthiophenyl)spiro[3.4]oct-6-en-6-yl]-5pyridinesulfonamide;

2-[7-(4-cyanophenyl)spiro[3.4]oct-6-en-6-yl]-5pyridinesulfonamide;

2-[7-(4-trifluoromethylphenyl)spiro[3.4]oct-6-en-6yl]-5-pyridinesulfonamide;

2-(3-phenylspiro[4.4]non-2-en-2-yl)-5-(methylsulfonyl)-pyridine;

2-[3-(4-fluorophenyl)spiro[4.4]non-2-en-2-yl]-5-(methylsulfonyl)pyridine;

2-[3-(4-chlorophenyl)spiro[4.4]non-2-en-2-yl]-5-(methylsulfonyl)pyridine;

2-[3-(4-methylphenyl)spiro[4.4]non-2-en-2-yl]-5-(methylsulfonyl)pyridine;

2-[3-(4-methoxyphenyl)spiro[4.4]non-2-en-2-yl]-5-(methylsulfonyl)pyridine;

2-[3-4-methylthiophenyl)spiro[4.4]non-2-en-2-yl]-5-(methylsulfonyl)pyridine;

2-[3-4-cyanophenyl)spiro[4.4]non-2-en-2-yl]-5-(methylsulfonyl)pyridine;

2-[3-(4-trifluoromethylphenyl)spiro[4.4]non-2-en-2yl]-5-(methylsulfonyl)pyridine;

2-(3-phenylspiro[4.4]non-2-en-2-yl)-5pyridinesulfonamide;

2-[3-(4-fluorophenyl)spiro[4.4]non-2-en-2-yl]-5pyridinesulfonamide;

2-[3-(4-chlorophenyl)spiro[4.4]non-2-en-2-yl]-5pyridinesulfonamide;

2-[3-(4-methylphenyl)spiro[4.4]non-2-en-2-yl]-5pyridinesulfonamide;

2-[3-(4-methoxyphenyl)spiro[4.4]non-2-en-2-yl]-5pyridinesulfonamide;

2-[3-(4-cyanophenyl)spiro[4.4]non-2-en-2-yl]-5-pyridinesulfonamide; and
2-[3-(4-trifluoromethylphenyl)spiro[4.4]non-2-en-2-yl]-5-pyridinesulfonamide.

Within Formula I there is a fourth subclass of compounds of high interest represented by Formula V:

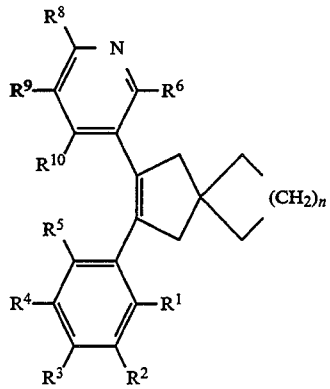

wherein n is a number selected from 0, 1, 2 and 3; and wherein each of $R^1$ through $R^6$ and $R^8$ through $R^{10}$ is independently selected from hydrido, halo, alkyl, alkoxy, alkylthio, cyano, haloalkyl, hydroxyalkyl, alkoxyalkyl, hydroxyl, mercapto, alkylsulfonyl and sulfamyl; or a pharmaceutically-acceptable salt thereof.

A preferred class of compounds consists of those compounds of Formula V wherein n is a number selected from 0, 1 and 2; wherein each of $R^1$, $R^2$, $R^4$, $R^5$, $R^6$, $R^9$ and $R^{10}$ is independently selected from hydrido, halo, lower alkyl, lower alkoxy, lower alkylthio, cyano, lower haloalkyl, lower hydroxyalkyl, lower alkoxyalkyl, hydroxyl and mercapto; and wherein $R^3$ is selected from lower alkylsulfonyl and sulfamyl and $R^8$ is selected from hydrido, halo, lower alkyl, lower alkoxy, lower alkylthio, cyano and lower haloalkyl; or wherein further, $R^3$ is selected from hydrido, halo, lower alkyl, lower alkoxy, lower alkylthio, cyano and lower haloalkyl and $R^8$ is selected from lower alkylsulfonyl and sulfamyl; or a pharmaceutically-acceptable salt thereof.

A class of compounds of particular interest consists of those compounds of Formula V wherein each of $R^1$, $R^2$, $R^4$, $R^5$, $R^6$, $R^9$ and $R^{10}$ is hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl and $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; or wherein further, $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl, and $R^8$ is methylsulfonyl or sulfamyl; or a pharmaceutically-acceptable salt thereof.

A family of specific compounds of particular interest within Formula V consists of compounds and pharmaceutically-acceptable salts thereof as follows:

5-[6-[4-(methylsulfonyl)phenyl]spiro[2.4]hept-5-en-5-yl]pyridine;
2-fluoro-5-[6-[4-(methylsulfonyl)phenyl]spiro[2.4]hept-5-en -5-yl]pyridine;
2-chloro-5-[6-[4-(methylsulfonyl)phenyl]spiro[2.4]hept-5-en-5-yl]pyridine;
2-methyl-5-[6-[4-(methylsulfonyl)phenyl]spiro[2.4]hept-5-en -5-yl]pyridine;
2-methoxy-5-[6-[4-(methylsulfonyl)phenyl]spiro[2.4]hept-5-en-5-yl]pyridine;
2-methylthio-5-[6-[4-(methylsulfonyl)phenyl]spiro[2.4]hept-5-en-5-yl]pyridine;
2-cyano-5-[6-[4-(methylsulfonyl)phenyl]spiro[2.4]hept-5-en -5-yl]pyridine;
2-trifluoromethyl-5-[6-[4-(methylsulfonyl)phenyl]-spiro[2.4]hept-5-en-5-yl]pyridine;
4-[6-(pyridin-5-yl)spiro[2.4]hept-5-en-5-yl]benzenesulfonamide;
4-[6-(2-fluoropyridin-5-yl)spiro[2.4]hept-5-en-5-yl]benzenesulfonamide;
4-[6-(2-chloropyridin-5-yl)spiro[2.4]hept-5-en-5-yl]benzenesulfonamide;
4-[6-(2-methylpyridin-5-yl)spiro[2.4]hept-5-en-5-yl]benzenesulfonamide;
4-[6-(2-methoxypyridin-5-yl)spiro[2.4]hept-5-en-5yl]benzenesulfonamide;
4-[6-(2-methylthiopyridin-5-yl)spiro[2.4]hept-5-en-5-yl]benzenesulfonamide;
4-[6-(2-cyanopyridin-5-yl)spiro[2.4]hept-5-en-5-yl]benzenesulfonamide;
4-[6-(2-trifluoromethylpyridin-5-yl)spiro[2.4]hept-5-en-5-yl]benzenesulfonamide;
5-[7-[4-(methylsulfonyl)phenyl]spiro[3.4]oct-6-en-6yl]-pyridine;
2-fluoro-5-[7-[4-(methylsulfonyl)phenyl]spiro[3.4]oct-6-en-6-yl]pyridine;
2-chloro-5-[7-[4-(methylsulfonyl)phenyl]spiro[3.4]oct -6-en-6-yl]pyridine;
2-methyl-5-[7-[4-(methylsulfonyl)phenyl]spiro[3.4]oct-6-en-6-yl]pyridine;
2-methoxy-5-[7-[4-(methylsulfonyl)phenyl]spiro[3.-4]oct-6-en-6-yl]pyridine;
2-methylthio-5-[7-[4-(methylsulfonyl)phenyl]spiro[3.-4]oct-6-en-6-yl]pyridine;
2-cyano-5-[7-[4-(methylsulfonyl)phenyl]spiro[3.4]oct -6-en-6-yl]pyridine;
2-trifluoromethyl-5-[7-[4-(methylsulfonyl)phenyl]-spiro[3.4]oct-6-en-6-yl]pyridine;
4-[7-(pyridin-5-yl)spiro[3.4]oct-6-en-6-yl]benzenesulfonamide;
4-[7-(2-fluoropyridin-5-yl)spiro[3.4]oct-6-en-6-yl]benzenesulfonamide;
4-[7-(2-chloropyridin-5-yl)spiro[3.4]oct-6-en-6-yl]benzenesulfonamide;
4-[7-(2-methylpyridin-5-yl)spiro[3.4]oct-6-en-6-yl]benzenesulfonamide;
4-[7-(2-methoxypyridin-5-yl)spiro[3.4]oct-6-en-6-yl]benzenesulfonamide;

4-[7-(2-methylthiopyridin-5-yl)spiro[3.4]oct-6-en-6yl]benzenesulfonamide;

4-[7-(2-cyanopyridin-5-yl)spiro[3.4]oct-6-en-6-yl]benzenesulfonamide;

4-[7-(2-trifluoromethylpyridin-5-yl)spiro[3.4]oct-6-en-6-yl]benzenesulfonamide;

5-[3-[4-(methylsulfonyl)phenyl]spiro[4.4]non-2-en-2yl]pyridine;

2-fluoro-5-[3-[4-(methylsulfonyl)phenyl]spiro4.4]non-2-en-2-yl]pyridine;

2-chloro-5-[3-[4-(methylsulfonyl)phenyl]spiro 4.4]non-2-en-2-yl]pyridine;

2-methyl-5-[3-[4-(methylsulfonyl)phenyl]spiro[4.4]non-2-en-2-yl]pyridine;

2-methoxy-5-[3-[4-(methylsulfonyl)phenyl]spiro[4.4]non-2-en-2-yl]pyridine;

2-methylthio-5-[3-[4-(methylsulfonyl)phenyl]spiro[4.4]non-2-en-2-yl]pyridine;

2-trifluoromethyl-5-[3-[4-(methylsulfonyl)phenyl]spiro[4.4]non-2-en-2-yl]pyridine;

4-[3-(pyridin-5-yl)spiro[4.4]non-2-en-2-yl]benzenesulfonamide;

4-[3-(2-fluoropyridin-5-yl)spiro[4.4]non-2-en-2-yl]benzenesulfonamide;

4-[3-(2-chloropyridin-5-yl)spiro[4.4]non-2-en-2-yl]benzenesulfonamide;

4-[3-(2-methylpyridin-5-yl)spiro[4.4]non-2-en-2-yl]benzenesulfonamide;

4-[3-(2-methoxypyridin-5-yl)spiro[4.4]non-2-en-2-yl]benzenesulfonamide;

4-[3-(2-methylthiopyridin-5-yl)spiro[4.4]non-2-en-2yl]benzenesulfonamide;

4-[3-(2-cyanopyridin-5-yl)spiro[4.4]non-2-en-2-yl]benzenesulfonamide;

4-[3-(2-trifluoromethylpyridin-5-yl)spiro[4.4]non-2-en-2-yl]benzenesulfonamide;

5-(6-phenylspiro[2.4]hept-5-en-5-yl)-2-(methylsulfonyl)pyridine;

5-[6-(4-fluorophenyl spiro[2.4]hept-5-en-5-yl]-2-(methylsulfonyl)pyridine;

5-[6-(4-chlorophenyl spiro[2.4]hept-5-en-5-yl]-2-(methylsulfonyl)pyridine;

5-[6-(4-methylphenyl spiro[2.4]hept-5-en-5-yl]-2-(methylsulfonyl)pyridine;

5-[6-(4-methoxyphenyl)spiro[2.4]hept-5-en-5-yl]-2-(methylsulfonyl)pyridine;

5-[6-(4-methylthiophenyl)spiro[2.4]hept-5-en-5-yl]-2-(methylsulfonyl)pyridine;

5-[6-(4-cyanophenyl)spiro[2.4]hept-5-en-5-yl]-2-(methylsulfonyl)pyridine;

5-[6-(4-trifluoromethylphenyl)spiro[2.4]hept-5-en-5-yl]-2-(methylsulfonyl)pyridine;

5-(6-phenylspiro[2.4]hept-5-en-5-yl)-2-pyridinesulfonamide;

5-[6-(4-fluorophenyl)spiro[2.4]hept-5-en-5-yl]-2-pyridinesulfonamide;

5-[6-(4-chlorophenyl)spiro[2.4]hept-5-en-5-yl]-2-pyridinesulfonamide;

5-[6-(4-methylphenyl)spiro[2.4]hept-5-en-5-yl]-2-pyridinesulfonamide;

5-[6-(4-methoxyphenyl)spiro[2.4]hept-5-en-5-yl]-2-pyridinesulfonamide;

5-[6-(4-methylthiophenyl)spiro[2.4]hept-5-en-5-yl]-2-pyridinesulfonamide;

5-[6-(4-cyanophenyl)spiro[2.4]hept-5-en-5-yl]-2-pyridinesulfonamide;

5-[6-(4-trifluoromethylphenyl)spiro[2.4]hept-5-en-5-yl]-2-pyridinesulfonamide;

5-(7-phenylspiro[3.4]oct-6-en-6-yl)-2-(methylsulfonyl)pyridine;

5-[7-(4-fluorophenyl)spiro[3.4]oct-6-en-6-yl]-2-(methylsulfonyl)pyridine;

5-[7-(4-chlorophenyl)spiro[3.4]oct-6-en-6-yl]-2-(methylsulfonyl)pyridine;

5-[7-(4-methylphenyl)spiro[3.4]oct-6-en-6-yl]-2-(methylsulfonyl)pyridine;

5-[7-(4-methoxyphenyl)spiro[3.4]oct-6-en-6-yl]-2-(methylsulfonyl)pyridine;

5-[7-(4-methylthiophenyl)spiro[3.4]oct-6-en-6-yl]-2-(methylsulfonyl)pyridine;

5-[7-(4-cyanophenyl)spiro[3.4]oct-6-en-6-yl]-2-(methylsulfonyl)pyridine;

5-[7-(4-trifluoromethylphenyl)spiro[3.4]oct-6-en-6yl]-2-(methylsulfonyl)pyridine;

5-(7-phenylspiro[3.4]oct-6-en-6-yl)-2-pyridinesulfonamide;

5-[7-(4-fluorophenyl)spiro[3.4]oct-6-en-6-yl]-2-pyridinesulfonamide;

5-[7-(4-chlorophenyl)spiro[3.4]oct-6-en-6-yl]-2-pyridinesulfonamide;

5-[7-(4-methylphenyl)spiro[3.4]oct-6-en-6-yl]-2-pyridinesulfonamide;

5-[7-(4-methoxyphenyl)spiro[3.4]oct-6-en-6-yl]-2-pyridinesulfonamide;

5-[7-(4-cyanophenyl)spiro[3.4]oct-6-en-6-yl]-2-pyridinesulfonamide;

5-[7-(4-trifluoromethylphenyl)spiro[3.4]oct-6-en-6-yl]-2-pyridinesulfonamide;

5-(3-phenylspiro[4.4]non-2-en-2-yl)-2-(methylsulfonyl)pyridine;

5-[3-(4-fluorophenyl)spiro[4.4]non-2-en-2-yl]-2-(methylsulfonyl)pyridine;

5-[3-(4-chlorophenyl)spiro[4.4]non-2-en-2-yl]-2-(methylsulfonyl)pyridine;

5-[3-(4-methylphenyl)spiro[4.4]non-2-en-2-yl]-2-(methylsulfonyl)pyridine;

5-[3-(4-methoxyphenyl)spiro[4.4]non-2-en-2-yl]-2-(methylsulfonyl)pyridine;

5-[3-(4-methylthiophenyl)spiro[4.4]non-2-en-2-yl]-2-(methylsulfonyl)pyridine;

5-[3-(4-cyanophenyl)spiro[4.4]non-2-en-2-yl]-2-(methylsulfonyl)pyridine;

5-[3-(4-trifluoromethylphenyl)spiro[4.4]non-2-en-2-yl]-2-(methylsulfonyl)pyridine;

5-(3-phenylspiro[4.4]non-2-en-2-yl)-2-pyridinesulfonamide;

5-[3-(4-fluorophenyl)spiro[4.4]non-2-en-2-yl]-2pyridinesulfonamide;

5-[3-(4-chlorophenyl)spiro[4.4]non-2-en-2-yl]-2pyridinesulfonamide;

5-[3-(4-methylphenyl)spiro[4.4]non-2-en-2-yl]-2pyridinesulfonamide;

5-[3-(4-methoxyphenyl)spiro[4.4]non-2-en-2-yl]-2pyridinesulfonamide;

5-[3-(4-methylthiophenyl)spiro[4.4]non-2-en-2-yl]-2pyridinesulfonamide;

5-[3-(4-cyanophenyl)spiro[4.4]non-2-en-2-yl]-2pyridinesulfonamide; and

5-[3-(4-trifluoromethylphenyl)spiro[4.4]non-2-en-2-yl]-2-pyridinesulfonamide.

Within Formula I there is a fifth subclass of compounds of high interest represented by Formula VI:

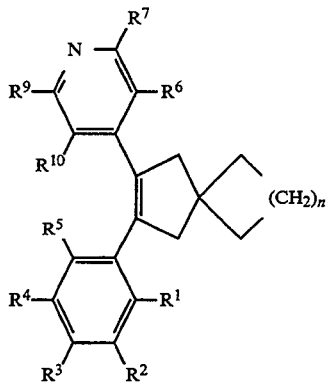

VI wherein n is a number selected from 0, 1, 2 and 3; and wherein each of $R^1$ through $R^7$, $R^9$ and $R^{10}$ is independently selected from hydrido, halo, alkyl, alkoxy, alkylthio, cyano, haloalkyl, hydroxyalkyl, alkoxyalkyl, hydroxyl, mercapto, alkylsulfonyl and sulfamyl; or a pharmaceutically-acceptable salt thereof.

A preferred class of compounds consists of those compounds of Formula VI wherein n is a number selected from 0, 1 and 2; wherein each of $R^1$, $R^2$, $R^4$ through $R^7$, $R^9$ and $R^{10}$ is independently selected from hydrido, halo, lower alkyl, lower alkylthio, cyano, hydroxyl, mercapto, lower haloalkyl, lower alkoxy, lower hydroxyalkyl and lower alkoxyalkyl; and wherein $R^3$ is selected from lower alkylsulfonyl and sulfamyl; or a pharmaceutically-acceptable salt thereof.

A class of compounds of particular interest consists of those compounds of Formula VI wherein each of $R^1$, $R^2$, $R^4$ through $R^7$, $R^9$ and $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl; or a pharmaceutically-acceptable salt thereof.

A family of specific compounds of particular interest within Formula VI consists of compounds and pharmaceutically-acceptable salts thereof as follows:

4-[6-[4-(methylsulfonyl)phenyl]spiro[2.4]hept-5-en-5-yl]pyridine;
4-[6-(4-pyridinyl)spiro[2.4]hept-5-en-5-yl]benzenesulfonamide;
4-[7-[4-(methylsulfonyl)phenyl]spiro[3.4]oct-6-en-6-yl]pyridine;
4-[7-(4-pyridinyl)spiro[3.4]oct-6-en-6-yl]benzenesulfonamide;
4-[3-[4-(methylsulfonyl)phenyl]spiro[4.4]non-2-en-2-yl]pyridine; and
4-[3-(4-pyridinyl)spiro[4.4]non-2-en-2-yl]benzenesulfonamide.

Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about ten carbon atoms attached to a divalent sulfur atom, such as a methythio radical, ($CH_3$—S—). The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl" or "sulfonamidyl" denotes a sulfonyl radical substituted with an amine radical, forming a sulfonamide (—$SO_2NH_2$).

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–XIX, wherein the $R^1$–$R^{10}$ substituents are as defined for Formula I, above, except where further noted.

Scheme I

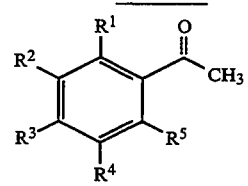

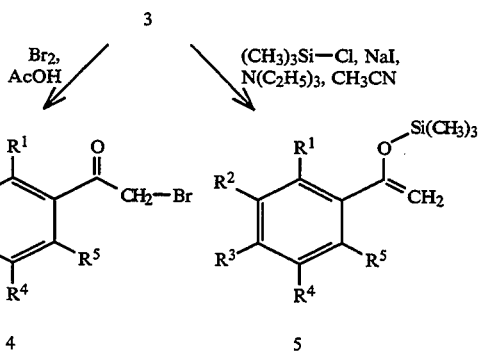

Synthetic Scheme I shows the three step procedures used to prepare the bromoacetophenones 4 and the phenyl silyl enol ethers 5 from commercially available benzoic acids 1. In step one, a THF solution at 0° C. of the benzoic acids 1 and two equivalents of triethylamine are sequentially treated with isobutyl chloroformate and N-hydroxymethyl-N-methylamine hydrochloride to give the Weinreb amides 2 [see: S. Natim and S. M. Weinreb, Tetrahedron Lett., 21, 3815(1981)]. In step two, the amides 2 are reacted with methylmagnesium bromide to give the corresponding acetophenones 3. In step three, the acetophenones 3 are either treated with bromine in acetic acid to give the corresponding bromoacetophenones 4 or chlorotrimethylsilane in acetonitrile in the presence of triethylamine and sodium iodide to give the corresponding phenyl silyl enol ethers 5.

Scheme I

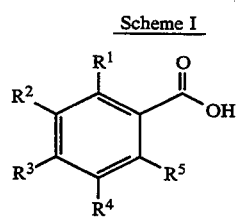

1

1. Cl—CO—OCH₂CH(CH₃)₂, THF, 0° C., N(C₂H₅)₃
2. HN(CH₃)OCH₃HCl, N(C₂H₅)₃

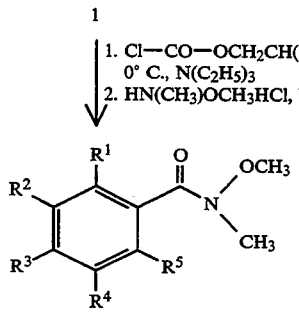

2

CH₃MgBr, THF, 0° C.

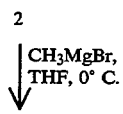

Scheme II

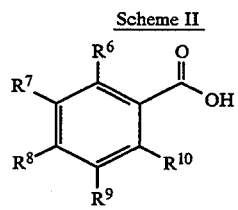

6

1. Cl—CO—OCH₂CH(CH₃)₂, THF, 0° C., N(C₂H₅)₃
2. HN(CH₃)OCH₃HCl, N(C₂H₅)₃

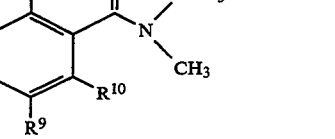

7

CH₃MgBr THF, 0° C.

-continued
Scheme II

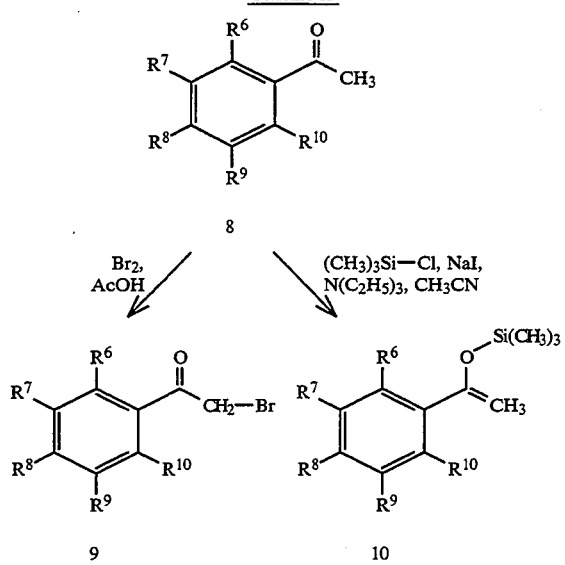

Synthetic Scheme II shows the three step procedures used to prepare the bromoacetophenones 9 and the phenyl silyl enol ethers 10 from commercially available benzoic acids 6. In step one, a THF solution at 0° C. of the benzoic acids 6 and two equivalents of triethylamine are sequentially treated with isobutyl chloroformate and N-hydroxymethyl-N-methylamine hydrochloride to give the Weinreb amides 7. In step two, the amides 7 are reacted with methylmagnesium bromide to give the corresponding acetophenones 8. In step three, the acetophenones 8 are either treated with bromine in acetic acid to give the corresponding bromoacetophenones 9 or chlorotrimethylsilane in acetonitrile in the presence of triethylamine and sodium iodide to give the corresponding phenyl silyl enol ethers 10.

-continued
Scheme III

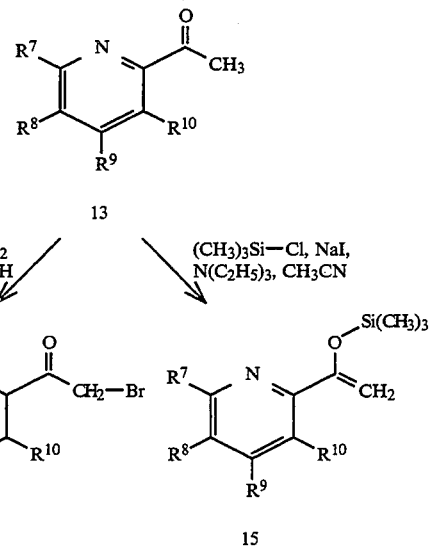

Synthetic Scheme III shows the three step procedures used to prepare the 2-(bromoacetyl)pyridines 14 and the 2-pyridinyl silyl enol ethers 15 from commercially available picolinic acids 11. In step one, a THF solution at 0° C. of the picolinic acids 11 and two equivalents of triethylamine are sequentially treated with isobutyl chloroformate and N-hydroxymethyl-N-methylamine hydrochloride to give the Weinreb amides 12. In step two, the amides 12 are reacted with methylmagnesium bromide to give the corresponding 2-acetylpyridines 13. In step three, the 2-acetylpyridines 13 are either treated with bromine in acetic acid to give the corresponding 2-(bromoacetyl)pyridines 14 or chlorotrimethylsilane in acetonitrile in the presence of triethylamine and sodium iodide to give the corresponding 2-pyridinyl silyl enol ethers 15.

Scheme III

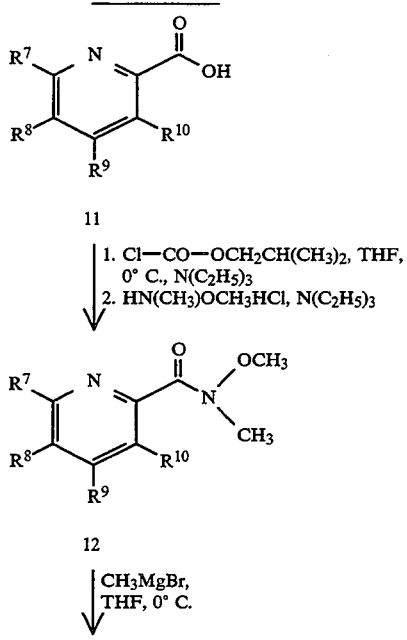

Scheme IV

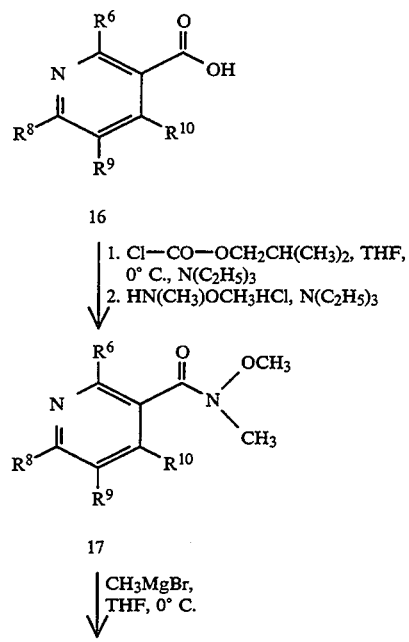

-continued
Scheme IV

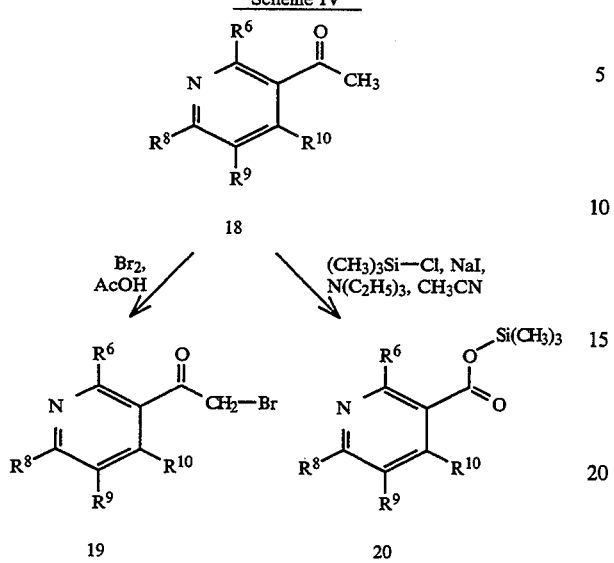

Synthetic Scheme IV shows the three step procedures used to prepare the 3-(bromoacetyl)pyridines 19 and the 3-pyridinyl silyl enol ethers 20 from commercially available nicotinic acids 16. In step one, a THF solution at 0° C. of the nicotinic acids 16 and two equivalents of triethylamine are sequentially treated with isobutyl chloroformate and N-hydroxymethyl-N-methylamine hydrochloride to give the Weinreb amides 17. In step two, the amides 17 are reacted with methylmagnesium bromide to give the corresponding 3-acetylpyridines 18. In step three, the 3-acetylpyridines 18 are either treated with bromine in acetic acid to give the corresponding 3-(bromoacetyl)pyridines 19 or chlorotrimethylsilane in acetonitrile in the presence of triethylamine and sodium iodide to give the corresponding 3-pyridinyl silyl enol ethers 20.

Scheme V

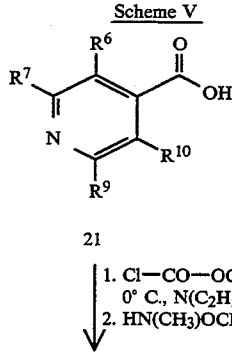

1. Cl—CO—OCH$_2$CH(CH$_3$)$_2$, THF, 0° C., N(C$_2$H$_5$)$_3$
2. HN(CH$_3$)OCH$_3$HCl, N(C$_2$H$_5$)$_3$

-continued
Scheme V

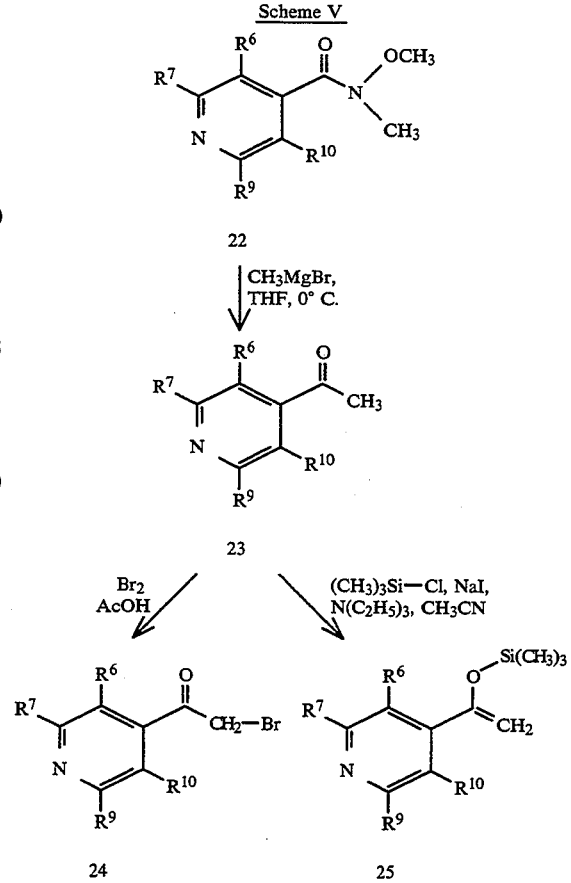

Synthetic Scheme V shows the three step procedures used to prepare the 4-(bromoacetyl)pyridines 24 and the 4-pyridinyl silyl enol ethers 25 from commercially available isonicotinic acids 21. In step one, a THF solution at 0° C. of the isonicotinic acids 21 and two equivalents of triethylamine are sequentially treated with isobutyl chloroformate and N-hydroxymethyl-N-methylamine hydrochloride to give the Weinreb amides 22. In step two, the amides 22 are reacted with methylmagnesium bromide to give the corresponding 4-acetylpyridines 23. In step three, the 4-acetylpyridines 23 are either treated with bromine in acetic acid to give the corresponding 4-(bromoacetyl)pyridines 24 or chlorotrimethylsilane in acetonitrile in the presence of triethylamine and sodium iodide to give the corresponding 4-pyridinyl silyl enol ethers 25.

Scheme VI

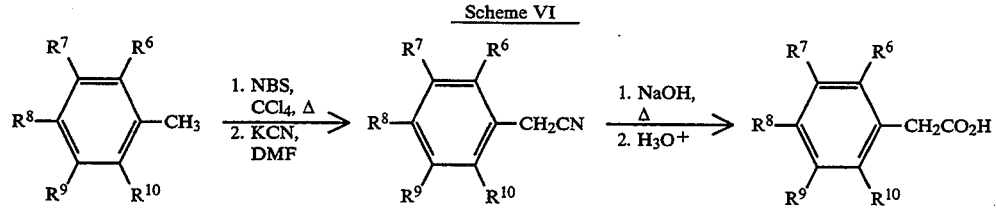

Scheme VI -continued

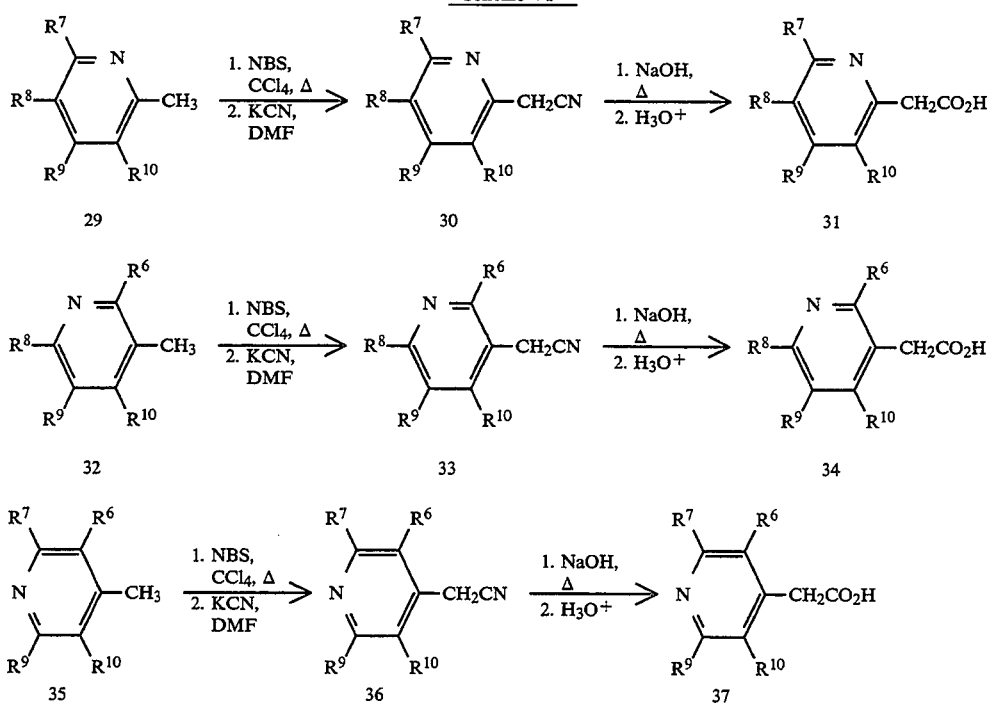

Synthetic Scheme VI shows the two step procedures which can be used to prepare the phenylacetic acids 28, 2-pyridinylacetic acids 31, 3-pyridinylacetic acids 34, and 4-pyridinylacetic acids 37 from commercially available toluenes 26, 2-picolines 29, 3-picolines 32, and 4-picolines 35, respectively. In step one, toluenes 26, 2-picolines 29, 3-picolines 32, and 4-picolines 35 are sequentially treated with N-bromosuccinimide (NBS) in carbon tetrachloride at reflux in the presence of a free radical initiater, e.g., 2,2′-azobis(2-methylpropionitrile) (AIBN), and potassium cyanide in DMF to give the corresponding phenylacetonitriles 27, 2-pyridinylacetonitriles 30, 3-pyridinylacetonitriles 33, and 4-pyridinylacetonitriles 36, respectively. In step two, phenylacetonitriles 27, 2-pyridinylacetonitriles 30, 3-pyridinylacetonitriles 33, and 4-pyridinylacetonitriles 36 are hydrolyzed with aqueous sodium hydroxide; acidification provides the phenylacetic acids 28, 2-pyridinylacetic acids 31, 3-pyridinylacetic acids 34, and 4-pyridinylacetic acids 37, respectively.

Scheme VII

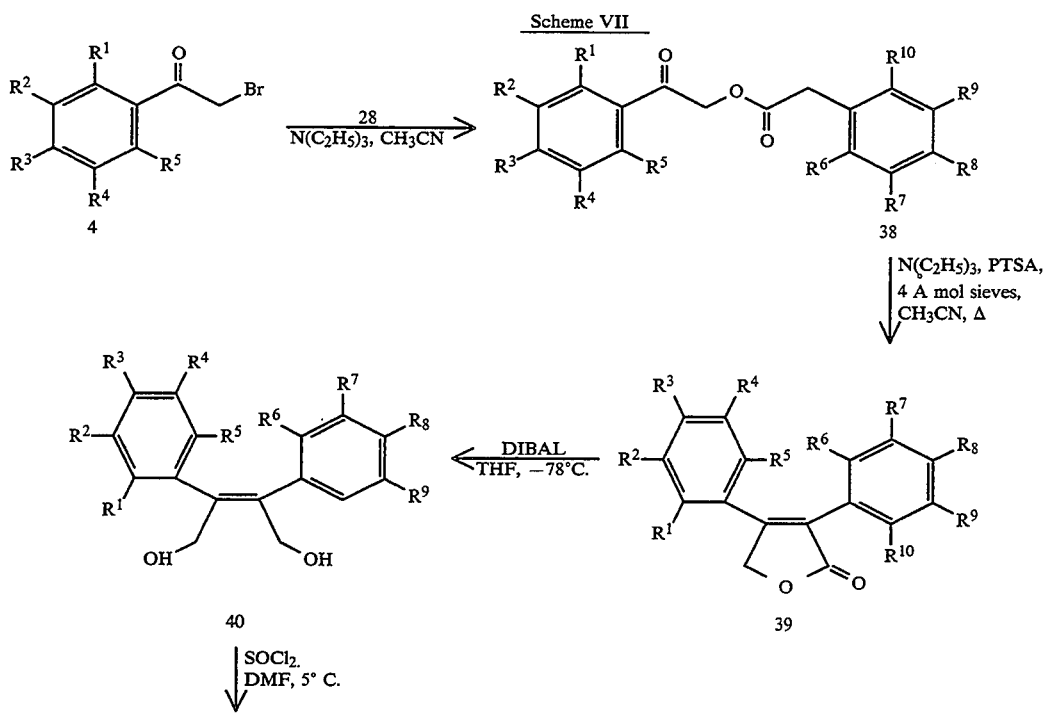

-continued
Scheme VII

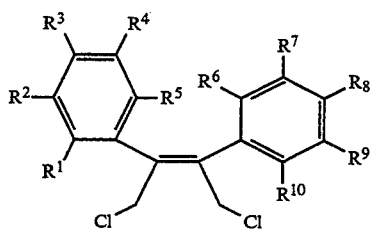

Synthetic Scheme VII shows the four step procedures used to prepare the cis-2,3-diaryl-1,4-dichloro-2-butenes 41 from the bromoacetophenones 4 (prepared in Synthetic Scheme I) and the phenylacetic acids 28 (prepared in Synthetic Scheme VI). In step one, bromoacetophenones 4 are reacted with phenylacetic acids 28 in acetonitrile in the presence of triethylamine to give the corresponding esters 38. In step two, the esters 38 are cyclized to the corresponding furanones 39 on treatment with p-toluenesulfonic acid (PTSA) and triethylamine in the presence of 4 Å molecular sieves in acetonitrile at reflux. In step three, the furanones 39 are reacted with diisobutylaluminum hydride (DIBAL) to give the corresponding cis-diols 40. In step four, the cis-diols 40 are reacted with thionyl chloride in DMF at 5° C. to give the corresponding cis-2,3-diaryl-1,4-dichloro-2-butenes

Scheme VIII

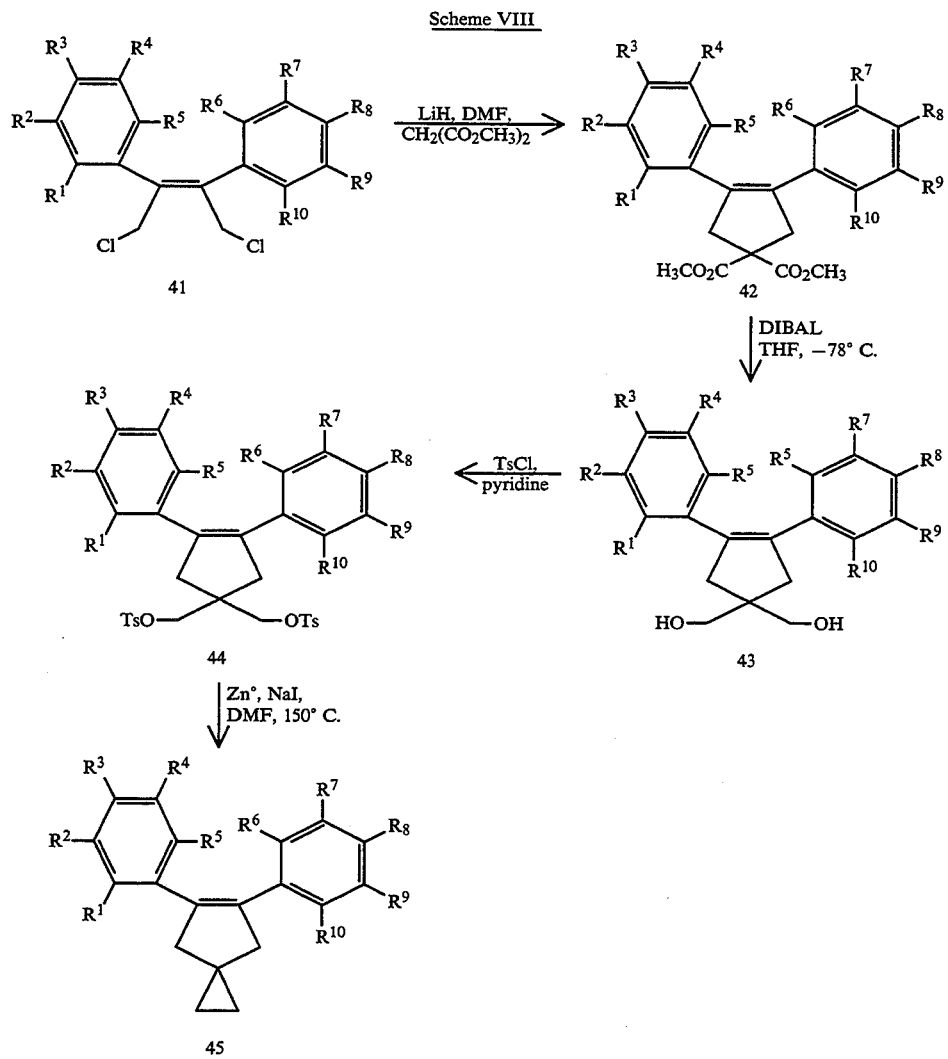

Synthetic Scheme VIII shows the four step procedure used to prepare the 5,6-diarylspiro[2.4]hept-5-enes 45 from the cis-2,3-diaryl-1,4-dichloro-2-butenes 41 (prepared in Synthetic Scheme VII). In step one, the cis-2,3-diaryl-1,4-dichloro-2-butenes 41 are reacted with dimethyl malonate in DMF in the presence of two equivalents of lithium hydride to give the corresponding 4,4-dicarbomethoxycyclopentenes 42. In step two, the 4,4-dicarbomethoxycyclopentenes 42 are reacted with DIBAL in THF to give the corresponding 4,4-di(hydroxymethyl)cyclopentenes 43. In step three, the 4,4-di(hydroxymethyl) cyclopentenes 43 are reacted with p-toluenesulfonyl chloride (TsCl) in pyridine to give the corresponding 4,4-ditosylates 44. In step four, the 4,4-ditosylates 44 are reacted with metallic zinc and sodium iodide in DMF at 150° C. to give the 5,6-diarylspiro[2.4]hept-5-ene antiinflammatory agents 45 of this invention.

(prepared in Synthetic Scheme I) and the 2-pyridinylacetic acids 31 (prepared in Synthetic Scheme VI). In step one, bromoacetophenones 4 are reacted with 2-pyridinylacetic acids 31 in acetonitrile in the presence of triethylamine to give the corresponding esters 46. In step two, the esters 46 are cyclized to the corresponding furanones 47 on treatment with p-toluenesulfonic acid (PTSA) and triethylamine in the presence of 4 Å molecular sieves in acetonitrile at reflux. In step three, the furanones 47 are reacted with diisobutylaluminumhydride (DIBAL) to give the corresponding cis-diols 48.

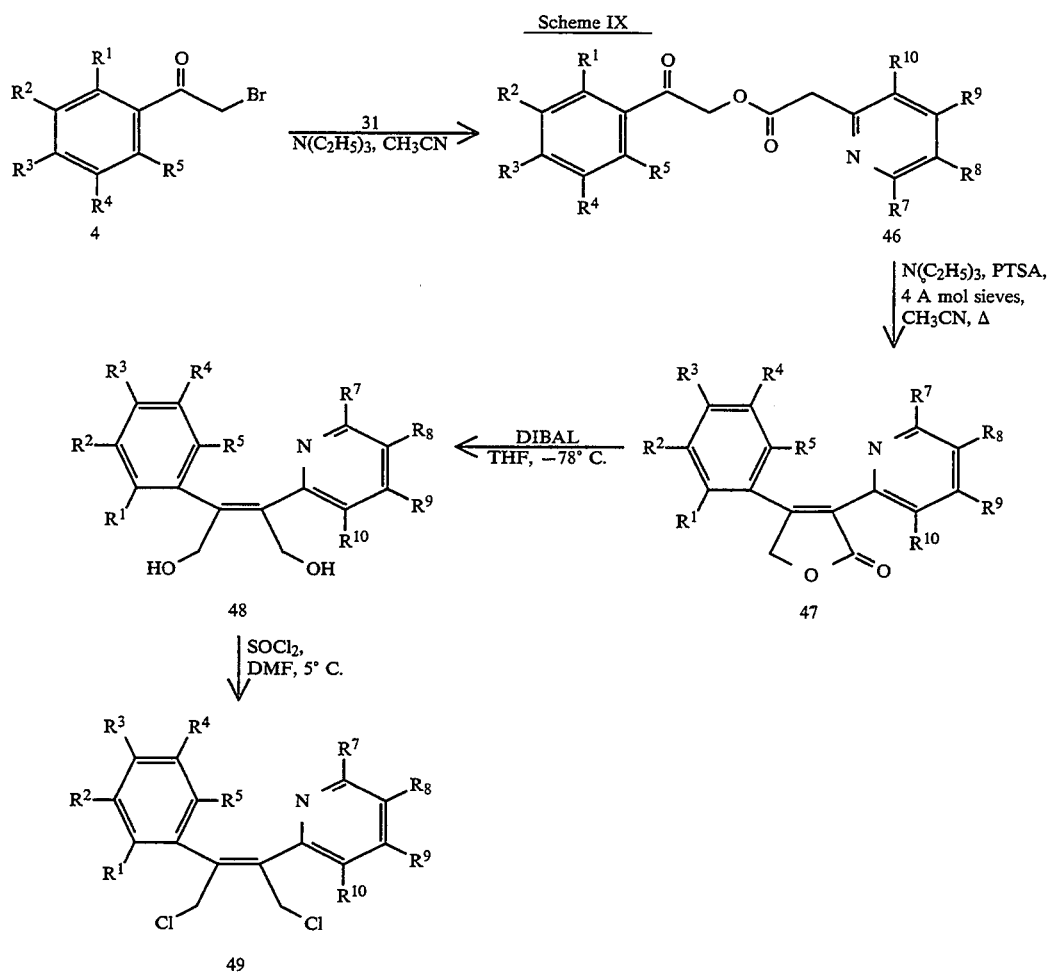

Synthetic Scheme IX shows the four step procedure used to prepare the cis-2-(2-pyridinyl)-3-aryl-1,4-dichloro-2-butenes 49 from the bromoacetophenones 4

In step four, the cis-diols 48 are reacted with thionyl chloride in DMF at 5° C. to give the corresponding cis-2-(2-pyridinyl)-3-aryl-1,4-dichloro-2-butenes 49.

Scheme X

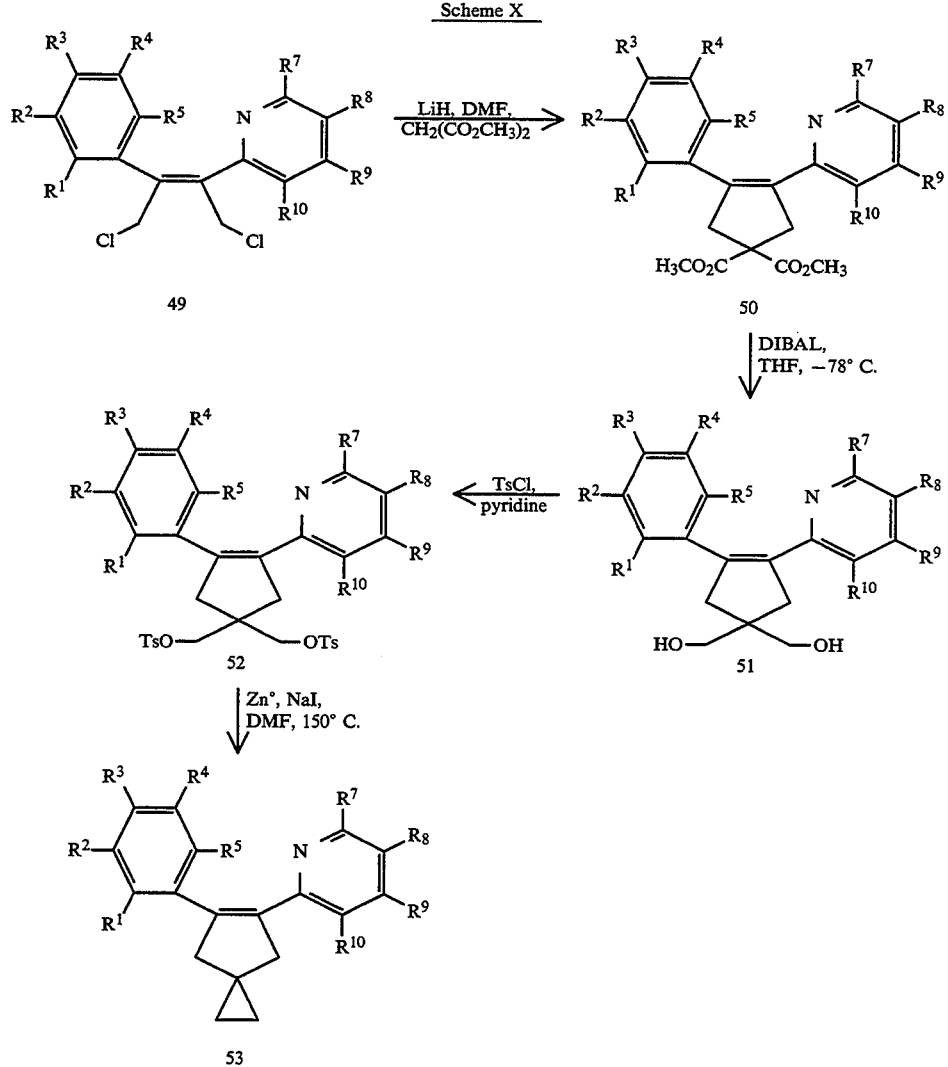

Synthetic Scheme X shows the four step procedure used to prepare the 5-(2-pyridinyl)-6-arylspiro[2.4]hept-5-enes 53 from the cis-2-(2-pyridinyl)-3-aryl-1,4-dichloro-2-butenes 49 (prepared in Synthetic Scheme IX). In step one, the cis-2-(2-pyridinyl)-3-aryl-1,4-dichloro-2-butenes 49 are reacted with dimethyl malonate in DMF in the presence of two equivalents of lithium hydride to give the corresponding 4,4-dicarbomethoxycyclopentenes 50. In step two, the 4,4-dicarbomethoxycyclopentenes 50 are reacted with DIBAL in THF to give the corresponding 4,4-di(hydroxymethyl)cyclopentenes 51. In step three, the 4,4-di(hydroxymethyl)cyclopentenes 51 are reacted with p-toluenesulfonyl chloride (TsCl) in pyridine to give the corresponding 4,4-ditosylates 52. In step four, the 4,4-ditosylates 52 are reacted with metallic zinc and sodium iodide in DMF at 150° C. to give the 5-(2-pyridinyl)-6-arylspiro[2.4]hept-5-ene antiinflammatory agents 53 of this invention.

Scheme XI

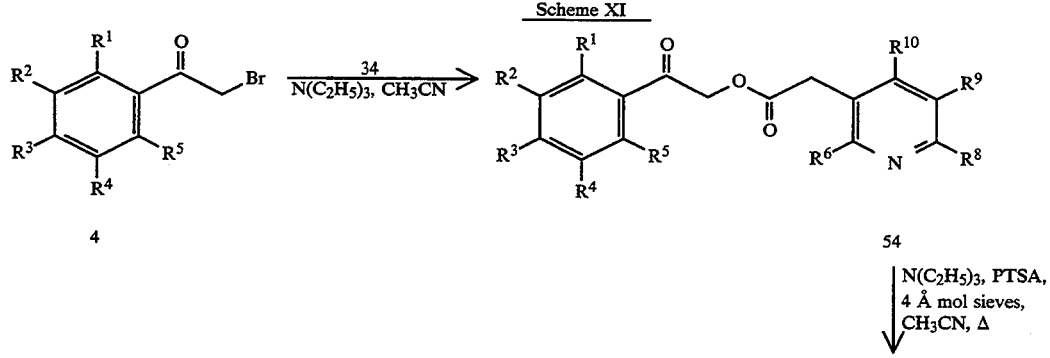

-continued
Scheme XI

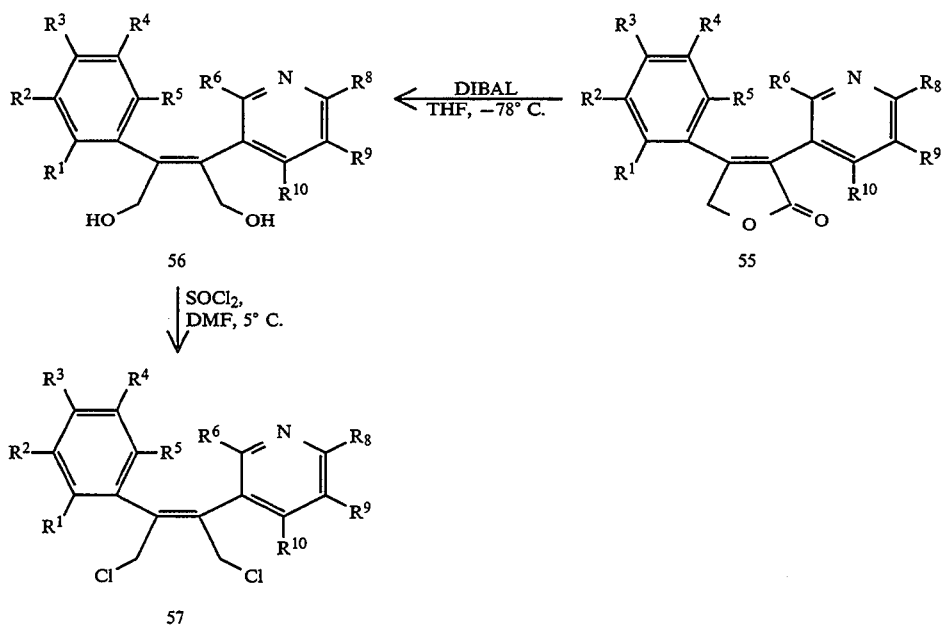

Synthetic Scheme XI shows the four step procedure used to prepare the cis-2-(3-pyridinyl)-3-aryl1,4-dichloro-2-butenes 57 from the bromoacetophenone 4 (prepared in Synthetic Scheme I) and the 3-pyridinylacetic acids 34 (prepared in Synthetic Scheme VI). In step one, bromoacetophenones 4 are reacted with 3-pyridinylacetic acids 34 in acetonitrile in the presence of triethylamine to give the corresponding esters 54. In step two, the esters 54 are cyclized to the corresponding furanones 55 on treatment with p-toluenesulfonic acid (PTSA) and triethylamine in the presence of 4 Å molecular sieves in acetonitrile at reflux. In step three, the furanones 55 are reacted with diisobutylaluminum hydride (DIBAL) to give the corresponding cis-diols 56. In step four, the cis-diols 56 are reacted with thionyl chloride in DMF at 5° C. to give the corresponding cis-2-(3-pyridinyl)-3-aryl-1,4-dichloro-2-butenes 57.

Scheme XII

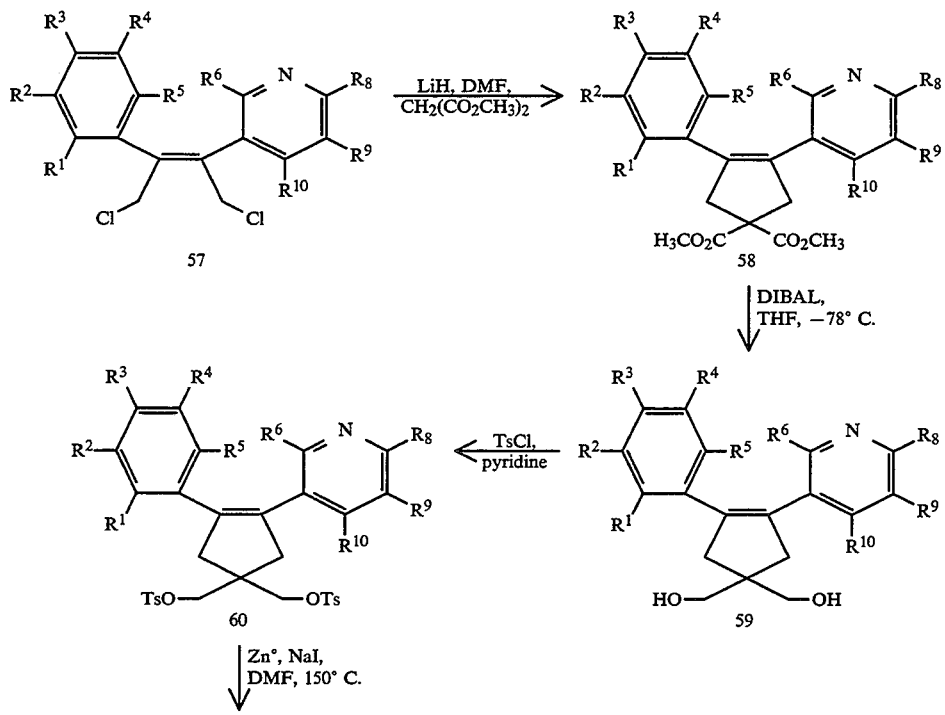

Scheme XII
-continued

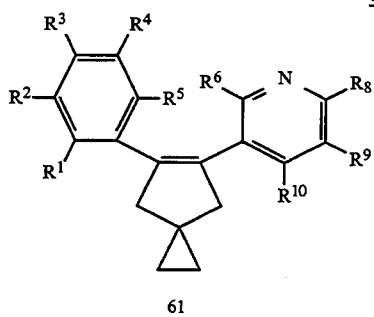

61

Synthetic Scheme XII shows the four step procedure used to prepare the 5-(3-pyridinyl)-6-arylspiro[2.4]hept-5-enes 61 from the cis-2-(3-pyridinyl)-3-aryl-1,4-dichloro-2-butenes 57 (prepared in Synthetic Scheme XI). In step one, the cis-2-(3-pyridinyl)-3-aryl-1,4-dichloro-2-butenes 57 are reacted with dimethyl malonate in DMF in the presence of two equivalents of lithium hydride to give the corresponding 4,4-dicarbomethoxycyclopentenes 58. In step two, the 4,4-dicarbomethoxycyclopentenes 58 are reacted with DIBAL in THF to give the corresponding 4,4-di(hydroxymethyl)cyclopentenes 59. In step three, the 4,4-di(hydroxymethyl)cyclopentenes 59 are reacted with p-toluenesulfonyl chloride (TsCl) in pyridine to give the corresponding 4,4-ditosylates 60. In step four, the 4,4-ditosylates 60 are reacted with metallic zinc and sodium iodide in DMF at 150° C. to give the 5-(3-pyridinyl)-6arylspiro[2.4]hept-5-ene antiinflammatory agents 61 of this invention.

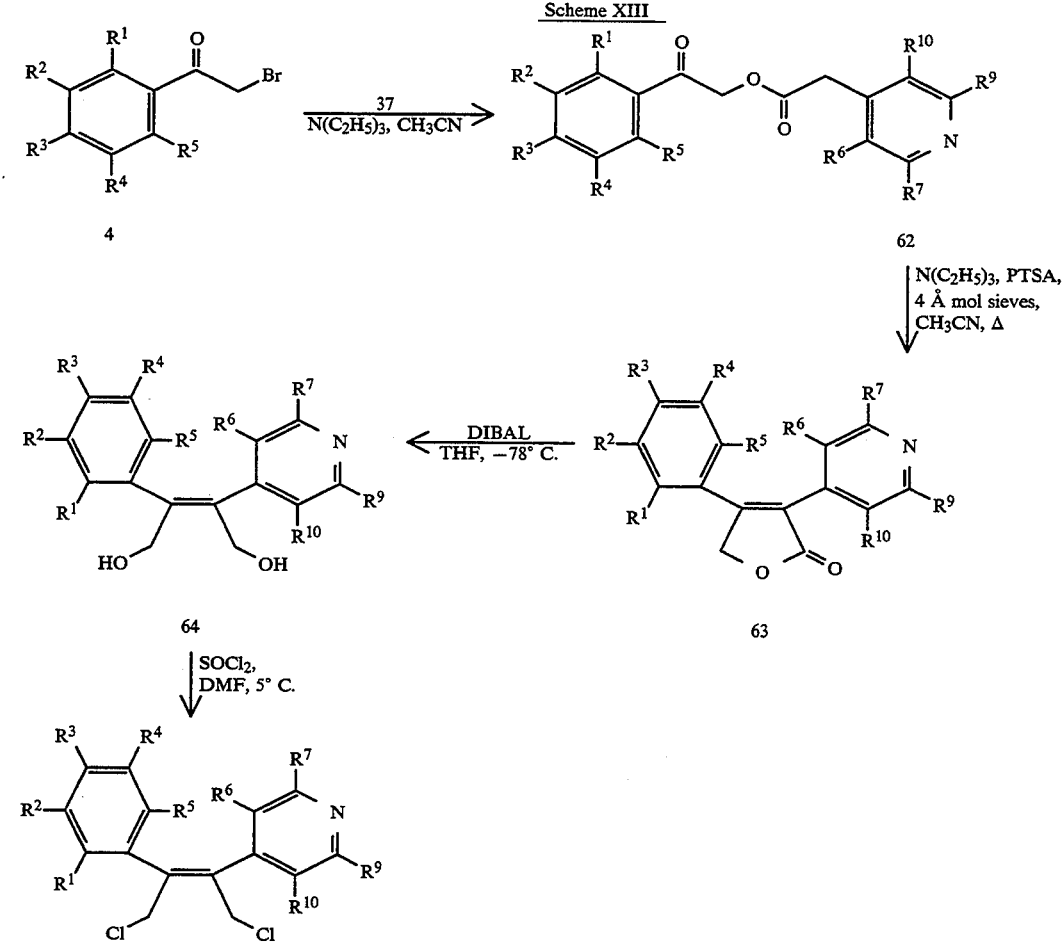

Synthetic Scheme XIII shows the four step procedure used to prepare the cis-2-(4-pyridinyl)-3-aryl-1,4-dichloro-2-butenes 65 from the bromoacetophenones 4 (prepared in Synthetic Scheme I) and the 4-pyridinylacetic acids 37 (prepared in Synthetic Scheme VI). In step one, bromoacetophenones 4 are reacted with 4-pyridinylacetic acids 37 in acetonitrile in the presence of triethylamine to give the corresponding esters 62. In step two, the esters 62are cyclized to the corresponding furanones 63 on treatment with p-toluenesulfonic acid (PTSA) and triethylamine in the presence of 4 Å molecular sieves in acetonitrile at reflux. In step three, the furanones 63 are reacted with diisobutylaluminum hydride (DIBAL) to give the corresponding cis-diols 64. In step four, the cis-diols 64 are reacted with thionyl chloride in DMF at 5° C. to give the corresponding cis-2-(4-pyridinyl)-3-aryl1,4-dichloro-2-butenes 65.

XIII). In step one, the cis-2-(4-pyridinyl)-3-aryl-1,4-dichloro-2-butenes 65 are reacted with dimethyl malonate in DMF in the presence of two equivalents of lithium hydride to give the corresponding 4,4-dicarbomethoxycyclopentenes 66. In step two, the 4,4-dicarbomethoxycyclopentenes 66 are reacted with DIBAL in THF to give the corresponding 4,4-di(hydroxymethyl)cyclopentenes 67. In step three, the 4,4-di(hydroxymethyl)cyclopentenes 67 are reacted with p-toluenesulfonyl chloride (TsCl) in pyridine to give the corresponding 4,4-ditosylates 68. In step four, the 4,4-ditosylates 68 are reacted with metallic zinc and sodium

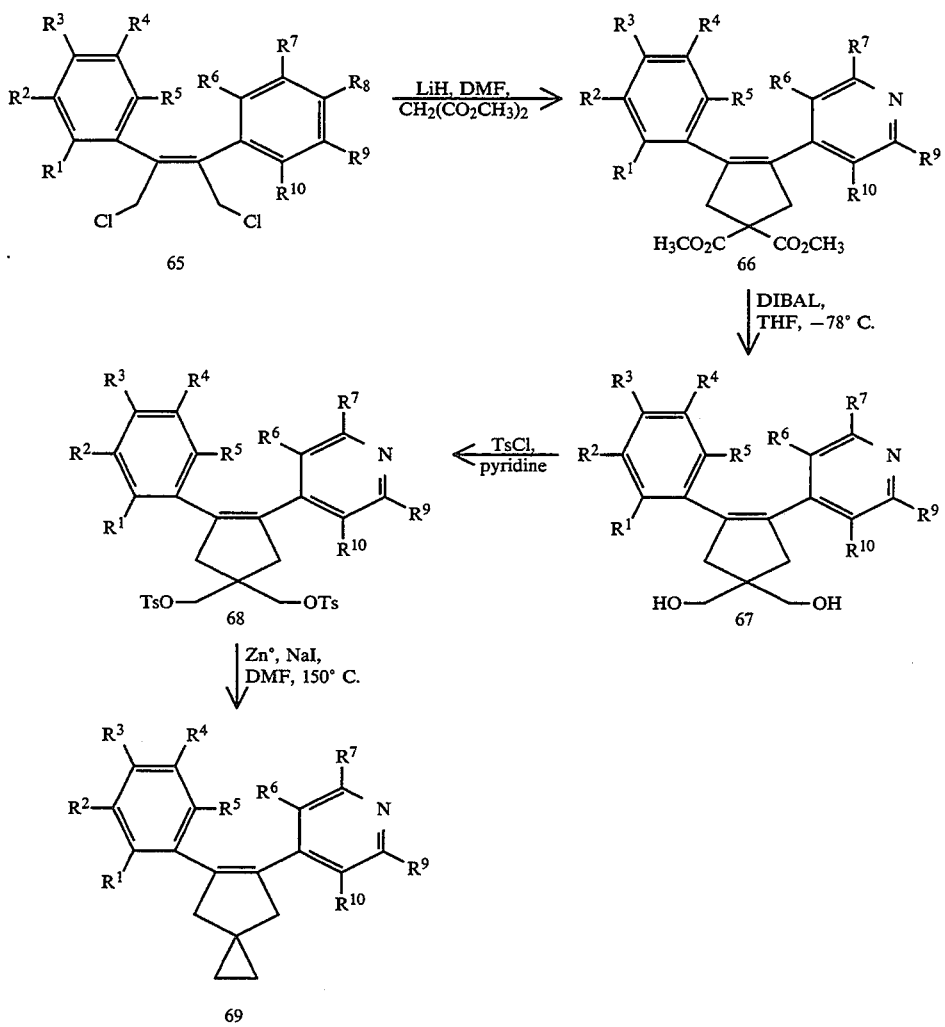

Scheme XIV

Synthetic Scheme XIV shows the four step procedure used to prepare the 5-(4-pyridinyl)-6-arylspiro[2.4-]hept-5-enes 69 from the cis-2-(4-pyridinyl)-3-aryl-1,4-dichloro-2-butenes 65 (prepared in Synthetic Scheme iodide in DMF at 150° C. to give the 5-(4-pyridinyl)-6-arylspiro[2.4]hept-5-ene antiinflammatory agents 69 of this invention.

Scheme XV
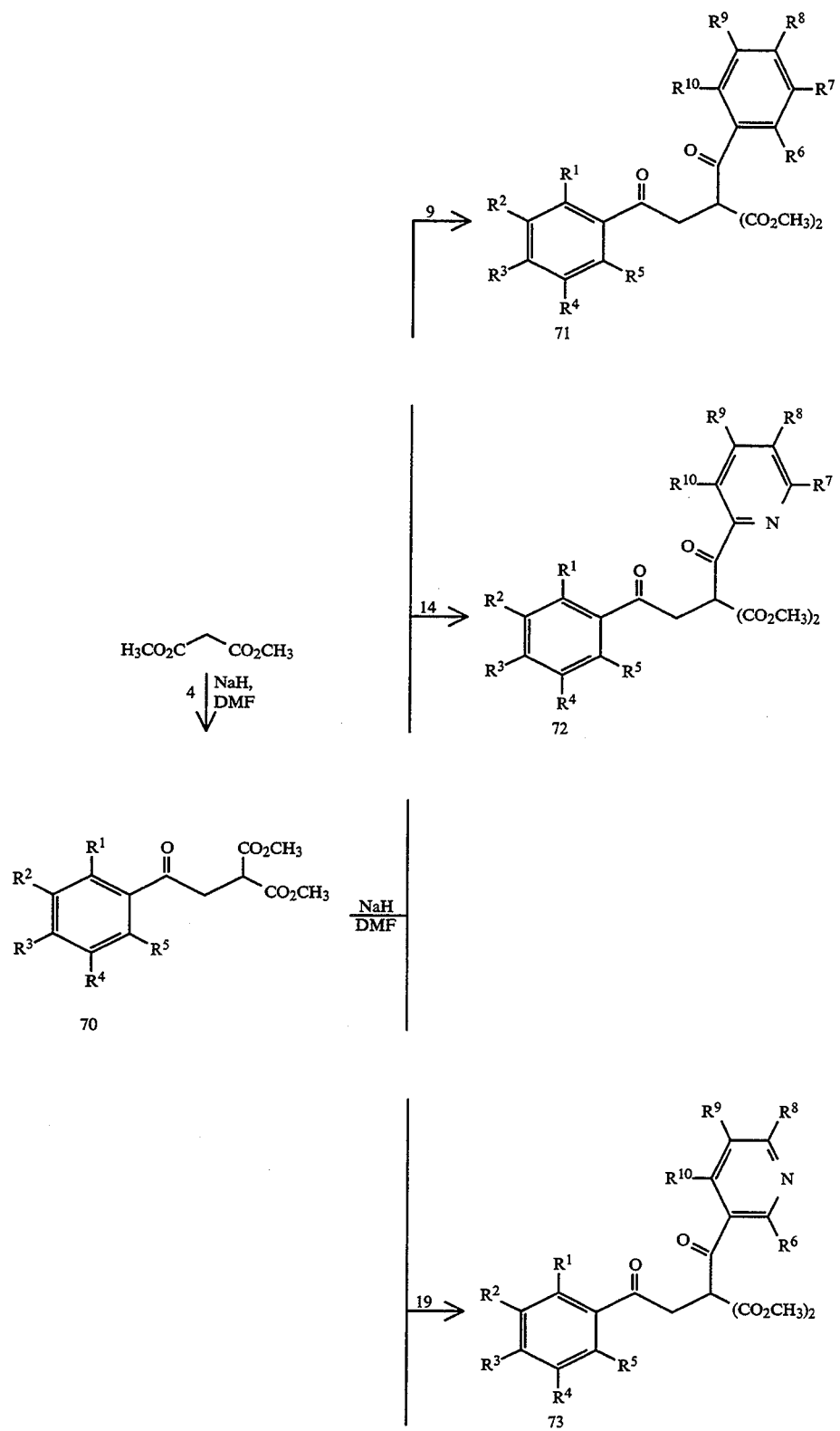

Scheme XV

-continued

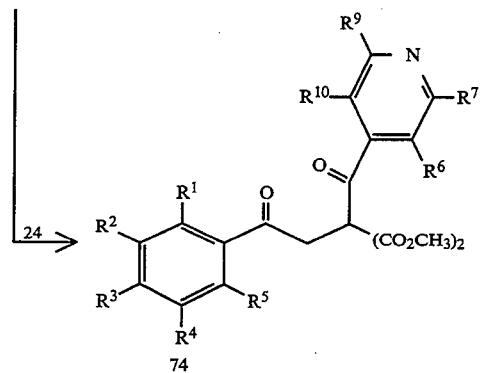

Synthetic Scheme XV shows the two step procedures which can be used to prepare the dialkylated compounds 71, 72, 73, and 74. In step one, dimethyl malonate and sodium hydride in DMF is reacted with the bromoacetophenones 4-(prepared in Synthetic Scheme I) to give the monoalkylated compounds 70. In step two, the monoalkylated compounds 70 are reacted with the bromoacetophenones 9-(prepared in Synthetic Scheme II), the 2-(bromoacetyl)pyridines 14-(prepared in Synthetic Scheme III), the 3-(bromoacetyl)pyridines 19 (prepared in Synthetic Scheme IV), and the 4-(bromoacetyl)pyridines 24 (prepared in Synthetic Scheme V) in DMF in the presence of sodium hydride to give the dialkylated compounds 71, 72, 73, and 74, respectively.

Scheme XVI

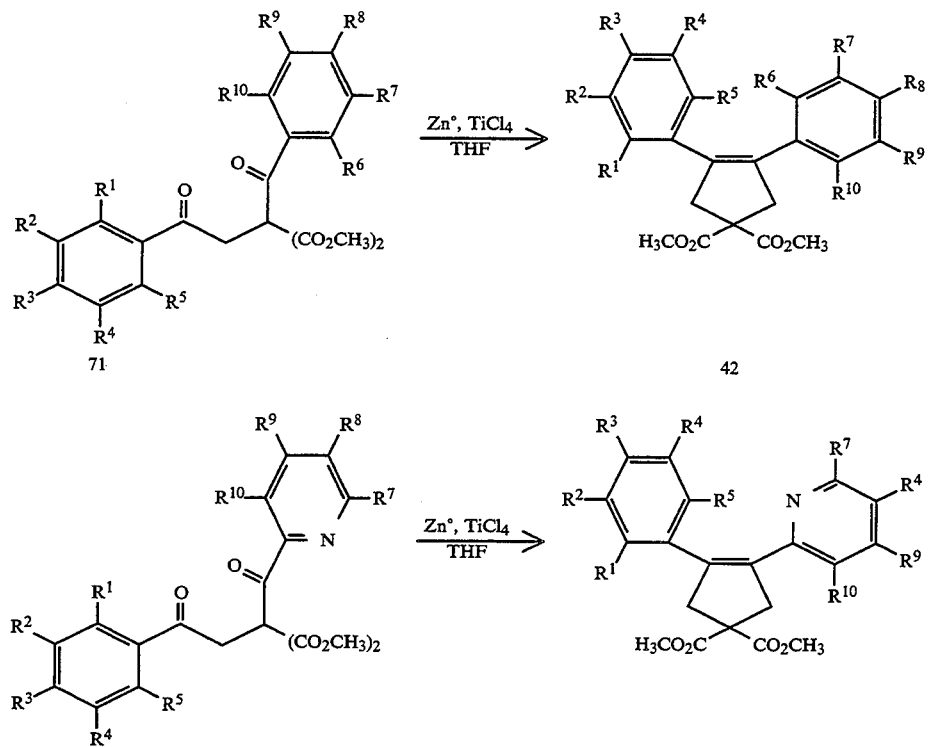

Scheme XVI

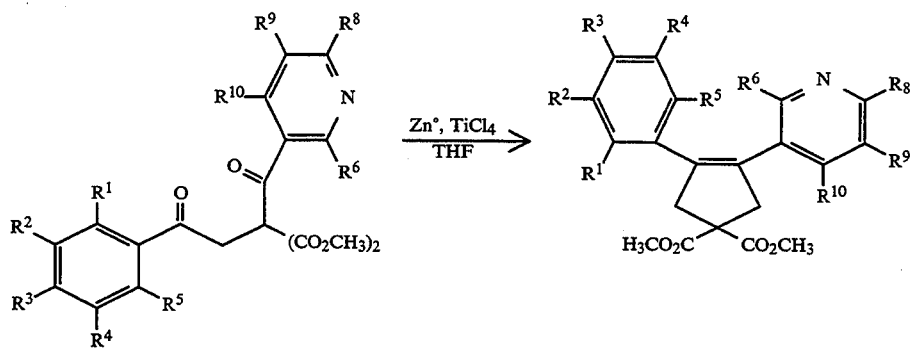

73 → 58

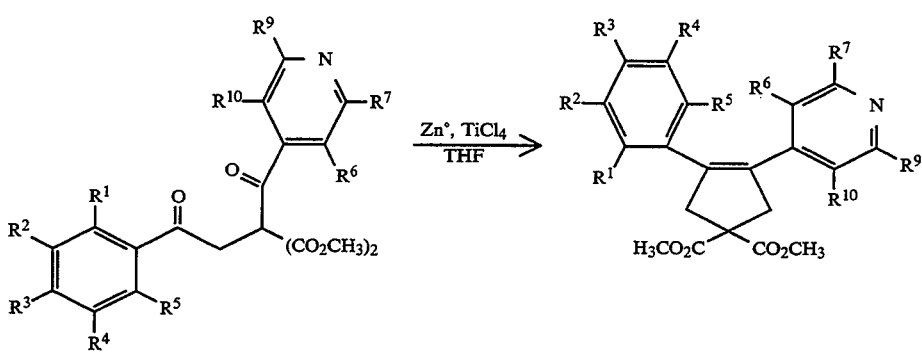

74 → 66

Synthetic Scheme XVI shows alternative procedures which can be used to prepare the 4,4-dicarbomethoxycyclopentenes 42, 50, 58, and 66 from the dialkylated compounds 71, 72, 73, and 74, respectively (prepared in Synthetic Scheme XV). The dialkylated compounds 71, 72, 73, and 74 are reacted with metallic zinc and titanium(IV) chloride in THF to give the 4,4-dicarbomethoxycyclopentenes 42, 50, 58, and 66, respectively. By procedures outlined in Schemes VIII, X, XII, and XIV, 49, 50, 58, and 66 can be converted to the 5,6-diarylspiro[2.4]hept-5-ene antiinflammatory agents 45, 5-(2-pyridinyl)-6-arylspiro[2.4]hept-5-ene antiinflammatory agents 53, 5-(3-pyridinyl)-6-arylspiro [2.4]hept-5-ene antiinflammatory agents 61, and 5-(4-pyridinyl)-6-arylspiro[2.4]hept-5-ene antiinflammatory agents 69, respectively, of this invention.

Scheme XVII

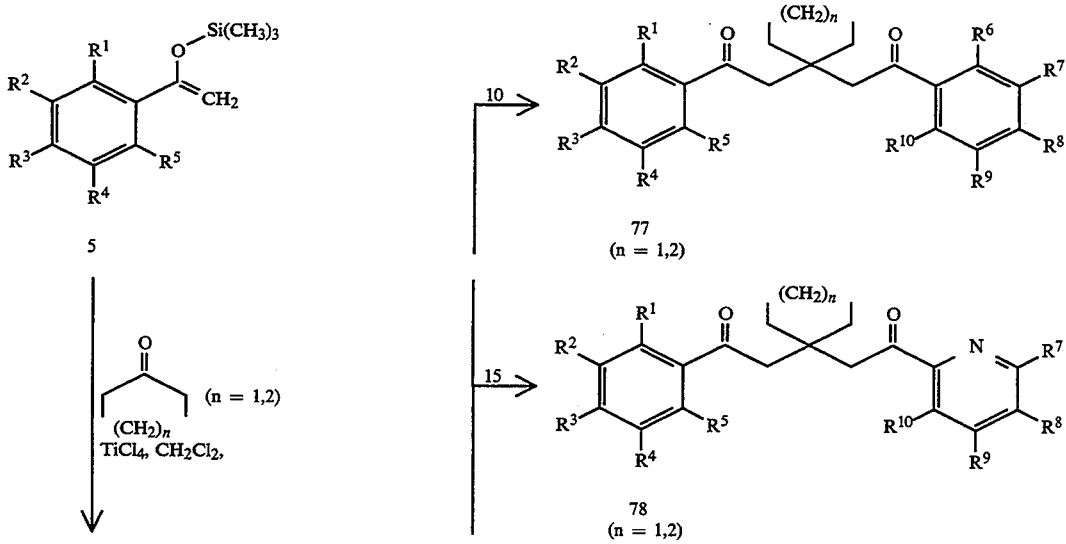

77 (n = 1,2)

78 (n = 1,2)

-continued
Scheme XVII

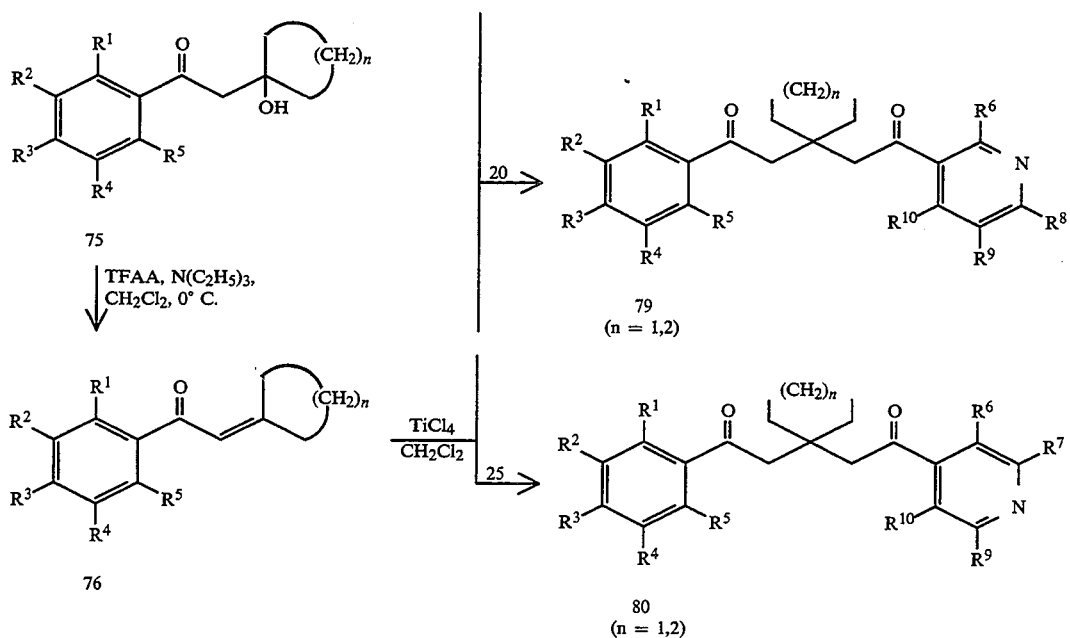

Synthetic Scheme XVII shows the three step procedures used to prepare the cycloalkyldiketones 77, 78, 79 and 80 from the phenyl silyl enol ethers 5 (prepared in Synthetic Scheme I) and cycloalkanones (n=1,2). In step one, the silyl enol ethers 5 are reacted with cycloalkanones (n=1,2) in methylene chloride in the presence of titanium(IV) chloride to give the corresponding cycloalkanols 75. In step two, the cycloalkanols 75 are dehydrated with trifluoroacetic anhydride and triethylamine in methylene chloride at 0° C. to give the corresponding conjugated exocyclic olefins 76. In step three, the olefins 76 are reacted with the phenyl silyl enol ethers 10 (prepared in Synthetic Scheme II), 2-pyridinyl silyl enol ethers 15 (prepared in Synthetic Scheme III), 3-pyridinyl silyl enol ethers 20 (prepared in Synthetic Scheme IV), and 4-pyridinyl silyl enol ethers 25 (prepared in Synthetic Scheme V) to give the cycloalkyldiketones (n=1,2) 77, 78, 79 and 80, respectively.

Scheme XVIII

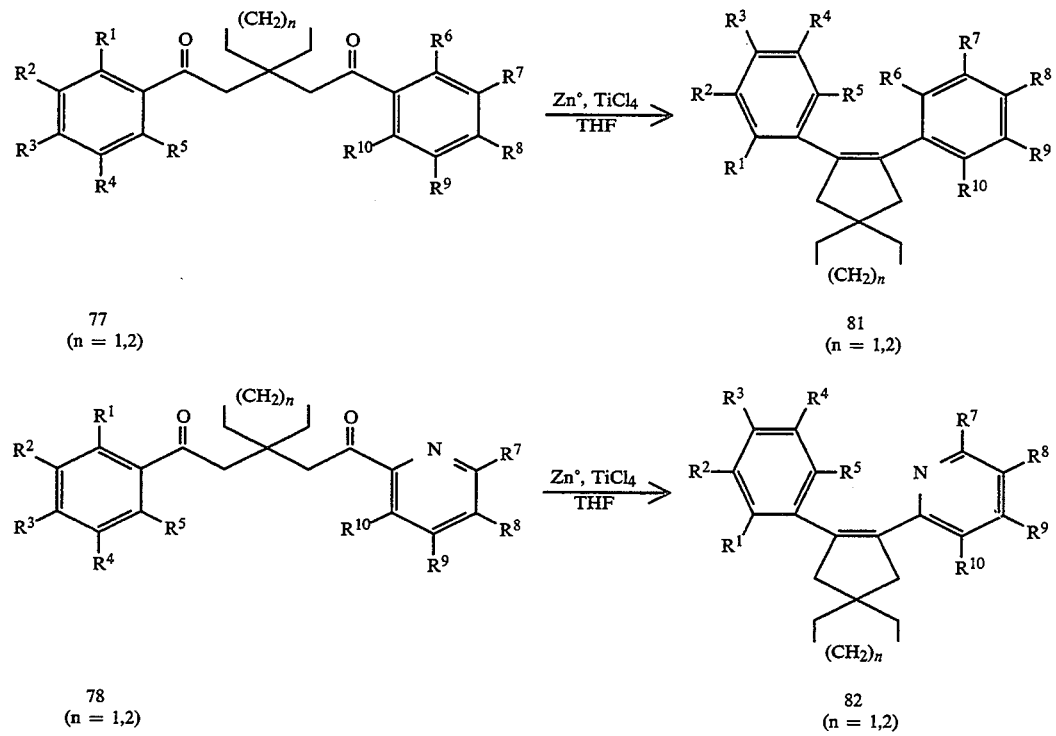

Scheme XVIII (-continued)

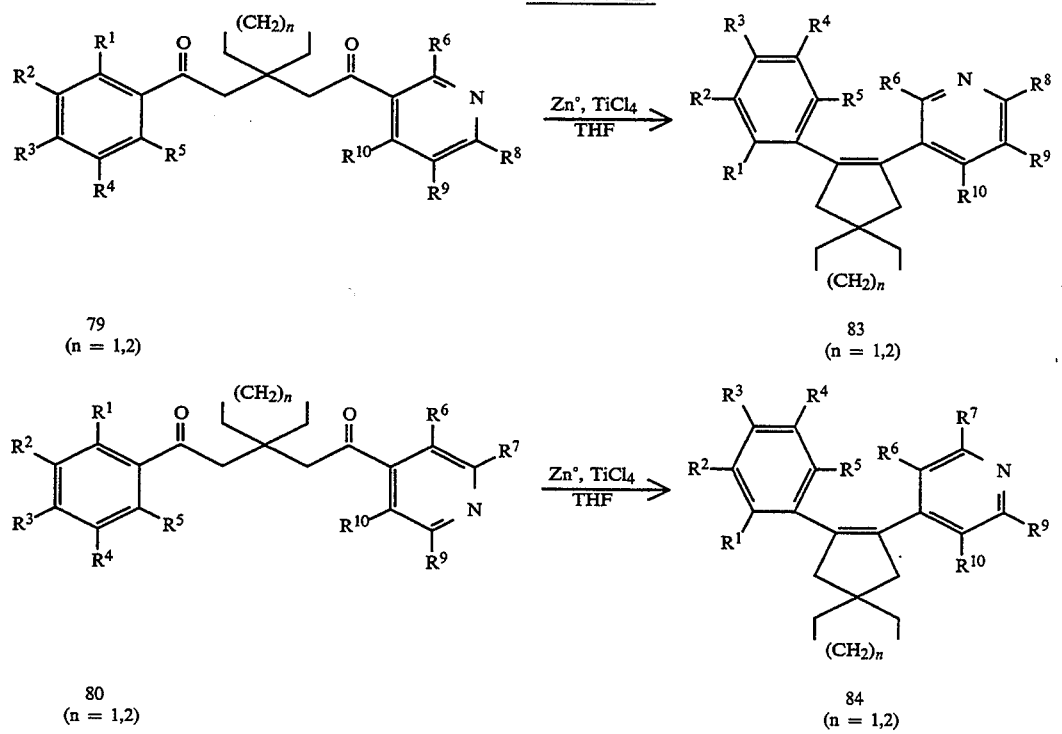

79 (n = 1,2)

80 (n = 1,2)

83 (n = 1,2)

84 (n = 1,2)

Synthetic Scheme XVIII shows the procedures used to prepare 6,7-diarylspiro[3.4]oct-6-enes 81-(n=1) and 2,3-diarylspiro[4.4]non-2-enes 81 (n=2), 6-(2-pyridinyl)-7-arylspiro[3.4]oct-6-enes 82 (n=1) and 2-(2-pyridinyl)-3-arylspiro[4.4]non-2-enes 82 (n=2), 6-(3-pyridinyl)-7-arylspiro[3.4]oct-6-enes 83 (n=1) and 2-(3-pyridinyl)-3-arylspiro[4.4]non-2-enes 83 (n=2), and 6-(4-pyridinyl)-7-arylspiro[3.4]oct-6-enes 84 (n=1) and 2-(4-pyridinyl)-3-arylspiro[4.4]non-2-enes 84 (n=2) from cycloalkyldiketones (n=1,2) 77, 78, 79 and 80, respectively (prepared in Synthetic Scheme XVII). The cycloalkyldiketones (n=1,2) 77, 78, 79 and 80 are reacted metallic zinc and titanium(IV) chloride in THF to give the 6,7-diarylspiro[3.4]oct-6-ene antiinflammatory agents 81 (n=1) and 2,3-diarylspiro[4.4]non-2-ene antiinflammatory agents 81 (n=2), 6-(2-pyridinyl)-7-arylspiro[3.4]oct-6-ene antiinflammatory agents 82 (n=1) and 2-(2-pyridinyl)-3-arylspiro[4.4]non-2-ene antiinflammatory agents 82 (n=2), the 6-(3-pyridinyl)-7-arylspiro[3.4]oct-6-ene antiinflammatory agents 83 (n=1) and 2-(3-pyridinyl)-3-arylspiro[4.4]non-2-ene antiinflammatory agents 83 (n=2), and the 6-(4-pyridinyl)-7-arylspiro[3.4]oct-6-ene antiinflammatory agents 84 (n=1) and 2-(4-pyridinyl)-3-arylspiro [4.4]non-2-ene antiinflammatory agents 84 (n=2), respectively, of this invention.

Scheme XIX

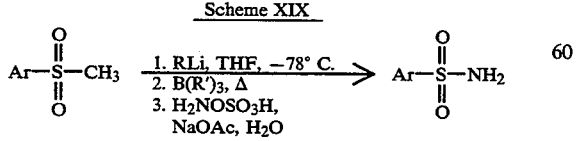

Synthetic Scheme XIX shows the three step procedure used to prepare sulfonamide antiinflammatory agents from their corresponding methyl sulfones. In step one, a THF solution of the methyl sulfones at −78° C. is treated with an alkyllithium reagent, e.g., methyllithium, n-butyllithium, etc. In step two, the anions generated in step one is treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents of this invention.

The following examples contain detailed descriptions of the methods of preparation of compounds of Formula I–VI. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

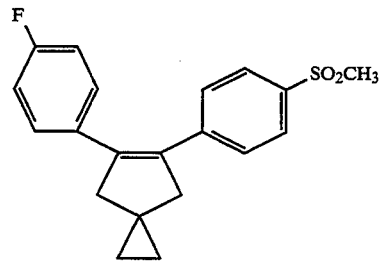

5-(4-Fluorophenyl)-6-(methylsulfonyl)phenyl]spiro[2.4]hept-5-ene

Step 1: Preparation of 4-(methylthio)acetophenone

To a stirred solution of 50 g (340 mmol) of 4-(methylthio)benzonitrile in 2 L of THF at −78° C. under an atmosphere of nitrogen was added 282 mL (390 mmol) of methyllithium (1.4M in diethyl ether) over a period of ten minutes. The solution was stirred at −78° C. for one hour, and then the dry ice bath was removed. After five hours, 100 mL of water followed by 200 mL of 3N hydrochloric acid were added to the reaction mixture and it was stirred overnight. Concentration in vacuo gave a residue which was partitioned between ethyl acetate and water. The water layer was extracted with three portions of ethyl acetate and the combined ethyl acetate layers were dried (MgSO$_4$). Concentration in vacuo gave 58 g of crude (4-methylthio)acetophenone as a solid: NMR (CDCl$_3$) δ 2.52 (s, 3H), 2.57 (s, 3H), 7.26 (d, J=9 Hz, 2H), 7.87 (d, J=9 Hz, 2H).

Step 2:Preparation of 4-(methylsulfonyl) acetophenone

To a solution of 11.73 g (71.1 mmol) of 4-(methylsulfonyl)acetophenone (prepared in Step 1) in 500 mL of dichloromethane at ambient temperature was added 61.14 g (177 mmol) of m-chloroperoxybenzoic acid (50%) (MCPBA) in portions over 20 minutes. The reaction was stirred for two hours, quenched slowly with aqueous sodium bisulfite, washed with three 100 mL portions of saturated sodium bicarbonate, dried (MgSO$_4$), and concentrated in vacuo to give 11.91 g (91%) of (4-methylsulfonyl)acetophenone as a colorless solid: NMR (CDCl$_3$) δ 2.67 (s, 3H), 3.08 (s, 3H), 8.06 (d, J=9 Hz, 2H), 8.14 (d, t=9 Hz, 2H).

Stem 3:Preparation of 2-bromo-4′-(methylsulfonyl) acetophenone

To a stirred solution of 11.91 g (60.5 mmol) of 4-(methylsulfonyl)acetophenone (prepared in Step 2) in 133 mL of glacial acetic acid and 0.11 mL of hydrochloric acid at ambient temperature was added a solution of 8.22 g (51.4 mmol) of bromine in 9.3 mL of glacial acetic acid over a period of three hours. The reaction mixture was diluted with 500 mL of water and extracted with chloroform. The combined extracts were dried (MgSO$_4$) and concentrated in vacuo to give 15.7 g of crude 2-bromo-(4′-methylsulfonyl)acetophenone as a solid: NMR (CDCl$_3$) δ 3.10 (s, 3H), 4.45 (s, 2H), 8.08 (d, J=9 Hz, 2H), 8.17 (d, J=9 Hz, 2H).

Step 4:Preparation of 2-(4-fluorophenyl)-1-[2-[4-(methylsulfonyl)phenyl]-2-oxoethoxy]ethanone To a stirred solution of 4.45 g (28.9 mmol) of 4-fluorophenylacetic acid in 3.26 g (31.8 mmol) of triethylamine and 275 mL of acetonitrile was added 8.9 g (28.9 mmol) of 2-bromo-4′-(methylsulfonyl)acetophenone (prepared in Step 3) at ambient temperature. The reaction mixture was stirred for 30 minutes, concentrated in vacuo, and partitioned between ethyl acetate and water. The organic phase was dried (MgSO$_4$) and concentrated in vacuo. Purification by silica gel chromatography with ethyl acetate/hexane (1:1) gave 6.87 g (68%) of 2-(4-fluorophenyl)-1-[2-[4-(methylsulfonyl) phenyl]-2-oxoethoxy]ethanone as a colorless solid: NMR (CDCl$_3$) δ 3.08 (s, 3H), 3.79 (s, 2H), 5.35 (s, 2H), 7.06 (s, t, J=9 Hz, 2H), 7.32 (dd, J=6and 9 Hz, 2H), 8.06 (s, 4H).

Step 5:Preparation of 3-(4-fluoromhenyl)-4-[(4-methylsulfonyl)phenyl]-5H-furan-2-one Under nitrogen, 4.10 g (11.7 mmol) of 2-(4-fluorophenyl)-1-[2-[4-(methylsulfonyl)phenyl]-2-oxoethoxy]ethanone (prepared in Step 4), 6.52 mL (46.8 mmol) of triethylamine, 4.89 g (25.7 mmol) of p-toluenesulfonic acid, and 12 g of 4 Å molecular sieves were added to 117 mL of acetonitrile and stirred at reflux for 16 hours. The reaction mixture was concentrated in vacuo and the residue partitioned between dichloromethane and water. The dichloromethane layer was dried (MgSO$_4$) and reconcentrated in vacuo. Recrystallization from hexane/ethyl acetate (2: 1) gave 3.65 g (94%) of 3-(4-fluorophenyl)-4-[(4-methylsulfonyl)phenyl]-5H-furan-2-one as a solid: mp 166°-167° C.; NMR (CDCl$_3$) δ 3.08 (s, 3H), 5.19 (s, 2H), 7.10 (t, J=9 Hz, 2H), 7.42 (dd, J=6and 9 Hz, 2H), 7.52 (d, J =9 Hz, 2H), 7.97 (d, J=9 Hz, 2H). HRMS. Calc'd for C$_{17}$H$_{13}$FO$_4$S: 332.0519.Found: 332.0501.Anal. Calc'd for C$_{17}$H$_{13}$FO$_4$S: C, 61.44;H, 3.94; O, 19.26.Found: C, 61.11;H, 4.06; O, 19.32.

Step 6:Preparation of 2-(4-fluorophenyl)-3-[(4-methylsulfonyl)phenyl]-1,4-dihydroxy-2-butene To a solution of 3.08 g (9.28 mmol) of 3-(4-fluorophenyl)-4-[(4-methylsulfonyl)phenyl]-5H -furan-2-one (prepared in Step 5) in 93 mL of tetrahydrofuran (THF) at −78° C. under an atmosphere of nitrogen was added 20 mL (30 mmol) of diisobutylaluminum hydride (DIBAL) (1.5M in THF) over a 10 minute period. The solution was stirred at −78° C. for 20 minutes, allowed to warm to ambient temperature, and stirred overnight. An additional 15 mL (22 mmol) aliquot of DIBAL was added and stirring was continued for 2 hours. The reaction was cooled to −78° C., treated dropwise with 25 mL of acetone, warmed to room temperature, and slowly treated with 25 mL of water. The mixture was stirred for 30 minutes prior to the careful addition of 35 mL of 1.2N sodium hydroxide. The mixture was extracted with ethyl acetate, washed with 1N hydrochloric acid followed by brine, dried (MgSO$_4$), and concentrated in vacuo to give 3.8 g of crude 2-(4-fluorophenyl)-3-[(4-methylsulfonyl)phenyl]-1,4-dihydroxy-2-butene as a colorless oil: NMR (CDCl$_3$) δ 2.98 (s, 3H), 4.60 (d, J=6 Hz, 4H), 6.8 (t, J=9 Hz, 2H), 6,94–7.02 (m, 2H), 7.22 (d, J=9 Hz, 2H), 7.65 (d, J=9 Hz, 2H).

Step 7: Preparation of 2-(4-fluorophenyl)-3-[(4-methylsulfonyl)phenyl]-1,4-dichloro-2-butene To a solution of 3.5 g (7.62 mmol) of crude 2-(4-fluorophenyl)-3-[(4-methylsulfonyl)phenyl]-1,4-dihydroxy-2-butene (prepared in Step 6) in 58 mL of N,N-dimethylformamide (DMF) at 5° C. under an atmosphere of nitrogen was added dropwise 1.52 mL (20.84 mmol) of thionyl chloride. The reaction was stirred at 5° C. for 22 hours, stirred at ambient temperature for an additional 8 hours, and concentrated in vacuo. The residue was partitioned between ethyl acetate and water; the ethyl acetate phase was dried (MgSO$_4$) and concentrated in vacuo to give crude 2-(4-fluorophenyl)-3-[(4methylsulfonyl)phenyl]-1,4-dichloro-2-butene as a solid: NMR (CDCl$_3$) δ 3.0 (s, 3H), 4.55 (d, J=3.4 Hz, 4H), 6.86 (t, J=9Hz, 2H), 6.75 (d, J=8.3Hz, 2H), 7.45 (d, J=9 Hz, 2H).

Step 8, A: Preparation of 1-[2-(4-fluorophenyl)-4,4-dicarbomethoxycyclopenten-1-yl]-4-(methylsulfonyl)benzene To a solution of 1.2 mL (10.5 mmol) of dimethyl malonate in 10 mL of DMF under an atmosphere of nitrogen was added 215 mg (26.9 mmol) of lithium hydride in portions. The resulting suspension was stirred at ambient temperature for 20 minutes prior to the addition of a solution of crude 2-(4-fluorophenyl)-3-[(4-methylsulfonyl)phenyl]-1,4-dichloro-2-butene (prepared in Step 7) in 10 mL of DMF. The reaction was stirred at ambient temperature for 15 hours, treated with another 150 mg (18.8 mmol) of lithium hydride, and stirred for another 4 hours. The mixture was concentrated in vacuo and partitioned between ethyl acetate and water; the organic phase was dried (MgSO4), and concentrated in vacuo. The residue was chromatographed on silica gel to give 1.1 g (34%) of 1-[2-(4-fluorophenyl)-4,4dicarbomethoxycyclopenten-1-yl]-4-(methylsulfonyl) benzene as an oil: NMR (CDCl3) δ 3.03 (s, 3H), 3.55 (s, 4H), 3.79 (s, 6H), 6.93 (t, J=9 Hz, 2H), 7.11 (dd, J=6and 9 Hz, 2H), 7.32 (d, J=9 Hz, 2H), 7.77 (d, J=9 Hz, 2H).

Step 8, B: Preparation of 1-[2-(4-fluorophenyl)-4,4- dicarbomethoxycyclopenten-1-yl]-4-(methylsulfonyl)- benzene To a solution of 7.18 mL (63 mmol) of dimethyl malonate in 160 mL of DMF at 0° C. under an atmosphere of nitrogen was added 3.0 g (75 mmol) of sodium hydride (60% suspension in oil). The reaction was stirred at ambient temperature for 15 minutes (or until the gas evolution has ceased), cooled to −20° C., and treated with 15 g (69 mmol) of 2-bromo-4'-fluoroacetophenone (Aldrich) in one portion. The mixture was stirred at ambient temperature for 1 hour and then cooled to 0° C.; another 75 mmol of sodium hydride was added and the resulting mixture stirred at ambient temperature for 15 minutes (or until the gas evolution has ceased). The reaction was recooled to −20° C. and treated with 19.1 g (69 mmol) of 2-bromo-4'-(methylsulfonyl)acetophenone (prepared in Step 3). The reaction was stirred at room temperature for 2 hours and concentrated in vacuo. The residue was partitioned between water and ethyl acetate; the ethyl acetate phase was dried (MgSO4) and reconcentrated in vacuo. The residue was chromatographed on silica gel to give 13.8 g (51%) of dimethyl2-[2-(4-fluorophenyl)-2-oxoethyl]-2-[2-[4-(methylsulfonyl)phenyl]-2-oxoethyl]propanedioate as an oil: NMR (CDCl3) δ 3.06 (s, 3H), 3.76 (s, 6H), 4.03 (s, 2H), 4.08 (s, 2H), 7.13 (t, J=8.6 Hz, 2H), 7.97–8.05[m with d at 8.03 (J=8.7 Hz), 4H], 8.14 (d, J=8.5 Hz, 2H).

To a vigorously stirred mixture of 50.4 g (771 mmol) of zinc dust in 640 mL of THF at −78° C. under an atmosphere of nitrogen was added dropwise 60.4 mL (551 mmol) of titanium(IV) chloride. The reaction was warmed to ambient temperature with a water bath and then stirred at reflux for 1 hour. To the resulting dark mixture under reflux was added a solution of 15 g (32.3 mmol) of dimethyl2-[2-(4-fluorophenyl)-2-oxoethyl]-2-[2-[4-(methylsulfonyl)phenyl]-2-oxoethyl ]propanedioate (prepared above) in 20 mL of THF. The resulting mixture was stirred at ambient temperature for 16 hours, filtered through a pad of celite, rinsed with ethyl acetate, and concentrated in vacuo. The residue was partitioned between water and ethyl acetate; the organic phase was washed with brine, dried (MgSO4), and concentrated in vacuo. The residue was chromatographed on silica gel to give 6.26 g (44%) of 1-[2-(4-fluorophenyl)-4,4-dicarbomethoxycyclopenten-1-yl]-4-(methylsulfonyl)benzene which was identical to the material prepared in Step 8, Method A.

Step 9: Preparation of 1-[2-(4-fluorophenyl)-4,4-di(-hydroxymethyl)cyclopenten-1-yl]-4-(methylsulfonyl)-benzene Under nitrogen, a solution of 1.01 g (2.34 mmol) of 1-[2-(4-fluorophenyl)-4,4-dicarbomethoxycyclopenten-1-yl]-4-(methylsulfonyl)benzene (prepared in Step 8) in 1.5 mL of THF at −78° C. was treated with 11.6 mL (11.6 mmol) of DIBAL (1.0M in THF). The reaction was stirred at ambient temperature for 1.5 hours, quenched with acetone and aqueous NaOH, extracted with ethyl acetate, dried (MgSO4), and concentrated in vacuo to give 840 mg of crude 1-[2-(4-fluorophenyl)-4,4-di(hydroxymethyl)cyclopenten-1-yl]-4-(methylsulfonyl)benzene as a colorless oil: NMR (CDCl3) δ 2.82 (d, J=5 Hz, 4H), 3.04 (s, 3H), 3.86 (d, J=5 Hz, 4H), 6.94 (t, J=9 Hz, 2H), 7.11 (dd, J=5 and 9 Hz, 2H), 7.33 (d, J=9 Hz, 2H), 7.77 (d, J=9 Hz, 2H).

Step 10: Preparation of 1-[2-(4-fluorophenyl)-4,4-di(-tosylmethyl)cyclopenten-1-yl]-4-(methylsulfonyl)benzene Under nitrogen, a solution of 2.34 mmol of the crude 1-[2-(4-fluorophenyl)-4,4-di(hydroxymethyl)cyclopenten-1-yl]-4-(methylsulfonyl)benzene (prepared in Step 9) in 8 mL of pyridine at ambient temperature was treated with 1.2 g (6.3 mmol) of p-toluenesulfonyl chloride (tosyl chloride). The resulting solution was stirred at room temperature for 17 hours, concentrated in vacuo, and chromatographed on silca gel to give 1.06 g (66% overall yield from Step 9) of 1-[2-(4-fluorophenyl)-4,4-di(tosylmethyl)cyclopenten-1-yl]-4-(methylsulfonyl)-benzene as a colorless solid: NMR (CDCl3) δ 2.46 (s, 6H), 2.73 (s, 3H), 3.04 (s, 3H), 4.05 (s, 4H), 6.85–7.0 (m, 4H), 7.20 (d, J=8 Hz, 2H), 7.34 (d, J=8 Hz, 4H), 7.75 (d, J=8 Hz, 6H).

Step 11: Preparation of 5-(4-fluorophenyl)-6-[4-(methylsulfonylphenyl]spiro[2,4]hept-5-ene Under nitrogen, a solution of 1.02 g (1.49 mmol) of 1-[2-(4-fluorophenyl)-4,4-di(tosylmethyl)cyclopenten-1-yl]-4-(methylsulfonyl)benzene (prepared in Step 10) in 24 mL of DMF was treated with 3.23 g (21.55 mmol) of sodium iodide and 1.61 g (24.63 mmol) of zinc dust. The reaction was stirred at 150° C. for 1.5 hour, concentrated in vacuo, and partitioned between water and ethyl acetate. The organic phase was washed with sodium sulfite, water, brine, dried (MgSO4), and concentrated in vacuo. The residue was chromatographed on silica gel to give 437 mg (86%) of 5-(4-fluorophenyl)-6-[4-(methylsulfonyl)phenyl]spiro[2.4]hept-5-ene as a colorless solid: mp 140.5°–142.0° C.; NMR (CDCl3) δ 0.69 (s, 4H), 2.92 (s, 4H), 3.04 (s, 3H), 6.93 (t, J=9 Hz, 2H), 7.10 (dd, J=5 and 9 Hz, 2H), 7.32 (d, J=8 Hz, 2H), 7.76 (d, J=8 Hz, 2H). HRMS. Calc'd for $C_{20}H_{19}FO_2S$: 342.1090.Found: 342.1126.Anal. Calc'd for $C_{20}H_{19}FO_2S$: C, 70.15; H, 5.59; F, 5.55; S, 9.36.Found: C, 70.10; H, 5.69; F, 5.50; S, 9.60.

EXAMPLE 2

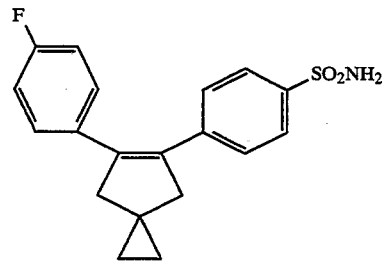

4-[6-(4-Fluorophenyl)spiro[2.4]hept-5-en-5-yl]benzenesulfonamide

Under nitrogen, a solution of 90 mg (0.248 mmol) of 5-(4-fluoro phenyl)-6-[4-(methylsulfonyl)phenyl]-spiro[2.4]hept-5-ene (the title compound of Example 1) in 1 mL of THF at −78° C. was treated with 0.21 mL (0.27 mmol) of methyllithium (1.3M in ether) over a period of 2 minutes. The reaction was stirred at ambient temperature for 25 minutes, cooled to −78° C., and treated with 0.3 mL (0.3 mmol) of tributylborane (1.0M in THF). The resulting dark brown solution was stirred at ambient temperature for 20 minutes and then at reflux for 16 hour prior to the addition of 350 mg (4.27 mmol) of sodium acetate, 2 mL of water, and 250 mg (2.21 mmol) of hydroxyamine-O-sulfonic acid. The resulting light orange mixture was stirred at ambient temperature for 3 hours and the aqueous phase extracted with ethyl acetate. The combined extracts were washed with water, brine, dried (MgSO$_4$), and concentrated in vacuo. The residue was chromatographed on silica gel to give 24 mg (27%) of 4-[6-(4-fluorophenyl)spiro[2.4]hept-5-en-5-yl]benzenesulfonamide as a colorless solid: mp 131.0°–133.0° C.; NMR (CDCl$_3$) δ 0.68 (s, 4H), 2.90 (s, 3H), 4.81 (s, 2H), 6.92 (t, J=9 Hz, 2H), 7.11 (dd, J=6and 9 Hz, 2H), 7.27 (d, J=9 Hz, 2H), 7.74 (d, J=9 Hz, 2H). HRMS. Calc'd for C$_{19}$H$_{18}$FNO$_2$S: 344.1121.Found: 344.1122.Anal. Calc'd for [C$_{19}$H$_{18}$FNO$_2$S+0.1 CH$_3$CO$_2$CH$_2$CH$_3$]: C, 66.16; H, 3.98; S, 9.11. Found: C, 65.86; H, 5.52; N, 3.92; S, 9.57.

EXAMPLE 3

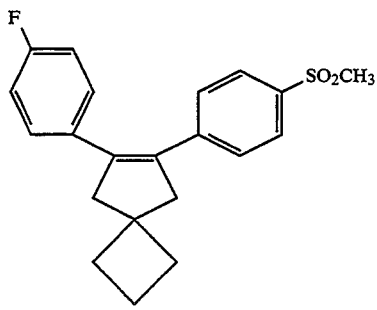

6-(4-Fluorophenyl)-7-[4-(methylsulfonyl)phenyl]-spiro[3.4]oct-6-ene

Step 1:Preparation of 1-methylthio-4-[1-[(trimethylsilyl)oxy]ethenyl]benzene

Under nitrogen, 11.0 g (66.2 mmol) of 4-(methylthio)acetophenone (prepared in Step 1 of Example 1) and 13.8 mL (99 mmol) of triethylamine in 50 mL of acetonitrile was treated with 12.6 mL (99.3 mmol) of chlorotrimethylsilane at ambient temperature and allowed to stir for 20 minutes prior to the slow addition of a suspension of 14.9 g (99.4 mmol) of sodium iodide in 60 mL of acetonitrile. The reaction was stirred for 3 hours, poured into ice/water, and extracted with hexane. The extracts were combined, dried (K$_2$CO$_3$), and concentrated in vacuo to give 16 g of crude 1-methylthio-4-[1[(trimethylsilyl)oxy]ethenyl]benzene as an oil: NMR (CDCl$_3$) δ 0.26 (s, 9H), 2.48 (s, 3H), 4.39 (d, J=2 Hz, 1H), 4.87 (d, J=2 Hz, 1H), 7.20 (d, J=8 Hz, 2H), 7.50 (d, J=8Hz, 2H).

Step 2:Preparation of 1-fluoro-4-[1-[(trimethylsilyl)oxy]ethenyl]benzene

Under nitrogen, 17.7 g (128 mmol) of 4-fluoroacetophenone (Aldrich) and 20.7 mL (192 mmol) of triethylamine at ambient temperature was treated with 24.4 mL (192.3 mmol) of chlorotrimethylsilane and allowed to stir of 20 minutes prior to the slow addition of a suspension of 30 g (200 mmol) of sodium iodode in 200 mL of acetonitrile. The extracts were combined, dried (K$_2$CO$_3$), and concentrated in vacuo to give 27 g of crude 1-fluoro-4-[1[(trimethylsilyl)oxy]ethenyl]benzene as an oil: NMR (CDCl$_3$) δ 0.28 (s, 9H), 4.41 (d, J=2 Hz, 1H), 4.84 (d, J=2 Hz, 1H), 7.00 (d, J=8 Hz, 2H), 7.53 –7.60 (m, 2H).

Step 3: Preparation of 1-(4-fluorophenyl)-2-(1-hydroxycyclobutan-1-yl)ethan-1-one Under nitrogen, 11.0 g (100 mmol) of titanium(IV) chloride in 140 mL of methylene chloride at 0° C. was slowly treated with a solution of 8.2 mL (110 mmol) of cyclobutanone in 30 mL of methylene chloride prior to the dropwise addition of a solution of 21.1 g (100 mmol) of 1-fluoro-4-[1[(trimethylsilyl)oxy]ethenyl]benzene (obtained from Step 2) in 15 mL of methylene chloride. The reaction was stirred for 15 minutes and then poured into 200 mL of ice/water; the phases were separated. The aqueous phase was extracted twice with 30 mL of methylene chloride and combined with the original methylene chloride phase. The combined extracts were washed 3 times with 120 mL of saturated sodium carbonate/water (1:1) and once with brine, dried (MgSO$_4$), and concentrated in vacuo to give 20.4 g (98%) of crude 1-(4-fluorophenyl)-2-(1-hydroxycyclobutan-1-yl) ethan-1-one as an oil: NMR (CDCl$_3$) δ 1.53–1.70 (m, 1H), 1.80 –1.94 (m, 1H), 1.99–2.10 (m, 2H), 2.17–2.31 (m, 2H), 3.31 (s, 2H), 7.10–7.19 (m, 2H), 7.95–8.03 (m, 2H).

Step 4: Preparation of 1-(4-fluorophenyl)-2-(cyclobutanyliden-1-yl)ethan-1-one

Under nitrogen, 20.3 g (98 mmol) of 1-(4-fluorophenyl)-2-(1-hydroxycyclobutan-1-yl)ethan-1-one (prepared in Step 3), 37 mL (260 mmol) of triethylamine, and 50 mg of 4-dimethylaminopyridine (DMAP) in 80 mL of methylene chloride at 0° C. was slowly treated with a solution of 16.6 mL (118 mmol) of trifluoroacetic anhydride (TFAA) in 40 mL of methylene chloride. The reaction was allowed to stir for 3 hours at 0° C. and then allowed to warm to ambient temperature to stir for an additional 3 hours prior to the addition of 200 mL of saturated sodium carbonate/water (1:1) and 300 mL of ether. The phases were separated and the aqueous phase was extracted twice with 100 mL of ether. The ether extracts were combined with the original ether/methylene chloride phase and washed with brine, dried (MgSO$_4$), and concentrated in vacuo. Purification by silica gel chromatography (Waters Prep-500A) with ethyl acetate/hexane (2:98) gave 12.1 g (65%) of 1-(4-fluorophenyl)-2-(cyclobutanyliden-1-yl)ethan-1-one as an oil: NMR (CDCl$_3$) δ 2.11–2.24 (m, 2H), 2.95 (t, J=8 Hz, 2H), 3.19–3.29 (m, 2H), 2.68–2.74 (m, 1H), 7.05–7.16 (m, H), 7.84–7.97 (m, 2H).

Step 5:Preparation of 1-(4-fluorophenyl)-2-[1-[2-[4-(methylthio)phenyl]-2oxoethyl]cyclobutan-1-yl]ethan-1-one Under nitrogen, 7.2 mL (70.2 mmol) of titanium(IV) chloride in 100 mL of methylene chloride at −78° C. was slowly treated with a solution of 12.1 g (63.8 mmol) of 1-(4-fluorophenyl)-2-(cyclobutanyliden-1-yl)ethan-1-one (prepared in Step 4) in 30 mL of methylene chloride. The reaction was stirred at −78° C. for 1 hour, poured into a solution of 22 g of sodium carbonate in 160 mL of water, and filtered through celite. The phases were separated and the aqueous phase extracted twice with 40 mL of methylene chloride. The extracts were combined with the original methylene chloride phase and washed with brine, dried (MgSO$_4$), and concentrated in vacuo. Purification by silica gel chromatography (Waters Prep-500A) with ethyl acetate/hexane (10:90) gave 1-(4-fluorophenyl)-2-[1-[2-[4-(methylthio)phenyl]-2-oxoethyl]cyclobutan-1-yl]ethan-1-one as an oil: NMR (CDCl$_3$) δ 1.91–2.04 (m, 2H), 2.11 (t, J=8 Hz, 4H), 2.49 (s, 3H), 3.48 (s, 2H), 3.49 (s, 2H), 7.08 (t, J=8

Hz, 2H), 7.23 (t, J=8 Hz, 2H), 7.84 (d, J=9 Hz, 2H), 7.91-7.99 (m, 2H).

Step 6:Preparation of 1-(4-fluorophenyl)-2-[1-[2-[4-(methylsulfonyl)phenyl]-2-oxoethyl]cyclobutan-1-yl]ethan-1-one A solution of 18.3 g (51.4 mmol) of 1-(4-fluorophenyl)-2-[1-[2-[4-(methylthio)phenyl ]-2-oxoethyl]cyclobutan-1-yl]ethan-1-one (prepared in Step 5) in 200 mL of chloroform at 10° C. was slowly treated with 35.6 g (ca. 103 mmol) of solid m-chloroperbenzoic acid (50-60%). The reaction was allowed to stir for 30 minutes and treated with aqueous sodium bisulfite. The chloroform was removed in vacuo and the residue partitioned between ethyl acetate and water. The ethyl acetate extracts were washed 3times with saturated sodium bicarbonate and once with brine, dried (MgSO4), and concentrated in vacuo to give 19.27 g (97%) of 1-(4-fluorophenyl)-2-[1-[2-[4-(methylsulfonyl)phenyl -2-oxoethyl cyclobutan 1-yl]ethan1-one as an oil: NMR (CDCl3) δ 1.95-2.06 (M, 2H), 2.11 (t, J=7 Hz, 4H), 3.05 (s, 3H), 3.52 (s, 2H), 3.59 (s, 2H), 7.09 (t, J=9 Hz, 2H), 7.92-8.04 (m, 4H), 8.19 (d, J=9 Hz, 2H).

Step 7: Preparation of 6-(4-fluorophenyl)-7-[4-(methylsulfonyl)phenyl]spiro[3.4]oct-6-ene Under nitrogen, 16.3 mL (149 mmol) of titanium(IV) chloride was slowly added to a suspension of 19.5 g (298 mmol) of zinc dust in 500 mL of anhydrous THF at −78° C. The resulting mixture was allowed to warm to ambient temperature and then to stir at reflux for 45 minutes. The reaction was cooled to ambient temperature prior to the addition of 19.27 g (49.6 mmol) of neat 1-(4-fluorophenyl)-2-[1-[2-[4-(methylsulfonyl)phenyl]-2-oxoethyl]cyclobutan-1-yl]ethan-1-one (prepared in Step 6) by syringe. The reaction was allowed to stir at ambient temperature overnight, filtered through celite, and concentrated in vacuo. The residue was partitioned between ethyl acetate and water; the ethyl acetate phase was washed with brine, dried (MgSO4), and concentrated in vacuo. Purification by silica gel chromatography (Waters Prep-500A) with ethyl acetate/hexane (20:80) gave 13.5 g (76%) of 6-(4-fluorophenyl)-7-[4-(methylsulfonyl)phenyl]spiro[3.4]oct-6-ene as a colorless solid: mp 123-124° C.; NMR (CDCl3) δ 1.85-1.98 (m, 2H), 2.08 (t, J=7 Hz, 4H), 2.98 (s, 4H), 3.04 (s, 3H), 6.92 (t, J=9 Hz, 7.05-7.13 (m, 2H), 7.30 (t, J=8HZ, 2H), 7.75 (t, J=8 Hz, 2H). MS (FAB) m/e 357 (M+H). Anal. Calc'd for C21H21FO2S: C, 70.76; H, 5.94; F, 5.53; S, 8.99. Found: C, 70.76; H, 6.10; F, 5.20; S, 8.96.

EXAMPLE 4

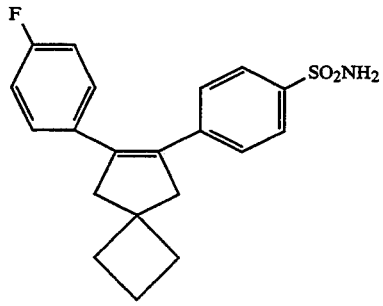

4-[7-(4-Fluorophenyl)spiro[3.4]oct-6-en-6-yl]benzenesulfonamide

Following a procedure similar to the one described in Example 2, 1.76 g (4.94 mmol) of 6-(4-fluorophenyl)-7-[4-(methylsulfonyl)phenyl]spiro[3.4]oct-6-ene (the title compound of Example 3) was converted to 1.61 g of crude sulfonamide. Purification by silica gel chromatography with ethyl acetate/hexane (20:80) and subsequent recrystallization from chloroform/hexane gave 970 mg (55%) of 4-[7-(4-fluorophenyl)spiro[3.4]oct-6-en-6-yl]benzenesulfonamide as a colorless solid: mp 118°-119° C.; NMR (CDCl3) δ 1.92 (m, J=8 Hz, 2H), 2.08 (t, J=7 Hz, 4H), 2.97 (s, 3H), 4.74 (s, 2H), 6.92 (t, J=9 Hz, 2H), 7.06-7.13 (m, 2H), 7.23-7.30 (m, 2H), 7.74 (t, J=8 Hz, 2H). MS (EI) m/e (rel intensity)-357 (100), 329 (48), 248 (66), 233 (44), 109 (32). Anal, Calc'd for C20H20FNO2S: C, 67.21; H, 5.64; N, 3.93; F, 5.32; S, 8.97. Found: C, 66.83; H, 5 .89; N, 3.83; F, 4.96; S, 9.03.

EXAMPLE 5

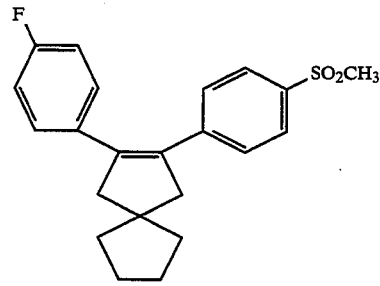

2-(4-Fluorophenyl)-3-[4-(methylsulfonyl)phenyl]-spiro[4.4]non-2-ene

Following a procedure similar to the one described in Example 3with the substitution of cyclopentanone for cyclobutanone, 23 mg of 2-(4-fluorophenyl)-3-[4-(methylsulfonyl)phenyl]spiro[4.4]non-2-ene was obtained as a colorless solid: mp 142°-143° C.; NMR (CDCl3) δ 1.72 (s, 8H), 2.83 (s, 4H), 3.04 (s, 3H), 6.93 (t, J=9 Hz, 2H), 7.10 (dd, J=5and 9 Hz, 2H), 7.31 (d, J=9 Hz, 2H), 7.76 (d, J=9 Hz, 2H). HRMS. Calc'd for C22H23FO2S:370. 1403. Found: 370. 1411. Anal. Calc'd for C22H23FO2S: C, 71.32; H, 6.26; F, 5.13; S, 8.65. Found: C, 71.66; H, 6.36; F, 4.91; S, 9.13.

BIOLOGICAL EVALUATION

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-*

*steroidal Anti-Inflammatory Drugs*, (J. Lombardino, ed. 1985)). Results are shown in Table I.

Rat Carrageenan-induced Analgesia Test

The rat carrageenan analgesia test was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 10 mg/kg body weight |
|---|---|---|
| 1 | 32 | 15 |
| 2 | 57 | 34 |
| 3 | 24 | — |
| 4 | 17 | — |

Evaluation of COX I and COX II activity in vitro a. Preparation of recombinant cox baculoviruses A 2.0 kb fragment containing the coding region of either human or murine COX-I or human or murine COX-II was cloned into a BamH1 site of the baculovirus transfer vector pVL1393 to generate the baculovirus transfer vector. Recombinant baculoviruses were isolated by transfecting 4 μg of baculovirus transfer vector DNA into SF9 cells (2×10e8) along with 200 ng of linearized bacium phosphate method. Recombinant viruses were purified by three rounds of plaque purification and high titer (10E7-10E8 pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% CHAPS. The homogenate was centrifuged at 10,000xG for 30 minutes, and the resultant supernatant was stored at −80° C. before being assayed for COX activity.

b. Assay for COX I and COX II activity:

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μl indomethacin. The $PGE_2$ formed was measured by standard ELISA technology (Cayman Chemical). Results are shown in Table II.

TABLE II

| Examples | COX I $ID_{50}$ μM | COX II $ID_{50}$ μM |
|---|---|---|
| 1 | 14 | <.1 |
| 2 | .2 | <.1 |
| 3 | >100 | <.1 |
| 4 | .9 | <.1 |
| 5 | >100 | <.1 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

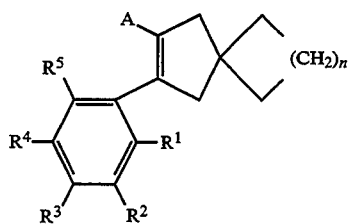

I wherein A is selected from

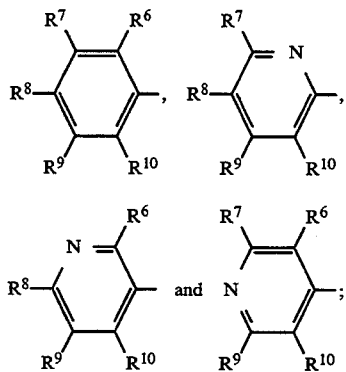

wherein each of $R^1$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

2. Compound of claim 1 wherein each of $R^1$, $R^2$, $R^4$ through $R^7$, $R^9$ and $R^{10}$ is independently selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto; and wherein $R^3$ is selected from lower alkylsulfonyl, lower haloalkylsulfonyl and sulfamyl, and $R^8$, if present, is selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto; or wherein further, $R^3$ is selected from hydrido, halo, lower alkyl, lower alkoxy, lower alkylthio, cyano, lower haloalkyl, lower haloalkoxy, lower hydroxyalkyl, lower alkoxyalkyl, hydroxyl and mercapto, and $R^8$ is selected from lower alkylsulfonyl, lower haloalkylsulfonyl and sulfamyl; or a pharmaceutically-acceptable salt thereof.

3. Compound of claim 2 wherein each of $R^1$, $R^2$, $R^4$ through $R^7$, $R^9$ and $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; and wherein $R^3$ is selected from methylsulfonyl, fluoromethylsulfonyl, difluoromethylsulfonyl, trifluoromethylsulfonyl and sulfamyl, and $R^8$, if present, is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; or wherein further $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl, and $R^8$ is selected from methylsulfonyl, fluoromethylsulfonyl, difluoromethylsulfonyl, trifluoromethylsulfonyl and sulfamyl; or a pharmaceutically-acceptable salt thereof.

4. A compound of Formula II

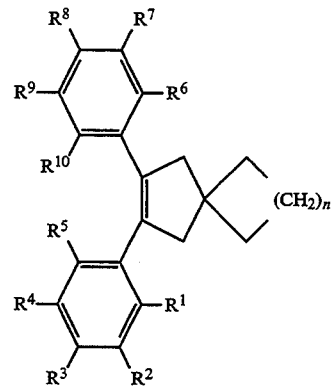

II wherein each of $R^1$ through $R^{10}$ is independently selected from hydrido, halo, alkyl, alkoxy, alkylthio, cyano, haloalkyl, haloalkoxy, hydroxyalkyl, alkoxyalkyl, hydroxyl, mercapto, alkylsulfonyl, haloalkylsulfonyl and sulfamyl; and wherein n is a number selected from 0, 1, 2 and 3; or a pharmaceutically-acceptable salt thereof.

5. Compound of claim 4 wherein n is a number selected from 0, 1 and 2; wherein each of $R^1$, $R^2$ and $R^4$ through $R^{10}$ is independently selected from hydrido, halo, lower alkyl, lower alkylthio, cyano, lower haloalkyl, lower haloalkoxy, lower alkoxy, hydroxyl, mercapto, lower hydroxyalkyl and lower alkoxyalkyl; and wherein $R^3$ is selected from lower alkylsulfonyl, lower haloalkylsulfonyl and sulfamyl; or a pharmaceutically-acceptable salt thereof.

6. Compound of claim 5 wherein each of $R^1$, $R^2$ and $R^4$ through $R^{10}$ is independently selected from hydrido, fluoro, chloro, bromo, iodo, methyl, ethyl, propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, hydroxymethyl, methoxymethyl and ethoxymethyl; and wherein $R^3$ is selected from methylsulfonyl, fluoromethylsulfonyl, difluoromethylsulfonyl, trifluoromethylsulfonyl and sulfamyl; or a pharmaceutically-acceptable salt thereof.

7. Compound of claim 6 selected from compounds, and their pharmaceutically-acceptable salts, of the group consisting of 5-phenyl-6-[4-(methylsulfonyl)phenyl]spiro[2.4]hept-5-ene;
5-(4-fluorophenyl)-6-[4-(methylsulfonyl)phenyl]-spiro[2.4]hept-5-ene;
5-(4-chlorophenyl)-6-[4-(methylsulfonyl)phenyl]-spiro[2.4]hept-5-ene;
5-(4-methylphenyl)-6-[4-(methylsulfonyl)phenyl]-spiro[2.4]hept-5-ene;
5-(4-methoxyphenyl)-6-[4-(methylsulfonyl)phenyl]-spiro[2.4]hept-5-ene;
5-(4-methylthiophenyl)-6-[4-(methylsulfonyl)phenyl]-spiro[2.4]hept-5-ene;
5-(4-cyanophenyl)-6-[4-(methylsulfonyl)phenyl]-spiro[2.4]hept-5-ene;
5-(4-trifluoromethylphenyl)-6-[4-(methylsulfonyl)-phenyl]spiro[2.4]hept-5-ene;
4-(6-phenylspiro[2.4]hept-5-en-5-yl)benzenesulfonamide;
4-[6-(4-fluorophenyl)spiro[2.4]hept-5-en-5-yl]benzenesulfonamide;
4-[6-(4-chlorophenyl)spiro[2.4]hept-5-en-5-yl]benzenesulfonamide;
4-[6-(4-methylphenyl)spiro[2.4]hept-5-en-5-yl]benzenesulfonamide;
4-[6-(4-methoxyphenyl)spiro[2.4]hept-5-en-5-yl]benzenesulfonamide;
4-[6-(4-methylthiophenyl)spiro[2.4]hept-5-en-5-yl]benzenesulfonamide;
4-[6-(4-cyanophenyl)spiro[2.4]hept-5-en-5-yl]benzenesulfonamide;
4-[6-(4-trifluoromethylphenyl)spiro[2.4]hept-5-en-5yl)-benzenesulfonamide;
6-phenyl-7-[4-(methylsulfonyl)phenyl]spiro[3.4]oct-6-ene;
6-(4-fluorophenyl)-7-[4-(methylsulfonyl)phenyl]-spiro[3.4]oct-6-ene;
6-(4-chlorophenyl)-7-[4-(methylsulfonyl)phenyl]-spiro[3.4]oct-6-ene;
6-(4-methylphenyl)-7-[4-(methylsulfonyl)phenyl]-spiro[3.4]oct-6-ene;
6-(4-methoxyphenyl)-7-[4-(methylsulfonyl)phenyl]-spiro[3.4]oct-6-ene;
6-(4-methylthiophenyl)-7-[4-(methylsulfonyl)phenyl]-spiro[3.4]oct-6-ene;
6-(4-cyanophenyl)-7-[4-(methylsulfonyl)phenyl]-spiro[3.4]oct-6-ene;
6-(4-trifluoromethylphenyl)-7-[4-(methylsulfonyl)-phenyl]spiro[3.4]oct-6-ene;
4-(7-phenylspiro[3.4]oct-6-en-6-yl) benzenesulfonamide;
4-[7-(4-fluorophenyl)spiro[3.4]oct-6-en-6-yl]benzenesulfonamide;
4-[7-(4-chlorophenyl)spiro[3.4]oct-6-en-6-yl]benzenesulfonamide;
4-[7-(4-methylphenyl)spiro[3.4]oct-6-en-6-yl]benzenesulfonamide;
4-[7-(4-methoxyphenyl)spiro[3.4]oct-6-en-6-yl]benzenesulfonamide;
4-[7-(4-methylthiophenyl)spiro[3.4]oct-6-en-6-yl]benzenesulfonamide;
4-[7-(4-cyanophenyl)spiro[3.4]oct-6-en-6-yl]benzenesulfonamide;
4-[7-(4-trifluoromethylphenyl)spiro[3.4]oct-6-en-6-yl]benzenesulfonamide;
2-phenyl-3-[4-(methylsulfonyl)phenyl]spiro[4.4]non-2-ene;
2-(4-fluorophenyl)-3-[4-(methylsulfonyl)phenyl]-spiro[4.4]non-2-ene;
2-(4-chlorophenyl)-3-[4-(methylsulfonyl)phenyl]-spiro[4.4]non-2-ene;
2-(4-methylphenyl)-3-[4-(methylsulfonyl)phenyl]-spiro[4.4]non-2-ene;
2-(4-methoxyphenyl)-3-[4-(methylsulfonyl)phenyl]-spiro[4.4]non-2-ene;
2-(4-methylthiophenyl)-3-[4-(methylsulfonyl)phenyl]-spiro[4.4]non-2-ene;
2-(4-cyanophenyl)-3-[4-(methylsulfonyl)phenyl]-spiro[4.4]non-2-ene;
2-(4-trifluoromethylphenyl)-3-[4-(methylsulfonyl)-phenyl]spiro[4.4]non-2-ene;
4-(3-phenylspiro[4.4]non-2-en-2-yl) benzenesulfonamide;
4-[3-(4-fluorophenyl)spiro[4.4]non-2-en-2-yl]benzenesulfonamide;
4-[3-(4-chlorophenyl)spiro[4.4]non-2-en-2-yl]benzenesulfonamide;
4-[3-(4-methylphenyl)spiro[4.4]non-2-en-2-yl]benzenesulfonamide;
4-[3-(4-methoxyphenyl)spiro[4.4]non-2-en-2-yl]benzenesulfonamide;
4-[3-(4-methylthiophenyl)spiro[4.4]non-2-en-2-yl]benzenesulfonamide;
4-[3-(4-cyanophenyl)spiro[4.4]non-2-en-2-yl]benzenesulfonamide;
4-[3-(4-trifluoromethylphenyl)spiro[4.4]non-2-en-2-yl]benzenesulfonamide;
5-(3-methyl-4-fluorophenyl)-6-[4-(methylsulfonyl)-phenyl]spiro[2.4]hept-5-ene;
5-(3-trifluoromethyl-4-fluorophenyl)-6-[4-(methylsulfonyl)phenyl]spiro[2.4]hept-5-ene;
5-(3-methyl-4-chlorophenyl)-6-[4-(methylsulfonyl)-phenyl]spiro[2.4]hept-5-ene;
5-(3-trifluoromethyl-4-chlorophenyl)-6-[4-(methylsulfonyl)phenyl]spiro[2.4]hept-5-ene;
5-(3-methyl-4-methoxyphenyl)-6-[4-(methylsulfonyl)-phenyl]spiro[2.4]hept-5-ene;
5-(3-trifluoromethyl-4-methoxyphenyl)-6-[4-(methylsulfonyl)phenyl]spiro[2.4]hept-5-ene;
5-(3-fluoro-4-methoxyphenyl)-6-[4-(methylsulfonyl)-phenyl]spiro[2.4]hept-5-ene;
5-(3-chloro-4-methoxyphenyl)-6-[4-(methylsulfonyl)-phenyl]spiro[2.4]hept-5-ene;
5-(4-methoxy-2,3,5,6-tetrafluorophenyl)-6-[4-(methylsulfonyl)phenyl]spiro[2.4]hept-5-ene;
5-(3,4-dimethoxyphenyl)-6-[4-(methylsulfonyl)phenyl]-spiro[2.4]hept-5-ene;

5-(3-chloro-4-fluorophenyl)-6-[4-(methylsulfonyl)-
phenyl]spiro[2.4]hept-5-ene;
4-(4-chloro-3-fluorophenyl)-6-[4-(methylsulfonyl)-
phenyl]spiro[2.4]hept-5-ene;
5-(3,4-difluorophenyl)-6-[4-(methylsulfonyl)phenyl]-
spiro[2.4]hept-5-ene;
5-(3,4-dichlorophenyl)-6-[4-(methylsulfonyl)phenyl]-
spiro[2.4]hept-5-ene;
4-[6-(3-trifluoromethyl-4-fluorophenyl)spiro[2.4]hept-
5-en-5-yl]benzenesulfonamide;
4-[6-(3-trifluoromethyl-4-chlorophenyl)spiro[2.4]hept-
5-en-5-yl]benzenesulfonamide;
4-[6-(3-methyl-4-fluorophenyl)spiro[2.4]hept-5-en-5-
yl]benzenesulfonamide;
4-[6-(3-methyl-4-chlorophenyl)spiro[2.4]hept-5-en-5-
yl]benzenesulfonamide;
4-[6-(4-methoxy-2,3,5,6-tetrafluorophenyl)spiro[2.4-
]hept-5-en-5-yl]benzenesulfonamide;
4-[6-(3-fluoro-4-methoxyphenyl)spiro[2.4]hept-5-en-5-
yl]benzenesulfonamide;
4-[6-(3-trifluoromethyl -4-methoxyphenyl)spiro[2.4-
]hept-5-en-5-yl]benzenesulfonamide;
4-[6-(3-methyl-4-methoxyphenyl)spiro[2.4]hept-5-en-5-
yl]benzenesulfonamide;
4(3-chloro-4-methoxyphenyl)spiro[2.4]hept-5-en-5-
yl]benzenesulfonamide;
4-[6-(4-methoxy-2,3,5,6-tetrafluorophenyl)spiro[2.4-
]hept-5-en-5-yl]benzenesulfonamide;
4-[6-(3,4-dimethoxyphenyl)spiro[2.4]hept-5-en-5-
yl]benzenesulfonamide;
4-[6-(3-chloro-4-fluorophenyl)spiro[2.4]hept-5-en-5-
yl]benzenesulfonamide;
4-[6-(4-chloro-3-fluorophenyl)spiro[2.4]hept-5-en-5-
yl]benzenesulfonamide;
4-[6-(3,4-difluorophenyl)spiro[2.4]hept-5-en-5-yl]ben-
zenesulfonamide; and
4-[6-(3,4-dichlorophenyl)spiro[2.4]hept-5-en-5-yl]ben-
zenesulfonamide.

8. Compound of claim 7 which is 5-(4-fluorophenyl)-
6-[4-(methylsulfonyl)phenyl]spiro[2.4]hept-5-ene, or a
pharmaceutically-acceptable salt thereof.

9. Compound of claim 7 which is 4-[6-(4-fluoro-
phenyl)spiro[2.4]hept-5-en-5yl]benzenesulfonamide, or
a pharmaceutically-acceptable salt thereof.

10. A compound of Formula III

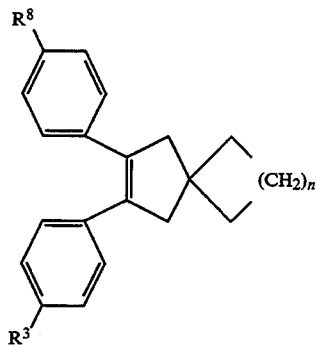

wherein n is a number selected from 0, 1 and
wherein R³ is selected from lower alkylsulfonyl and
sulfamyl; and
wherein R⁸ is independently selected from hydrido,
halo, lower alkyl, lower alkoxy, lower alkylthio,
cyano, lower haloalkyl, lower haloalkoxy, lower
hydroxyalkyl, lower alkoxyalkyl, hydroxyl and mercapto; or a pharmaceutically-acceptable salt
thereof.

11. The compound of claim 10 wherein R³ is methyl-
sulfonyl or sulfamyl; and wherein R⁸ is selected from
hydrido, fluoro, chloro, bromo, iodo, methyl, ethyl,
n-propyl, isopropyl, butyl, tert-butyl, isobutyl, me-
thoxy, ethoxy, propoxy, butoxy, hydroxyl, mercapto,
methylthio, ethylthio, cyano, fluoromethyl, di-
fluoromethyl, trifluoromethyl, chloromethyl, dichloro-
methyl, trichloromethyl, pentafluoroethyl, heptafluoro-
propyl, difluorochloromethyl, dichlorofluoromethyl,
difluoroethyl, difluoropropyl, dichloroethyl, dichloro-
propyl, trifluoromethoxy, hydroxymethyl, methox-
ymethyl and ethoxymethyl; or a pharmaceutically-
acceptable salt thereof.

12. Compound of claim 11 selected from compounds,
and their pharmaceutically-acceptable salts, of the
group consisting of
5-(4-fluorophenyl)-6-[4-(methylsulfonyl)phenyl]-
spiro[2.4]hept-5-ene;
4-[6-(4-fluorophenyl)spiro[2.4]hept-5-en-5-yl]ben-
zenesulfonamide;
6-(4-fluorophenyl)-7-[4-(methylsulfonyl)phenyl]-
spiro[3.4]oct-5-ene;
4-[7-(4-fluorophenyl)spiro[3.4]oct-6-en-6-yl]benzenesul-
fonamide; and
2-(4-fluorophenyl)-3-[4-(methylsulfonyl)phenyl]-
spiro[4.4]non-5-ene.

13. A compound of Formula IV

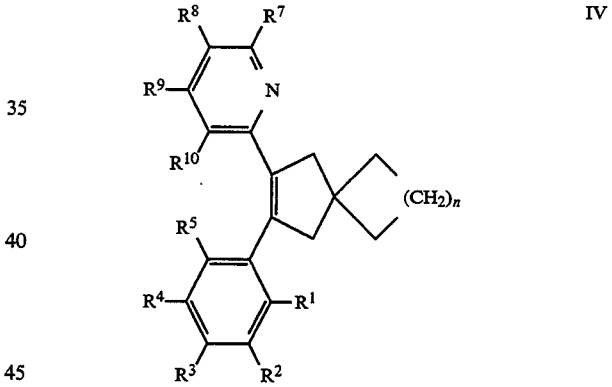

wherein n is a number selected from 0, 1, 2 and 3;and
wherein each of R¹ through R⁵ and R⁷ through R¹⁰ is
independently selected from hydrido, halo, alkyl,
alkoxy, alkylthio, cyano, haloalkyl, hydroxyalkyl,
alkoxyalkyl, hydroxyl, mercapto, alkylsulfonyl and
sulfamyl; or a pharmaceutically-acceptable salt
thereof.

14. Compound of claim 13 wherein n is a number
selected from 0, 1 and 2; wherein each of R¹, R², R⁴, R⁵,
R⁷, R⁹ and R¹⁰ is independently selected from hydrido,
halo, lower alkyl, lower alkoxy, lower alkylthio, cyano,
lower haloalkyl, lower hydroxyalkyl, lower alkoxyal-
kyl, hydroxyl and mercapto; and wherein R³ is selected
from lower alkylsulfonyl and sulfamyl and R⁸ is se-
lected from hydrido, halo, lower alkyl, lower alkoxy,
lower alkylthio, cyano and lower haloalkyl; or wherein
further, R³ is selected from hydrido, halo, lower alkyl,
lower alkoxy, lower alkylthio, cyano and lower haloal-
kyl and R⁸ is selected from lower alkylsulfonyl and
sulfamyl; or a pharmaceutically-acceptable salt thereof.

15. Compound of claim 14 wherein each of R¹, R²,
R⁴, R⁵, R⁷, R⁹ and R¹⁰ is hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl, and $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; or wherein further, $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl, and $R^8$ is methylsulfonyl or sulfamyl; or a pharmaceutically-acceptable salt thereof.

16. Compound of claim 15 selected from compounds, and their pharmaceutically-acceptable salts, of the group consisting of 2-[6-[4-(methylsulfonyl)phenyl]spiro[2.4]hept-5-en-5yl]-pyridine;

5-fluoro-2-[6-[4-(methylsulfonyl)phenyl]spiro[2.4]hept-5-en-5-yl]pyridine;

5-chloro-2-[6-[4-(methylsulfonyl)phenyl]spiro[2.4]hept-5-en-5-yl]pyridine;

5-methyl-2-[6-[4-(methylsulfonyl)phenyl]spiro[2.4]hept-5-en-5-yl]pyridine;

4-[6-(pyridin-2-yl)spiro[2.4]hept-5-en-5-yl]benzenesulfonamide;

4-[6-(5-fluoropyridin-2-yl)spiro[2.4]hept-5-en-5-yl]benzenesulfonamide;

4-[6-(5-chloropyridin-2-yl)spiro[2.4]hept-5-en-5-yl]benzenesulfonamide;

4-[6-(5-methylpyridin-2-yl)spiro[2.4]hept-5-en-5-yl]benzenesulfonamide;

2-[7-[4-(methylsulfonyl)phenyl]spiro[3.4]oct-6-en-6-yl]pyridine;

5-fluoro-2-[7-[4-(methylsulfonyl)phenyl]spiro[3.4]oct-6-en-6-yl]pyridine;

5-chloro-2-[7-[4-(methylsulfonyl)phenyl]spiro[3.4]oct-6-en-6-yl]pyridine;

5-methyl-2-[7-[4-(methylsulfonyl)phenyl]spiro[3.4]oct-6-en-6-yl]pyridine;

4-[7-(pyridin-2-yl)spiro[3.4]oct-6-en-6-yl]benzenesulfonamide;

4-[7-(5-fluoropyridin-2-yl)spiro[3.4]oct-6-en-6-yl]benzenesulfonamide;

4-[7-(5-chloropyridin-2-yl)spiro[3.4]oct-6-en-6-yl]benzenesulfonamide;

4-[7-(5-methylpyridin-2-yl)spiro[3.4]oct-6-en-6-yl]benzenesulfonamide;

2-[3-[4-(methylsulfonyl)phenyl]spiro[4.4]non-2-en-2-yl]pyridine;

5-fluoro-2-[3-[4-(methylsulfonyl)phenyl]spiro[4.4]non-2-en-2-yl]pyridine;

5-chloro-2-[3-[4-(methylsulfonyl)phenyl]spiro[4.4]non-2-en-2-yl]pyridine;

5-methyl-2-[3-[4-(methylsulfonyl)phenyl]spiro[4.4]non-2-en-2-yl]pyridine;

4-[3-(pyridin-2-yl)spiro[4.4]non-2-en-2-yl]benzenesulfonamide;

4-[3-(5-fluoropyridin-2-yl)spiro[4.4]non-2-en-2-yl]benzenesulfonamide;

4-[3-(5-chloropyridin-2-yl)spiro[4.4]non-2-en-2-yl]benzenesulfonamide;

4-[3-(5-methylpyridin-2-yl)spiro[4.4]non-2-en-2-yl]benzenesulfonamide;

2-(6-phenylspiro[2.4]hept-5-en-yl)-5-(methylsulfonyl)pyridine;

2-[6-(4-fluorophenyl)spiro[2.4]hept-5-en-yl]-5-(methylsulfonyl)pyridine;

2-[6-(4-chlorophenyl)spiro[2.4]hept-5-en-yl]-5-(methylsulfonyl)pyridine;

2-[6-(4-methylphenyl)spiro[2.4]hept-5-en-yl]-5-(methylsulfonyl)pyridine;

2-(6-phenylspiro[2.4]hept-5-en-5-yl)-5pyridinesulfonamide;

2-[6-(4-fluorophenyl)spiro[2.4]hept-5-en-5-yl)-5pyridinesulfonamide;

2-[6-(4-chlorophenyl)spiro[2.4]hept-5-en-5-yl)-5pyridinesulfonamide;

2-[6-(4-methylphenyl)spiro[2.4]hept-5-en-5-yl)-5pyridinesulfonamide;

2-(7-phenylspiro[3.4]oct-6-en-6-yl)-5-(methylsulfonyl)pyridine;

2-[7-(4-fluorophenyl)spiro[3.4]oct-6-en-6-yl]-5-(methylsulfonyl)pyridine;

2-[7-(4-chlorophenyl)spiro[3.4]oct-6-en-6-yl]-5-(methylsulfonyl)pyridine;

2-[7-(4-methylphenyl)spiro[3.4]oct-6-en-6-yl]-5-(methylsulfonyl)pyridine;

2-(7-phenylspiro[3.4]oct-6-en-6-yl)-5pyridinesulfonamide;

2-[7-(4-fluorophenyl)spiro[3.4]oct-6-en-6-yl]-5pyridinesulfonamide;

2-[7-(4-chlorophenyl)spiro[3.4]oct-6-en-6-yl]-5pyridinesulfonamide;

2-[7-(4-methylphenyl)spiro[3.4]oct-6-en-6-yl]-5pyridinesulfonamide;

2-(3-phenylspiro[4.4]non-2-en-2-yl)-5-(methylsulfonyl)pyridine;

2-[3-(4-fluorophenyl)spiro[4.4]non-2-en-2-yl]-5-(methylsulfonyl)pyridine;

2-[3-(4-chlorophenyl)spiro[4.4]non-2-en-2-yl]-5-(methylsulfonyl)pyridine;

2-[3-(4-methylphenyl)spiro[4.4]non-2-en-2-yl]-5-(methylsulfonyl)pyridine;

2-(3-phenylspiro[4.4]non-2-en-2-yl)-5pyridinesulfonamide;

2-[3-(4-fluorophenyl)spiro[4.4]non-2-en-2-yl]-5pyridinesulfonamide;

2-[3-(4-chlorophenyl)spiro[4.4]non-2-en-2-yl]-5pyridinesulfonamide; and

2-[3-(4-methylphenyl)spiro[4.4]non-2-en-2-yl]-5pyridinesulfonamide.

17. A compound of Formula V

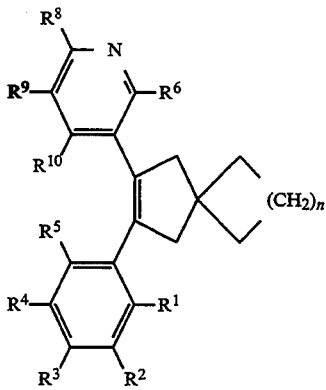

V wherein n is a number selected from 0, 1, 2 and 3; and wherein each of $R^1$ through $R^6$ and $R^8$ through $R^{10}$ is independently selected from hydrido, halo, alkyl, alkoxy, alkylthio, cyano, haloalkyl, hydroxyalkyl, alkoxyalkyl, hydroxyl, mercapto, alkylsulfonyl and sulfamyl; or a pharmaceutically-acceptable salt thereof.

18. Compound of claim 17 wherein n is a number selected from 0, 1 and 2; wherein each of $R^1$, $R^2$, $R^4$, $R^5$, $R^6$, $R^9$ and $R^{10}$ is independently selected from hydrido, halo, lower alkyl, lower alkoxy, lower alkylthio, cyano, lower haloalkyl, lower hydroxyalkyl, lower alkoxyalkyl, hydroxyl and mercapto; and wherein $R^3$ is selected from lower alkylsulfonyl and sulfamyl and $R^8$ is selected from hydrido, halo, lower alkyl, lower alkoxy, lower alkylthio, cyano and lower haloalkyl; or wherein further, $R^3$ is selected from hydrido, halo, lower alkyl, lower alkoxy, lower alkylthio, cyano and lower haloalkyl and $R^8$ is selected from lower alkylsulfonyl and sulfamyl; or a pharmaceutically-acceptable salt thereof.

19. Compound of claim 18 wherein each of $R^1$, $R^2$, $R^4$, $R^5$, $R^6$, $R^9$ and $R^{10}$ is hydrido, fluoro, chloro, bromo, iodo, methyl, ethyl, n-propyl, isopropyl, butyl, tert-butyl, isobutyl, methoxy, ethoxy, propoxy, butoxy, hydroxyl, mercapto, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl and $R^8$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; or wherein further, $R^3$ is selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl, and $R^8$ is methylsulfonyl or sulfamyl; or a pharmaceutically-acceptable salt thereof.

20. Compound of claim 19 selected from compounds, and their pharmaceutically-acceptable salts, of the group consisting of 5-[6-[4-(methylsulfonyl)phenyl]spiro[2.4]hept-5-en-5-yl]pyridine;

2-fluoro-5-[6-[4-(methylsulfonyl)phenyl]spiro[2.4]hept-5-en-5-yl]pyridine;

2-chloro-5-[6-[4-(methylsulfonyl)phenyl]spiro[2.4]hept-5-en-5-yl]pyridine;

2-methyl-5-[6-[4-(methylsulfonyl)phenyl]spiro[2.4]hept-5-en-5-yl]pyridine;

4-[6-(pyridin-5-yl)spiro[2.4]hept-5-en-5-yl]benzenesulfonamide;

4-[6-(2-fluoropyridin-5-yl)spiro[2.4]hept-5-en-5-yl]benzenesulfonamide;

4-[6-(2-chloropyridin-5-yl)spiro[2.4]hept-5-en-5-yl]benzenesulfonamide;

4-[6-(2-methylpyridin-5-yl)spiro[2.4]hept-5-en-5-yl]benzenesulfonamide;

5-[7-[4-(methylsulfonyl)phenyl]spiro[3.4]oct-6-en-6-yl]pyridine;

2-fluoro-5-[7-[4-(methylsulfonyl)phenyl]spiro[3.4]oct-6-en-6-yl]pyridine;

2-chloro-5-[7-[4-(methylsulfonyl)phenyl]spiro[3.4]oct-6-en-6-yl]pyridine;

2-methyl-5-[7-[4-(methylsulfonyl)phenyl]spiro[3.4]oct-6-en-6-yl]pyridine;

4-[7-(pyridin-5-yl)spiro[3.4]oct-6-en-6-yl]benzenesulfonamide;

4-[7-(2-fluoropyridin-5-yl)spiro[3.4]oct-6-en-6-yl]benzenesulfonamide;

4-[7-(2-chloropyridin-5-yl)spiro[3.4]oct-6-en-6-yl]benzenesulfonamide;

4-[7-(2-methylpyridin-5-yl)spiro[3.4]oct-6-en-6-yl]benzenesulfonamide;

5-[3-[4-(methylsulfonyl)phenyl]spiro[4.4]non-2-en-2-yl]pyridine;

2-fluoro-5-[3-[4-(methylsulfonyl)phenyl]spiro[4.4]non-2-en-2-yl]pyridine;

2-chloro-5-[3-[4-(methylsulfonyl)phenyl]spiro[4.4]non-2-en-2-yl]pyridine;

2-methyl-5-[3-[4-(methylsulfonyl)phenyl]spiro[4.4]non-2-en-2-yl]pyridine;

4-[3-(pyridin-5-yl)spiro[4.4]non-2-en-2-yl]benzenesulfonamide;

4-[3-(2-fluoropyridin-5-yl)spiro[4.4]non-2-en-2-yl]benzenesulfonamide;

4-[3-(2-chloropyridin-5-yl)spiro[4.4]non-2-en-2-yl]benzenesulfonamide;

4-[3-(2-methylpyridin-5-yl)spiro[4.4]non-2-en-2-yl]benzenesulfonamide;

5-(6-phenylspiro[2.4]hept-5-en-5-yl)-2-(methylsulfonyl)pyridine;

5-[6-(4-fluorophenyl)spiro[2.4]hept-5-en-5-yl]-2-(methylsulfonyl)pyridine;

5-[6-(4-chlorophenyl)spiro[2.4]hept-5-en-5-yl]-2-(methylsulfonyl)pyridine;

5-[6-(4-methylphenyl)spiro[2.4]hept-5-en-5-yl]-2-(methylsulfonyl)pyridine;

5-(6-phenylspiro[2.4]hept-5-en-5-yl)-2pyridinesulfonamide;

5-[6-(4-fluorophenyl)spiro[2.4]hept-5-en-5-yl]-2pyridinesulfonamide;

5-[6-(4-chlorophenyl)spiro[2.4]hept-5-en-5-yl]-2pyridinesulfonamide;

5-[6-(4-methylphenyl)spiro[2.4]hept-5-en-5-yl]-2pyridinesulfonamide;

5-(7-phenylspiro[3.4]oct-6-en-6-yl)-2-(methylsulfonyl)-pyridine;
5-[7-(4-fluorophenyl)spiro[3.4]oct-6-en-6-yl]-2-(methylsulfonyl)pyridine;
5-[7-(4-chlorophenyl)spiro[3.4]oct-6-en-6-yl]-2-(methylsulfonyl)pyridine;
5-[7-(4-methylphenyl)spiro[3.4]oct-6-en-6-yl]-2-(methylsulfonyl)pyridine;
5-(7-phenylspiro[3.4]oct-6-en-6-yl)-2pyridinesulfonamide;
5-[7-(4-fluorophenyl)spiro[3.4]oct-6-en-6-yl]-2-pyridinesulfonamide;
5-[7-(4-chlorophenyl)spiro[3.4]oct-6-en-6-yl]-2-pyridinesulfonamide;
5-[7-(4-methylphenyl)spiro[3.4]oct-6-en-6-yl]-2-pyridinesulfonamide;
5-(3-phenylspiro[4.4]non-2-en-2-yl)-2-(methylsulfonyl)-pyridine;
5-[3-(4-fluorophenyl)spiro[4.4]non-2-en-2-yl]-2-(methylsulfonyl)pyridine;
5-[3-(4-chlorophenyl)spiro[4.4]non-2-en-2-yl]-2-(methylsulfonyl)pyridine;
5-[3-(4-methylphenyl)spiro[4.4]non-2-en-2-yl]-2-(methylsulfonyl)pyridine;
5-(3-phenylspiro[4.4]non-2-en-2-yl)-2pyridinesulfonamide;
5-[3-(4-fluorophenyl)spiro[4.4]non-2-en-2-yl]-2pyridinesulfonamide;
5-[3-(4-chlorophenyl)spiro[4.4]non-2-en-2-yl]-2pyridinesulfonamide; and
5-[3-(4-methylphenyl)spiro[4.4]non-2-en-2-yl]-2pyridinesulfonamide.

21. A compound of Formula VI

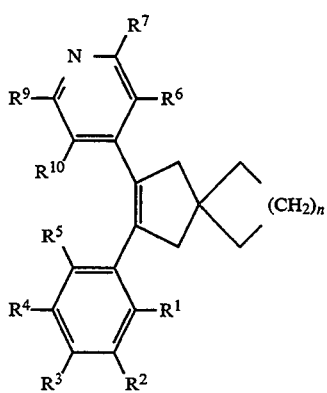

VI wherein n is a number selected from 0, 1, and 3; and
wherein each of $R^1$ through $R^7$, $R^9$ and $R^{10}$ is independently selected from hydrido, halo, alkyl, alkoxy, alkylthio, cyano, haloalkyl, hydroxyalkyl, alkoxyalkyl, hydroxyl, mercapto, alkylsulfonyl and sulfamyl; or a pharmaceutically-acceptable salt thereof.

22. Compound of claim 21 wherein n is a number selected from 0, 1 and 2; wherein each of $R^1$, $R^2$, $R^4$ through $R^7$, $R^9$ and $R^{10}$ is independently selected from hydrido, halo, lower alkyl, lower alkylthio, cyano, hydroxyl, mercapto, lower haloalkyl, lower alkoxy, lower hydroxyalkyl and lower alkoxyalkyl; and wherein $R^3$ is selected from lower alkylsulfonyl and sulfamyl; or a pharmaceutically-acceptable salt thereof.

23. Compound of claim 22 wherein each of $R^1$, $R^2$, $R^4$ through $R^7$, $R^9$ and $R^{10}$ is independently selected from hydrido, fluoro, chloro, bromo, iodo, methyl, ethyl, n-propyl, isopropyl, butyl, tert-butyl, isobutyl, methoxy, ethoxy, propoxy, butoxy, methylthio, ethylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, methoxymethyl and ethoxymethyl; and wherein $R^3$ is methylsulfonyl or sulfamyl; or a pharmaceutically-acceptable salt thereof.

24. Compound of claim 23 selected from compounds, and their pharmaceutically-acceptable salts, of the group consisting of
4-[6-[4-(methylsulfonyl)phenyl]spiro[2.4]hept-5-en-5-yl]pyridine;
4-[6-(4-pyridinyl)spiro[2.4]hept-5-en-5-yl]benzenesulfonamide;
4-[7-[4-(methylsulfonyl)phenyl]spiro[3.4]oct-6-en-6-yl]pyridine;
4-[7-(4-pyridinyl)spiro[3.4]oct-6-en-6-yl]benzenesulfonamide;
4-[3-[4-(methylsulfonyl)phenyl]spiro[4.4]non-2-en-2-yl]pyridine; and
4-[3-(4-pyridinyl)spiro[4.4]non-2-en-2-yl]benzenesulfonamide.

25. A pharmaceutical composition comprising a therapeutically-effective amount of a compound, said compound selected from a family of compounds of claim 4; or a pharmaceutically-acceptable salt thereof.

26. A pharmaceutical composition comprising a therapeutically-effective amount of a compound, said compound selected from a family of compounds of claim 5; or a pharmaceutically-acceptable salt thereof.

27. A pharmaceutical composition comprising a therapeutically-effective amount of a compound, said compound selected from a family of compounds of claim 6; or a pharmaceutically-acceptable salt thereof.

28. A pharmaceutical composition comprising a therapeutically-effective amount of a compound, said compound selected from a family of compounds of claim 7; or a pharmaceutically-acceptable salt thereof.

29. A pharmaceutical composition comprising a therapeutically-effective amount of a compound, said compound selected from a compound of claim 8; or a pharmaceutically-acceptable salt thereof.

30. A pharmaceutical composition comprising a therapeutically-effective amount of a compound, said compound selected from a compound of claim 9; or a pharmaceutically-acceptable salt thereof.

31. A method of treating inflammation or an inflammation-associated disorder in a subject, said method comprising administering to the subject having such inflammation or inflammation-associated disorder, a therapeutically-effective amount of a compound of claim 4; or a pharmaceutically-acceptable salt thereof.

32. A method of treating inflammation or an inflammation-associated disorder in a subject, said method comprising administering to the subject having such inflammation or inflammation-associated disorder, a therapeutically-effective amount of a compound of claim 5; or a pharmaceutically-acceptable salt thereof.

33. A method of treating inflammation or an inflammation-associated disorder in a subject, said method comprising administering to the subject having such inflammation or inflammation-associated disorder, a therapeutically-effective amount of a compound of claim 6; or a pharmaceutically-acceptable salt thereof.

34. A method of treating inflammation or an inflammation-associated disorder in a subject, said method comprising administering to the subject having such inflammation or inflammation-associated disorder, a therapeutically-effective amount of a compound of claim 7; or a pharmaceutically-acceptable salt thereof.

35. A method of treating inflammation or an inflammation-associated disorder in a subject, said method comprising administering to the subject having such inflammation or inflammation-associated disorder, a therapeutically-effective amount of a compound of claim 8; or a pharmaceutically-acceptable salt thereof.

36. A method of treating inflammation or an inflammation-associated disorder in a subject, said method comprising administering to the subject having such inflammation or inflammation-associated disorder, a therapeutically-effective amount of a compound of claim 9; or a pharmaceutically-acceptable salt thereof.

37. The method of claim 31 for use in treatment of inflammation.

38. The method of claim 31 for use in treatment of an inflammation-associated disorder.

39. The method of claim 38 wherein the inflammation-associated disorder is arthritis.

40. The method of claim 38 wherein the inflammation-associated disorder is pain.

41. The method of claim 38 wherein the inflammation-associated disorder is fever.

* * * * *